US012747200B2

(12) United States Patent
Shen et al.

(10) Patent No.: US 12,747,200 B2
(45) Date of Patent: Sep. 29, 2026

(54) CAPSAICIN ANALOGS AND USES THEREOF

(71) Applicant: Young BioPharma, LLC, Lowell, MA (US)

(72) Inventors: Young Shen, Andover, MA (US); Junke Liu, Jamaica Plain, MA (US)

(73) Assignee: Young BioPharma, LLC, Lowell, MA (US)

( * ) Notice: Subject to any disclaimer, the term of this patent is extended or adjusted under 35 U.S.C. 154(b) by 588 days.

(21) Appl. No.: 18/035,697

(22) PCT Filed: Nov. 4, 2021

(86) PCT No.: PCT/US2021/072234

§ 371 (c)(1),
(2) Date: May 5, 2023

(87) PCT Pub. No.: WO2022/099284

PCT Pub. Date: May 12, 2022

(65) Prior Publication Data

US 2024/0116856 A1 Apr. 11, 2024

Related U.S. Application Data

(60) Provisional application No. 63/109,970, filed on Nov. 5, 2020.

(51) Int. Cl.
*C07C 235/24* (2006.01)
*A61P 25/04* (2006.01)
(Continued)

(52) U.S. Cl.
CPC ............ *C07C 235/24* (2013.01); *A61P 25/04* (2018.01); *A61P 35/00* (2018.01); *C07C 235/20* (2013.01);
(Continued)

(58) Field of Classification Search
CPC ................ C07C 235/24; C07C 235/20; C07C 237/20; C07C 255/63; C07C 311/30; A61P 35/00; C07D 211/26; C07D 263/14
See application file for complete search history.

(56) References Cited

U.S. PATENT DOCUMENTS 5,962,532 A * 10/1999 Campbell et al.
2004/0077663 A1 4/2004 Benish et al.
(Continued)

OTHER PUBLICATIONS

Walpole et al. (J. Med. Chem. 1993, 36, 2381-2389) (Year: 1993).*
(Continued)

*Primary Examiner* — Brandon J Fetterolf

(74) *Attorney, Agent, or Firm* — Morse, Barnes-Brown & Pendleton, P.C.; Lisa M. Warren, Esq.; Daniel L. Branson, Esq.

(57) ABSTRACT

The present invention provides compositions comprising compounds having formulas (I), (II) or (I)

(Continued)

-continued (II)

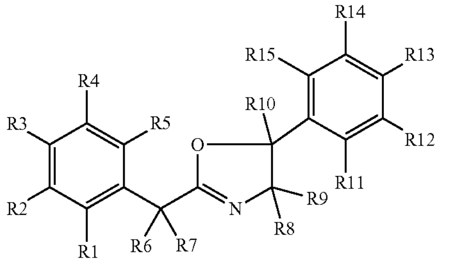

(III)

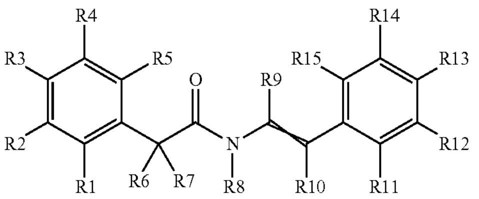

and additionally provides methods for the use thereof in the treatment of various disorders including neurological disorders, cancer, diabetes, and obesity, wherein R1-R7, X, A, and Q in (I), R1-R15 in (II) and R1-R15 in (III) are as defined herein. In certain embodiments, methods for the treatment of various disorders including pain and cancer comprise topically, locally or systemically (e.g., IV, IP or orally) administering to a subject in need thereof a therapeutically effective amount of a compound of formulas (I), (II) or (III).

18 Claims, 13 Drawing Sheets

(51) Int. Cl.

| | |
|---|---|
| ***A61P 35/00*** | (2006.01) |
| ***C07C 235/20*** | (2006.01) |
| ***C07C 237/20*** | (2006.01) |
| ***C07C 255/63*** | (2006.01) |
| ***C07C 311/30*** | (2006.01) |
| ***C07D 211/26*** | (2006.01) |
| ***C07D 263/14*** | (2006.01) |

(52) U.S. Cl.

CPC .......... *C07C 237/20* (2013.01); *C07C 255/63* (2013.01); *C07C 311/30* (2013.01); *C07D 211/26* (2013.01); *C07D 263/14* (2013.01)

(56) References Cited

U.S. PATENT DOCUMENTS

2015/0087714 A1 3/2015 Bean et al.
2017/0342094 A1 11/2017 Gurney et al.

OTHER PUBLICATIONS

Berge, et al., "Pharmaceutical Salts," Journal of Pharmaceutical Sciences, 66(I): 1-19 (1977).

Brinkerhoff, et al., "Monte Carlo Simulations of Receptor Dynamics: Insights into Cell Signaling," Journal of Molecular Histology, 35: 667-677 (2004).

Brito, et al., "TRPVI: A Potential Drug Target for Treating Various Diseases," Cells, 3:517-545 (2014).

Chen, et al., "Outcomes of Surgical Repair for Persistent Truncus Arteriosus from Neonates to Adults: A Single Center's Experience," PLoS ONE, 11(1):1-11 (2016).

Chen, et al., "Utility of Large-Scale Transiently Transfected Cells for Cell-Based High-Throughput Screens to Identify Transient Receptor Potential Channel AI (TRPAI) Antagonists," Journal of Biomolecular Screening 12(1): 61-69 (2007).

De Lago, et al., "Arvanil, a Hybrid Endocannabinoid and Vanilloid Compound, Behaves as an Antihyperkinetic Agent in a Rat Model of Huntington's Disease," Brain Research, 1050: 210-216 (2005).

Hauck, et al., "FRNK Blocks v-Src-stimulated Invasion and Experimental Metastases Without Effects on Cell Motility or Growth," The EMBO Journal, 21(23): 6289-6302 (2002).

Hayman, et al., "Capsaicin: A review of its Pharmacology and Clinical Applications," Current Anaesthesia & Critical Care 19: 338-343 (2008).

International Search Report from International Application No. PCT/US2021/072234; date mailed: Feb. 24, 2022.

Kawada, et al., "Oxazoles in Organic Chemistry. 2. Application to the Synthesis of Benzylisoquinoline Alkaloids," J. Org. Chem., 45: 2548-2550 (1980).

Morales-MartÃ•nez, et al., "The Prospective Antiobesity Effect of Capsaicin Synthetic Analogs: A Matter of Weight," Med chem (Los Angeles), 6(5): 365-371 (2016).

Mori, et al., "Capsaicin, a Component of Red Peppers, Inhibits the Growth of Androgen-Independent, p53 Mutant Prostate Cancer Cells," Cancer Res; 66 (6): 3222-3229 (2006).

Nelson, "The Constitution of Capsaicin, the Pungent Principle of Capsicum," JACS, 41: 1115 (1919).

Palazzo, et al., "Transient Receptor Potential Vanilloid Type 1 and Pain Development," Current Opinion in Pharmacology, 12:9-17 (2012).

Pridgen, et al., "Oxazolines. 2.1 2-Substituted 2-0xazolines as Synthons for N-(ß-Hydroxyethyl)arylalkylamines, Intermediates in a Synthesis of 1,2,3,4-Tetrahydroisoquinolines and 2,3,4,5-Tetrahydro-IH-3-Benzazepines," J. Org. Chem., 47(11): 1985-1989 (1982).

Pubchem, Substance Record for SID 15614622, Available Date: Oct. 25, 2006 [retrieved on Dec. 22, 2021). Retrieved from the Internet: <URL: https:l/pubchem.ncbi.nlm.nih.gov/substance/15614622>.

Pubchem, Substance Record for SID 26752522, Available Date: Nov. 9, 2007 [retrieved on Dec. 15, 2021). Retrieved from the Internet: <URL: https:l/pubchem.ncbi.nlm.nih.gov/substance/26752522>.

Sanchez-Sanchez, et al., "Evaluation of the Antitumour Activity of Rinvanil and Phenylacetylrinvanil on the Cervical Cancer Tumour Cell Lines HeLa, CaSKi and ViBo," European Journal of Pharmacology 758: 129-136 (2015).

Shen, et al., "Discovery of an in vitro and in vivo Potent Resorcylic Lactone Analog of LL-21640-2 as Anti-inflammatory Lead, II," Bioorganic & Medicinal Chemistry Letters, 20: 3047-3049 (2010).

Shen, et al., "Discovery of Anti-inflammatory Clinical Candidate E6201, Inspired from Resorcylic Lactone LL-ZI 640-2, III," Bioorganic & Medicinal Chemistry Letters, 20: 3155-3157 (2010).

Sánchez-Bailón, et al., "Src Kinases Catalytic Activity Regulates Proliferation, Migration and Invasiveness of MDA-MB-231 Breast Cancer Cells," Cellular Signalling, 24: 1276-1286 (2012).

URL: https://medlineplus.gov/breastcancer.html, (2020).

Walpole, et al., "Analogues of Capsaicin with Agonist Activity as Novel Analgesic Agents; Structure-Activity Studies. 1. The Aromatic "A-Region"," J. Med. Chem., 36: 2362-2372 (1993).

Walpole, et al., "Analogues of Capsaicin with Agonist Activity as Novel Analgesic Agents; Structure-Activity Studies. 2. The Amide Bond "B-Region",", J. Med. Chem, 36: 2373-2380 (1993).

Walpole, et al., "Analogues of Capsaicin with Agonist Activity as Novel Analgesic Agents; Structure-Activity Studies. 3. The Hydrophobic Side-Chain "C-Region"," J. Med. Chem., 36: 2381-2389 (1993).

Zheng, et al., "Dietary Capsaicin and its Anti-obesity Potency: from Mechanism to Clinical Implications," Bioscience Reports, 37: 1-9 (2017).

* cited by examiner

YB-2
$EC_{50}$ = 0.082 uM

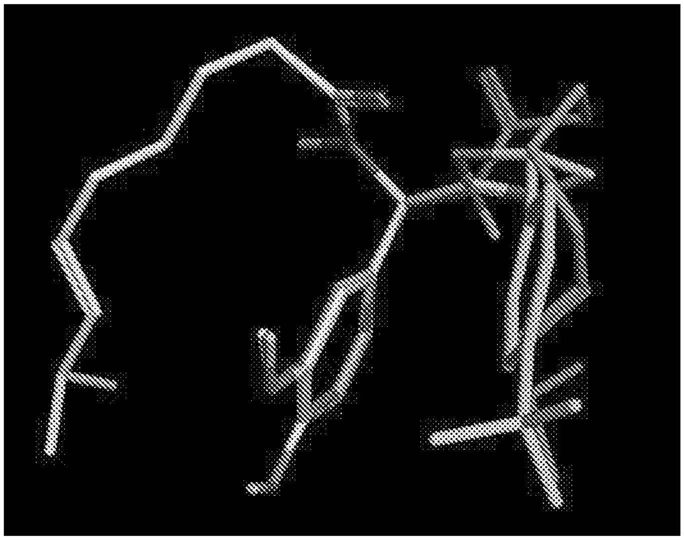
FIG. 4: low energy conformations: Capsaicin, YB-4, N-Me capsaicin
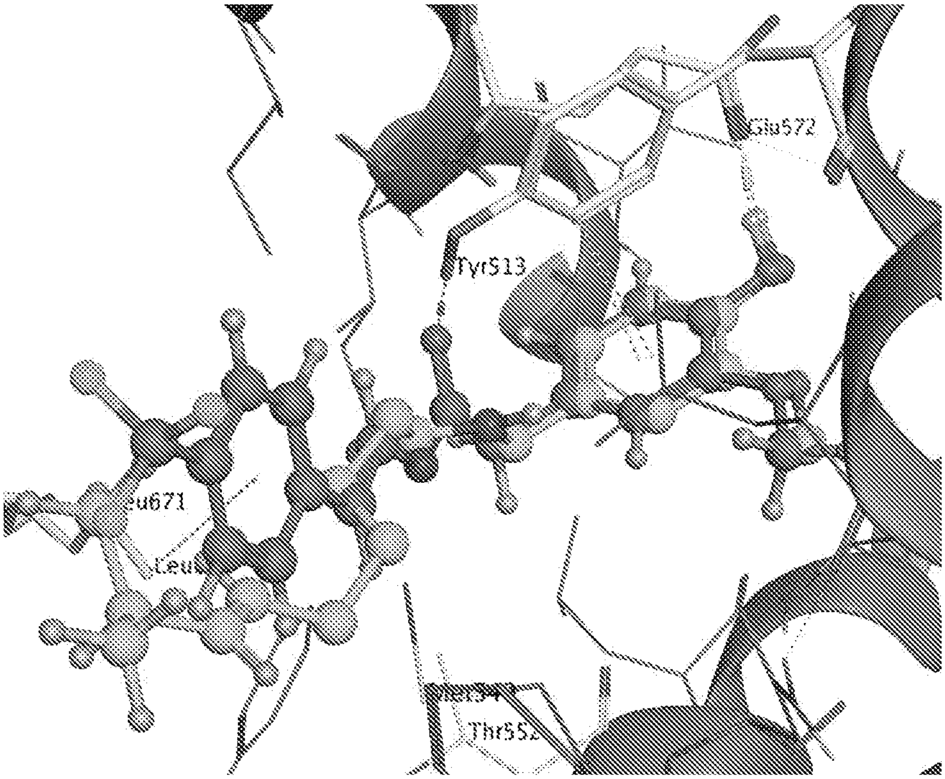
FIG. 5: YB-11 and Capsaicin in TRPV1 binding pocket Capsaicin

YB-16

YB-11

Cell invasion: 1. Control (DMSO); 2. Capsaicin (40 uM); 3. YB-1 (10 uM).

CAPSAICIN ANALOGS AND USES THEREOF

RELATED APPLICATIONS

This application is a national stage filing under 35 U.S.C. 371 of International Application PCT/US2021/072234, filed Nov. 4. 2021, which claims the benefit under 35 U.S.C. § 119 (e) of U.S. Provisional Application No. 63/109,970, filed on Nov. 5, 2020. The entire teachings of the above applications are incorporated herein by reference. International Application PCT/US2021/072234 was published under PCT Article 21(2) in English.

GOVERNMENT SUPPORT

This invention was made with government support under Award Number R43DA050405 awarded by the National Institute on Drug Abuse of the National Institutes of Health. The government has certain rights in the invention.

BACKGROUND OF THE INVENTION

Capsaicin (trans-8-methyl-N-vanillyl-6-nonenamide) (1), a naturally-occurring compound found in chili peppers, has been used as a spice and medicine for centuries. It is a hydrophobic and highly pungent compound. It was discovered by Tresh in 1846 and its chemical structure was determined by Nelson in 1919 (*J. Am. Chem. Soc.* 1919, 41, 1115).

(1)

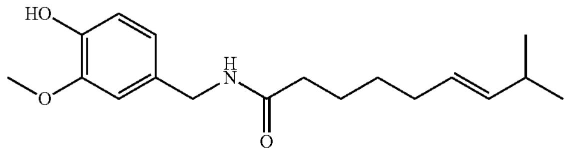

Following years of study, it has been demonstrated that capsaicin has important pharmacological effects of which antinociception was the first evidenced ((*Curr Anaesth Crit Care* 2008, 19, 338-343). Capsaicin has demonstrated beneficial effects on pain relief. This therapeutic effect is believed to be achieved by opening the transient receptor potential vanilloid 1 (TRPV1) channel. TRPV1 is a nonselective cation channel that allows the transient influx of $Ca^{2+}$ when is activated during the detection and transduction of nociceptive stimuli (*Curr Opin Pharmacol* 2012, 12, 9-17). Within the peripheral nervous system, this channel is selectively expressed on the terminals of nociceptors (pain sensory fibers). After a brief period of activation, capsaicin induces a long-term desensitization of nociceptors related to calcium influx into the nociceptive nerve terminals (Aδ and C fibers). This desensitization is likely due to a reversible retraction of innervation. Based on studies of the skin, it is known that the nociceptors grow back during a period of weeks to months. In the meantime, there is a profound attenuation of pain sensibility but not of other sensory functions (*Arthritis & Rheumatology* 2019, 71, 1524; *Pharmacol Rev.* 2012, 64, 939; *Mol Pain* 2015, 11, 22; *Physiol Res* 2008, 57 Suppl 3:S59-68).

Capsaicin is used as an analgesic in topical ointments and dermal patches to relieve pain, typically in concentrations between 0,025% and 0.1% (*Molecules* 2016, 21, 844). It may be applied in cream form for the temporary relief of minor aches and pains of muscles and joints associated with arthritis, backache, strains and sprains, often in compounds with other rubefacients. It is also used to reduce the symptoms of peripheral neuropathy, such as post-herpetic neuralgia caused by shingles. A review of clinical studies described that topical capsaicin provided moderate to substantial pain relief from post-herpetic neuralgia, HIV-neuropathy, and diabetic neuropathy (*The Cochrane Database of Systematic Reviews* 2017, 1, CD007393). Capsaicin creams have been used to treat psoriasis for reduction of itching. In addition, various pieces of data support a role of TRPV1 in the control of diabetes, insulin resistance and obesity (*Cells* 2014, 3, 517). Capsaicin has also shown potential effects as anti-obesity drug (*Bioscience Reports* 2017, 37, 1).

Arvanil (a capsaicin analog) has been demonstrated to have a beneficial effect in a rat model of Huntington's disease, reducing ambulatory and stereotypic activity, and increasing the activity (*Brain Res* 2005, 1050, 210). Moreover, Arvanil has also shown to have a beneficial effect in neuronal affectations such as astrocytomas and mild cognitive impairment (*Nat. Med* 2012, 18, 1232). PhAR (a capsaicin analogue) induces apoptosis in leukaemia cell lines, such as P388, J774 and WEHI-3 (*Oncol Lett* 2014, 7, 1651) and it also inhibits in vitro cell proliferation of carcinogenic cells such as HeLa. CasKi and ViBo (*Eur J Pharmacol* 2015, 758, 129).

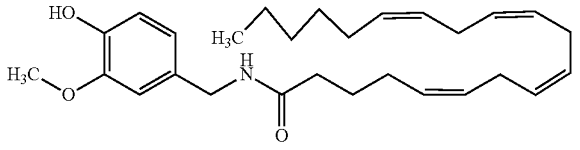

Arvanil

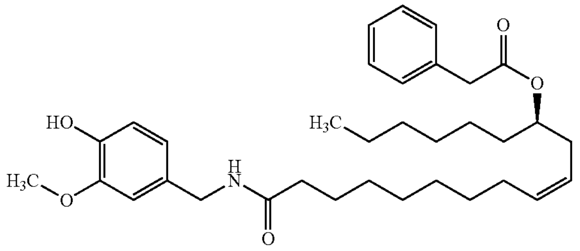

PhAR

Capsaicin showed inhibitory effects against cancer cells of different origin (*Molecules* 2016, 21, 931). It is known that capsaicin can inhibit the proliferation of human and mouse tumor cell lines without affecting normal cell proliferation. It has been found that pro-apoptotic activity of capsaicin is mediated via TRPV1. Several other mechanisms have also been reported.

The activity of capsaicin on breast cancer, prostate cancer and pancreatic cancer cells in vitro and in vivo had been reported (*Oncogene*, 2010, 29, 285; *Cancer Res.* 2006, 66, 3222; *Apoptosis* 2008, 13, 1465). This natural product inhibited growth of ER-positive (MCF-7, T47D, BT-474) and ER-negative (SKBR-3, MDA-MB-231) breast cancer cell lines. Notably, capsaicin blocked breast cancer cell migration in vitro and decreased by 50% the size of MDA- MB-231 breast cancer tumors growing orthotopically in immunodeficient mice without noticeable drug side effects.

It has been reported that capsaicin down-regulates the expression of not only prostate-specific antigen (PSA), but also androgenic receptors, the steroid-activated proteins that control expression of specific growth-related genes. The American Association for Cancer Research reports that capsaicin is able to kill prostate cancer cells by causing them to undergo apoptosis. Capsaicin inhibited the activity of NF-kappa beta, a molecular mechanism that participates in the pathways leading to apoptosis in many cell types. Capsaicin also inhibited the tumor formation by human prostate cancer cell cultures inoculted in mouse models; results showed that treated tumors were about one-fifth the size of untreated tumors (*Cancer Res.* 2006, 66, 3222). Promoter assays also showed that capsaicin inhibited the ability of dihydrotestosterone to activate the PSA enhancer, even in the presence of exogenous androgenic receptors (ARs) in LNCaP cells. This suggests that capsaicin inhibited the transcription of PSA not only via down-regulation of AR expression, but also by a direct inhibitory effect. Although capsaicin reduced the amount of AR that the tumor cells produced, it did not interfere with normal movement of AR into the nucleus of the cancer cells, where the steroid receptor acts to regulate androgen target genes (American Association for Cancer Research (2006). Pepper component hot enough to trigger suicide in prostate cancer cells. www.eurekalert.org/pub_releases/2006-03/aafc-pch031306.php.)

In both males and females, lung cancer is one of the most lethal cancers worldwide and accounts for >30% of cancer-related deaths (*Onco Targets Ther.* 2017, 10, 1921; www-.medicalnewstoday.com/articles/324911). Most deaths occur as a result of the cancer metastasizing, or spreading, to distant parts of the body. After testing capsaicin in human non-small cell lung cancer cells, the researchers found that capsaicin stopped the first stage of metastasis, which is called "invasion." The researchers also fed mice with lung cancer a diet enhanced with capsaicin and found that these rodents had a much smaller number of metastatic cancer cells in their lungs compared with mice that did not receive the treatments. The researchers carried out cell experiments and found that capsaicin can block the activation of the Src protein—a protein that is key in regulating the proliferation, survival, and motility of the cells (MedicalNewsToday 2019. www.medicalnewstoday.com/articles/324911). Phosphorylation activates Src kinase activity, and Src kinase activity regulates proliferation, migration and invasiveness of cancer cells (*Cellular Signalling,* 2012, 24, 1276*; Biochimica et Biophysica Acta,* 2002, 1602, 114).

The in vitro and in vivo data indicates that capsaicin has a potential role in the treatment of cancer. The relatively low potency ($IC_{50}$s in hundreds of micromolar range against most cancer cell lines in vitro) limits the clinical application of this compound. Breast cancer, lung cancer and other cancers commonly metastasize to secondary locations like the brain, liver, or bone, making them difficult to treat. It would be of particular interest to develop more potent capsaicin analogs into novel therapies to combat cancer and cancer metastasis in cancer patients as a single therapy or a combination therapy with other anticancer agents, such as camptothecin (*Biochem pharmacol.* 2017, 129, 54).

The compound CNTX-4975 (injectable formulation of capsaicin) is in clinical trials to treat chronic pain due to knee osteoarthritis and Morton's neuroma, a rare nerve disorder in the foot (www.practicalpainmanagement.com/treatments/pharmacological/non-opioids/analgesics-future-novel-capsaicin-formulation-entx-4975). Qutenza® (capsaicin 8% patch) was approved to manage neuropathic pain (www.neurologylive.com/view/fda-approves-qutenza-for-treatment-of-neuropathic-pain). The patch is undergoing a late-stage trial in patients with osteoarthritis pain (https://clinicaltrials.gov/ct2/show/NCT03153813). Another compound CA-008 (capsaicin prodrug) is in a Phase 2 trial for patients with post-surgical pain (www.concentricanalgesics.com/pipeline).

Despite the tremendous medicinal potential of capsaicin, high pungency of capsaicin (16.0 million Scoville Heat Units (SHU)) causes serious side effects including burning, stinging or erythema at the site of application and restricts the broad application of this compound (*J. Am. Osteopath. Assoc.* 2007, 107, S8-S13; MedicalNewsToday 2019. www-.medicalnewstoday.com/articles/324911). The high pungency has forced clinical trials to employ lower concentrations of capsaicin than those used in preclinical tests (in vitro and in vivo), making it difficult to achieve therapeutic endpoints [*Med Chem* (Los Angeles) 2016, 6, 365-371]. In addition to pungency, application of capsaicin is further hindered by the low aqueous solubility (solubility in water 0.013 mg/mL), which limits the routes of administration. The inherent pungency and hydrophobicity of capsaicin severely hamper the effectiveness and broad use of capsaicin for the treatment of neurological disorders, cancers, diabetes and obesity. It is of great importance to test the hypothesis that the TRPV1 activity of capsaicin can be separated from the pungency and hydrophobicity.

Clearly, there remains a need to develop synthetic methodologies to access and examine the therapeutic effect of novel analogues of capsaicin, particularly those that are inaccessible by making modifications to the natural product or through enzymatic synthesis. It would also be of particular interest to develop novel compounds that exhibit a favorable therapeutic profile (e.g., are less pungent and more soluble in water, while retaining potent TRPV1 agonistic activity and/or enhancing anticancer activity).

SUMMARY OF THE INVENTION

The present invention encompasses novel capsaicin analogs, pharmaceutical compositions comprising these capsaicin analogs, methods of using these analogs/compositions to treat conditions and diseases associated with the transient receptor potential cation channel subfamily V member 1 (TRPV1) and/or Src protein, and kits comprising these novel capsaicin analogs or pharmaceutical compositions. As described herein, the capsaicin analogs exhibit these key characteristics as compared to capsaicin: decreased pungency; improved solubility and lower toxicity. Importantly, the analogs described herein also exhibit strong analgesic effects and demonstrate the ability to inhibit cancer growth in vivo. As described above, the high pungency of capsaicin causes serious side effects and limits the dosing level in clinical use. It is demonstrated herein that structural modifications to the capsaicin molecule can significantly reduce pungency yet retain the key characteristics of improved solubility, lower toxicity, analgesic activity or cancer growth inhibition activity. Thus, the capsaicin analogs and pharmaceutical compositions described herein can be dosed at highly efficacious levels (e.g., above typical capsaicin levels/doses) resulting in therapeutic endpoints easier to achieve than with capsaicin.

In particular, the present invention provides compounds of general formulas (I), (II) and (III):

(I)

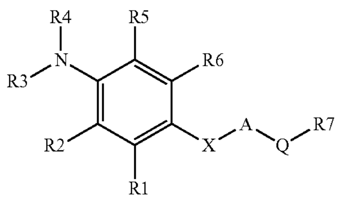

(II)

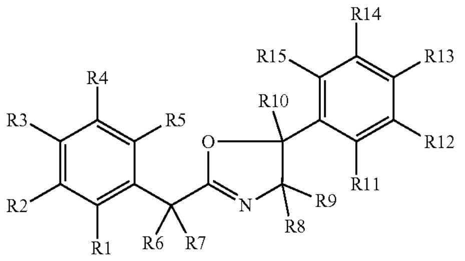

(III)

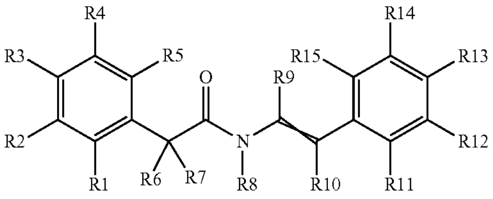

and derivatives, e.g., pharmaceutically acceptable derivatives, thereof. Also encompassed by the present invention are compositions, specifically pharmaceutical compositions, comprising a compound, or a combination of compounds, of the general formulas I, II and/or Ill above as the active ingredient(s), and a pharmaceutically acceptable carrier or diluent. More specifically, the present invention encompasses compounds of formula I, II or III wherein R1-R7, X, A, and Q in (1). R1-R15 in (II) and R1-R15 in (III) are as defined generally and in classes and subclasses herein. In certain embodiments, the compound is present in an amount effective to activate TRP receptors and/or block the activation of the Src protein. In certain exemplary embodiments, the TRP receptor is TRPV1 and the compound is present in a therapeutically effective amount sufficient to activate the TRP receptor, and specifically the TRPV1 receptor.

The present invention also encompasses methods for the use of compounds of formulas (I), (II) and (III), typically in a pharmaceutical composition, in the treatment of various disorders, conditions and diseases associated the TRP receptor and/or the Src protein, specifically through enhancing or increasing the biological activity of, or the up-regulation of a TRP receptor and/or blocking the activation of the Src protein. Such disorders, conditions and diseases include neurological disorders, cancers, diabetes and obesity. Methods of treatment of these and other conditions comprise administration of the compounds described herein, or a combination of these compounds via topical, local injection or systematic. In certain embodiments, the method comprises topically, locally or systemically (e.g., i.v., i.p. or orally) administering to a subject in need thereof a therapeutically effective amount of a compound of formulas (I), (II) and (III), a derivative thereof or a combination thereof, in an amount sufficient to treat the disorder, or substantially alleviate, or reduce the pathological effects of the disorder, in the subject. More specifically, the compound is present in an amount effective to activate TRP receptors and/or reduce the activated Src protein associated with the disorder(s). In certain exemplary embodiments, the TRP receptor is TRPV1. For example, the compounds described herein can be used as analgesics in pharmaceutical compositions in methods for treating pain. As another example, the compounds described herein can be used as single therapies or combination therapies with other anticancer agents in pharmaceutical compositions in methods for treating cancer.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 4 represents low energy conformations: Capsaicin, YB-4, N-Me capsaicin.

FIG. 5 represents YB-11 and capsaicin in TRPV1 binding pocket.

DETAILED DESCRIPTION OF THE PREFERRED EMBODIMENTS

Figure 1:
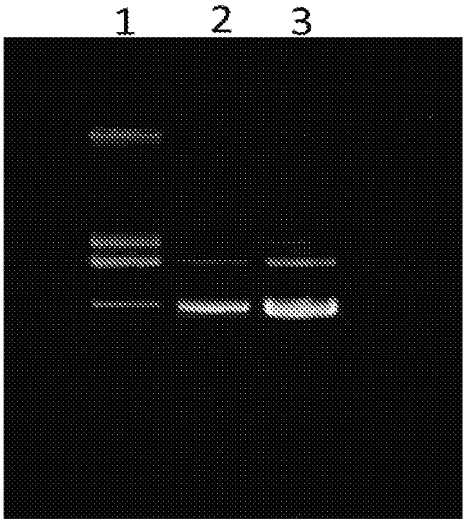
FIG. 1 is a photograph of a gel showing the results of a large scale purification of human TRPV1/pcDNA3.1+/C-(K)DYK plasmid DNA. Lane 1: 300 ng (parental plasmid DNA), Lane 2: 200 ng newly purified plasmid, Lane 3: 400 ng newly purified plasmid.

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof.

In recognition of the need to access and further explore the biological activity of novel analogues of capsaicin, the present invention provides novel compounds, as described in herein, which demonstrate reduced pungency, increased solubility, potent TRPV1 activation, and/or reduced Src protein activation.

The compounds of the present invention, and pharmaceutical compositions thereof, are useful for the treatment of various diseases, disorders or conditions associated with a transient receptor potential receptor and/or the Src protein. In particular, the disease, disorder or condition is treated with one or more of the compounds described herein wherein the compound activates the TRP receptor and/or blocks the activation of the Src protein associated with the disease, disorder or condition. Such diseases include e.g., central nervous system diseases, diabetes, obesity and cancers. In certain embodiments, the compounds of the present invention can be used for the treatment of diseases and disorders including, but not limited to aches and pains (e.g., aches and pains of muscles and joints associated with arthritis, post-surgical pain, Morton's Neuroma, backache, cancer pain, strains and sprains, diabetic pain, pain caused by shingles and HIV infection), itching caused by psoriasis, Huntington's disease, neuronal affectations such as astrocytomas and mild cognitive impairment, diabetes, obesity, and cancer.

1) General Description of Compounds of the Invention

In certain embodiments, the compounds of the invention include compounds of the general formulas (I), (II) and (III) as further defined below:

(I)

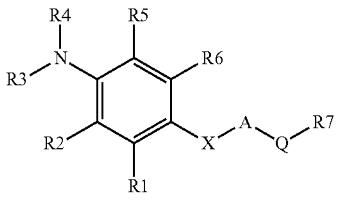

-continued (II)

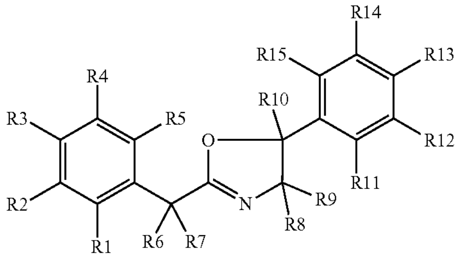

(III)

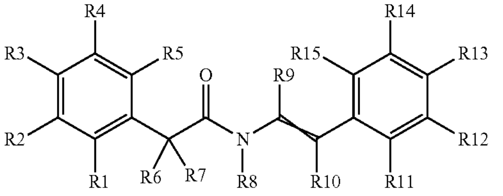

In formula (I):

wherein R1 is hydrogen, halogen, aliphatic, hydroxyl, or protected hydroxyl;

R2 is hydroxyl, protected hydroxyl, amine or protected amine;

R3 and R4 are each independently hydrogen, an aliphatic, heteroaliphatic, alicyclic, heteroalicyclic, non-urea carbonyl or sulfonyl moiety; or R3 and R4, when taken together, may form a substituted or unsubstituted, saturated or unsaturated cyclic ring;

R5 is hydrogen, halogen, aliphatic, hydroxyl, or protected hydroxyl;

R6 is hydrogen, halogen, aliphatic, hydroxyl, or protected hydroxyl;

R7 is substituted or unsubstituted, saturated or unsaturated aliphatic, heteroaliphatic chain with total number of non-hydrogen heavy atoms ≥8 for all cases except total number of non-hydrogen heavy atoms ≥9 when R7 is unsubstituted saturated aliphatic chain;

X is O, CH2 or S;

A is O, NH, N-alkyl, or carbonyl;

Q is NH, N-alkyl, or carbonyl; and pharmaceutically acceptable derivatives thereof.

The following structures illustrate several exemplary types of compounds of this class. Other compounds of the invention will be readily apparent to the reader:

YB-1

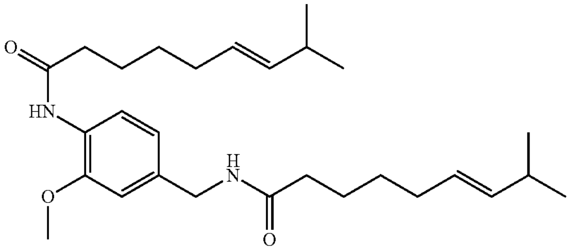

-continued

YB-2

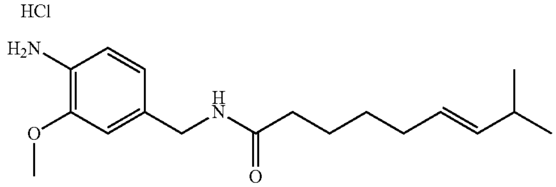

YB-6

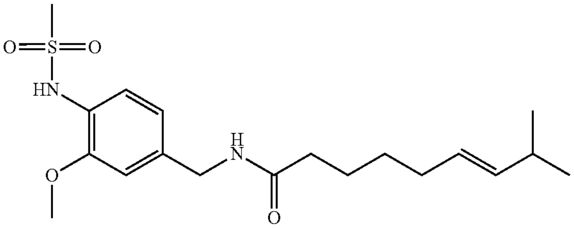

YB-7

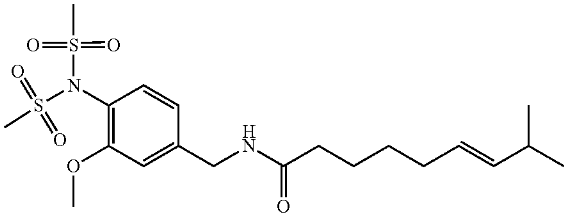

YB-8

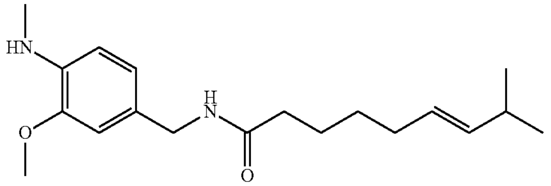

YB-9

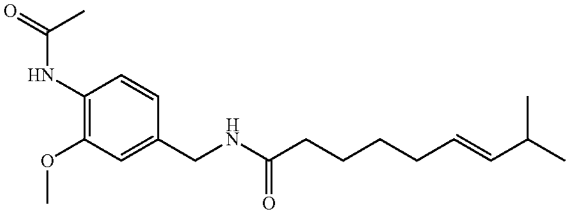

YB-13

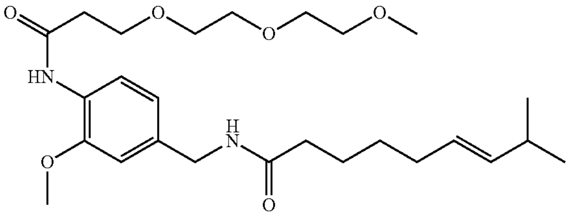

In formula (II):

wherein R1 is hydrogen, halogen, aliphatic, hydroxyl, or protected hydroxyl;

R2 is hydroxyl, protected hydroxyl, amine or protected amine;

R3 is hydroxyl, amine or protected amine;

R4 is hydrogen, halogen, aliphatic, hydroxyl, or protected hydroxyl;

R5 is hydrogen, halogen, aliphatic, hydroxyl, or protected hydroxyl;

R6 and R7 are each independently hydrogen, an aliphatic, heteroaliphatic, alicyclic, heteroalicyclic or carbonyl; or R6 and R7, when taken together, may form a substituted or unsubstituted, saturated or unsaturated cyclic ring;

R8 is hydrogen, or aliphatic;

R9 is hydrogen, or aliphatic;

R10 is hydrogen, or aliphatic;

R11 is hydrogen, halogen, NO2, haloalkyl, sulfonyl, carbonyl, aliphatic, heteroaliphatic, alicyclic, heteroalicyclic, aromatic, amine, protected amine, hydroxyl, or protected hydroxyl;

R12 is hydrogen, halogen, NO2, haloalkyl, sulfonyl, carbonyl, aliphatic, heteroaliphatic, alicyclic, heteroalicyclic, aromatic, amine, protected amine, hydroxyl, or protected hydroxyl;

R13 is hydrogen, halogen, NO2, haloalkyl, sulfonyl, carbonyl, aliphatic, heteroaliphatic, alicyclic, heteroalicyclic, aromatic, amine, protected amine, hydroxyl, or protected hydroxyl;

R14 is hydrogen, halogen, NO2, haloalkyl, sulfonyl, carbonyl, aliphatic, heteroaliphatic, alicyclic, heteroalicyclic, aromatic, amine, protected amine, hydroxyl, or protected hydroxyl;

R15 is hydrogen, halogen, NO2, haloalkyl, sulfonyl, carbonyl, aliphatic, heteroaliphatic, alicyclic, heteroalicyclic, aromatic, amine, protected amine, hydroxyl, or protected hydroxyl; and pharmaceutically acceptable derivatives thereof.

The following structures illustrate several exemplary types of compounds of this class. Other compounds of the invention will be readily apparent to the reader:

YB-3

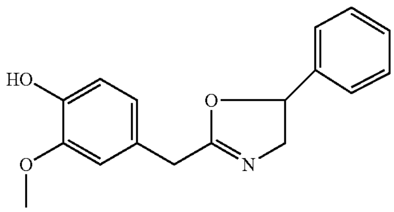

YB-4

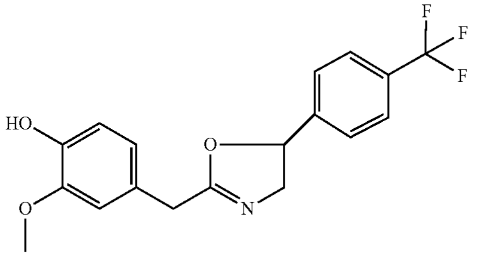

YB-5

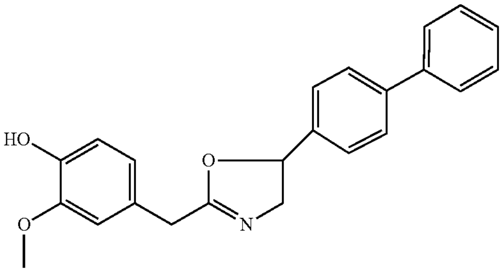

In formula (III):

wherein R1 is hydrogen, halogen, aliphatic, hydroxyl, or protected hydroxyl;

R2 is hydroxyl, protected hydroxyl, amine or protected amine;

R3 is hydroxyl, protected hydroxyl except for alkoxy, amine or protected amine;

R4 is hydrogen, halogen, aliphatic, hydroxyl, or protected hydroxyl;

R5 is hydrogen, halogen, aliphatic, hydroxyl, or protected hydroxyl;

R6 and R7 are each independently hydrogen, an aliphatic, heteroaliphatic, alicyclic, heteroalicyclic or carbonyl; or R6 and R7, when taken together, may form a substituted or unsubstituted, saturated or unsaturated cyclic ring;

R8 is hydrogen, or aliphatic;

R9 is hydrogen, or aliphatic;

R10 is hydrogen, or aliphatic;

R11 is hydrogen, halogen, CN, NO2, haloalkyl, sulfonyl, carbonyl, aliphatic, heteroaliphatic, alicyclic, heteroalicyclic, aromatic, amine, protected amine, hydroxyl, or protected hydroxyl;

R12 is hydrogen, halogen, CN, NO2, haloalkyl, sulfonyl, carbonyl, aliphatic, heteroaliphatic, alicyclic, heteroalicyclic, aromatic, amine, protected amine, hydroxyl, or protected hydroxyl;

R13 is hydrogen, halogen, CN, NO2, haloalkyl, sulfonyl, carbonyl, aliphatic, heteroaliphatic, alicyclic, heteroalicyclic, aromatic, amine, protected amine, hydroxyl, or protected hydroxyl;

R14 is hydrogen, halogen, CN, NO2, haloalkyl, sulfonyl, carbonyl, aliphatic, heteroaliphatic, alicyclic, heteroalicyclic, aromatic, amine, protected amine, hydroxyl, or protected hydroxyl;

R15 is hydrogen, halogen, CN, NO2, haloalkyl, sulfonyl, carbonyl, aliphatic, heteroaliphatic, alicyclic, heteroalicyclic, aromatic, amine, protected amine, hydroxyl, or protected hydroxyl; and pharmaceutically acceptable derivatives thereof.

The following structures illustrate some exemplary types of compounds of this class. Other compounds of the invention will be readily apparent to the reader:

YB-10

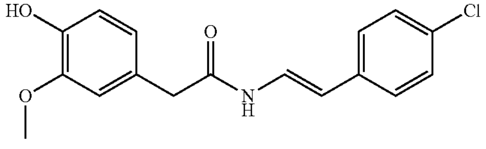

YB-11

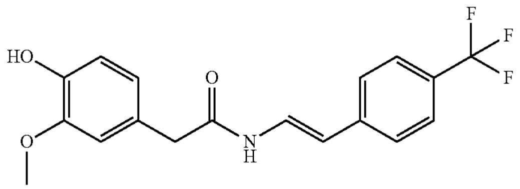 [SMILES: COc1cc(CC(=O)N/C=C/c2ccc(C(F)(F)F)cc2)ccc1O]

-continued
YB-12
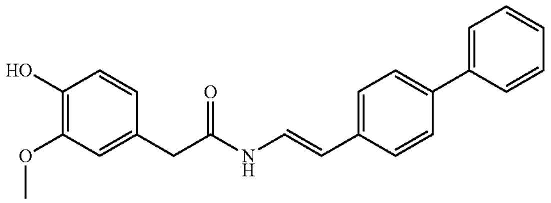
YB-14
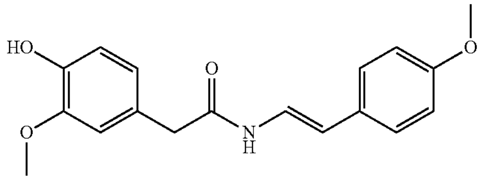
YB-15
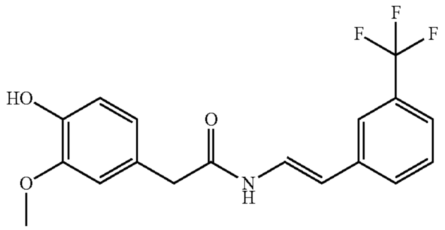 [SMILES: COc1cc(CC(=O)N/C=C/c2cccc(C(F)(F)F)c2)ccc1O]
YB-16
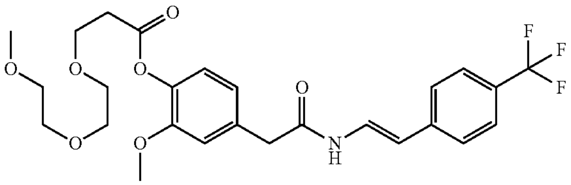 [SMILES: COCCOCCOCCC(=O)Oc1ccc(CC(=O)N/C=C/c2ccc(C(F)(F)F)cc2)cc1OC]
YB-17
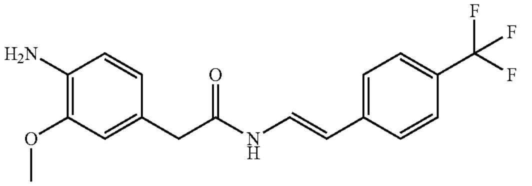
YB-18
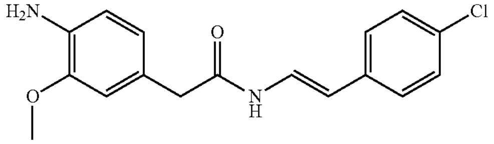
YB-19
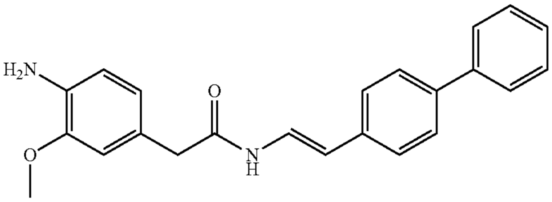
-continued
YB-20
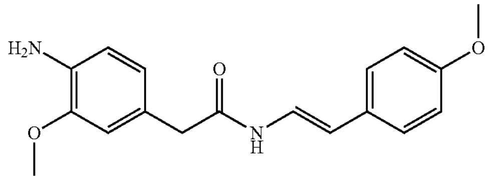
YB-21
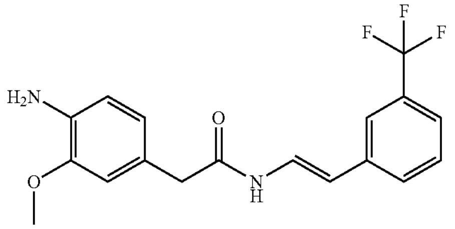
YB-22
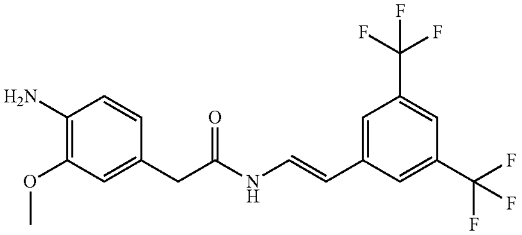
YB-23
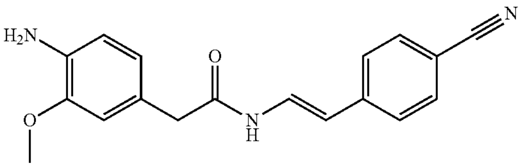
YB-29
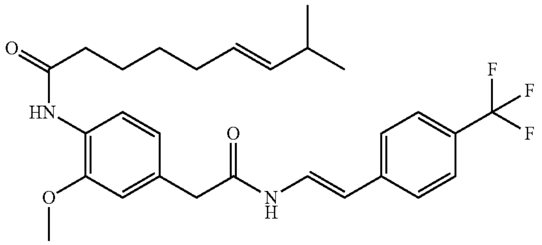
YB-30
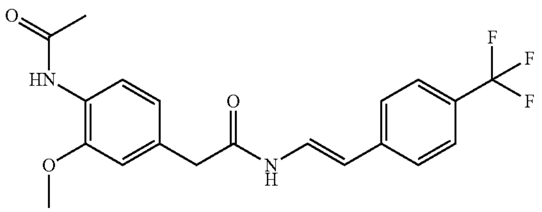

-continued

YB-31

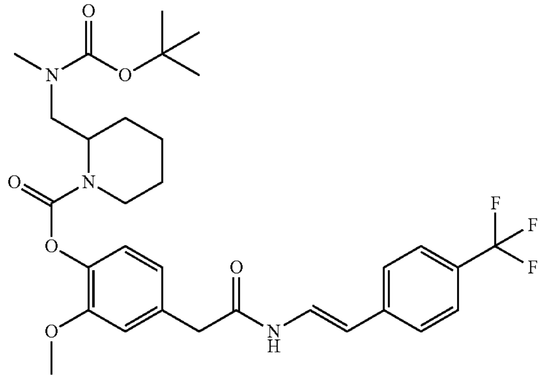

YB-35

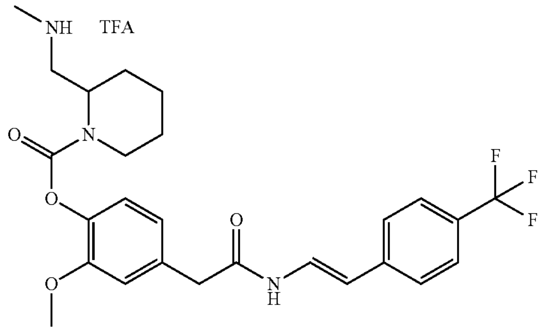

Some of the foregoing compounds can comprise one or more stereocenters, and thus can exist in various isomeric forms. Thus, inventive compounds and pharmaceutical compositions thereof may be in the form of an individual enantiomer, diastereomer or geometric isomer, or may be in the form of a mixture of stereoisomers. In certain embodiments, the compounds of the invention are isomerically pure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., mixtures of Z and E isomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of compounds of formula (I), (II) or (III) under different conditions and may exist as one or a combination of polymorphs of compound of general formula (I), (II) or (III) forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses the inventive compounds of formulas I, II, and III and their derivatives, e.g., their tautomeric forms, their stereoisomers, their polymorphs, their salts, esters, salts of such esters, their solvates, prodrugs, other adduct or derivative of the compounds and so forth.

2) Compounds and Definitions

As discussed above, this invention provides novel compounds with a range of biological properties. Compounds of this invention have biological activities relevant for the treatment of neurological disorders, diabetes, obesity, and cancers. In certain embodiments, the compounds of the invention are useful for the treatment of pain. In certain embodiments, the compounds of the invention are useful for the treatment of cancers.

Compounds of this invention include those specifically set forth above and described herein, and are illustrated in part by the various classes, subgenera and species disclosed elsewhere herein.

Additionally, the present invention provides pharmaceutically acceptable derivatives of the inventive compounds, and methods of treating a subject using these compounds, pharmaceutical compositions thereof, or either of these in combination with one or more additional therapeutic agents. The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Pro-drugs of a variety of compounds, and materials and methods for derivatizing the parent compounds to create the prodrugs, are known and may be adapted to the present invention. Certain exemplary pharmaceutical compositions and pharmaceutically acceptable derivatives will be discussed in more detail herein below.

Certain compounds of the present invention, and definitions of specific functional groups are also described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. By the term "protecting group", as used herein, it is meant that a particular functional moiety, e.g., O, S, or N, is temporarily blocked so that a reaction can be carried out selectively at another reactive site in a multi-functional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by Reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example of neurological disorders, diabetes, obesity, and cancer. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH2 cyclopropyl, cyclobutyl, —CH2-cyclobutyl, cyclopentyl, —CH2-cyclopentyl, cyclohexyl, —CH2 cyclohexyl, cyclohexenylethyl, cyclohexanylethyl, norbornyl moieties and the like, which again, may bear one or more substituents.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl group contains 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. The term "aminoalkyl" refers to a group having the structure NH2R'—, wherein R' is alkyl, as defined herein. In certain embodiments, the alkyl group contains 1-20 aliphatic carbon atoms. In certain other embodiments, the alkyl group contains 1-10 aliphatic carbon atoms. In yet other embodiments, the alkyl group contains 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO2; —CN; —CF3; —CH2CF3; —CHCl2; —CH2OH; —CH2CH2OH; —CH2NH2; —CH2SO2CH3; —C(O)Rx; —CO2(Rx); —CON(Rx)2; —OC(O)Rx; OCO2Rx; —OCON(Rx)2; —N(Rx)2; —S(O)2Rx; —NRx(CO)Rx wherein each occurrence of Rx independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. It will also be appreciated that aryl and heteroaryl moieties, as defined herein may be attached via an aliphatic, alicyclic, heteroaliphatic, heteroalicyclic, alkyl or heteroalkyl moiety and thus also include -(aliphatic)aryl, -(heteroaliphatic)aryl, -(aliphatic)heteroaryl, -(heteroaliphatic)heteroaryl, -(alkyl)aryl, -(heteroalkyl)aryl, -(alkyl)heteroaryl, and -(heteroalkyl)heteroaryl moieties. Thus, as used herein, the phrases "aryl or heteroaryl" refer to "aryl, heteroaryl, -(aliphatic)aryl, -(heteroaliphatic)aryl, -(aliphatic)heteroaryl, -(heteroaliphatic)heteroaryl, -(alkyl)aryl, -(heteroalkyl)aryl, -(alkyl)heteroaryl, and -(heteroalkyl)heteroaryl moieties". Substituents include, but are not limited to, any of the previously mentioned substituents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl and the like. In certain embodiments of the present invention, the term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one, two or three of the hydrogen atoms thereon independently with any one or more of the following moieties including, but not limited to: aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO2; —CN; —CF3; —CH2CF3; —CHCl2; CH2OH; —CH2CH2OH; —CH2NH2; —CH2SO2CH3; —C(O)Rx; —CO2(Rx); —CON(Rx)2; —OC(O)Rx; OCO2Rx; —OCON(Rx)2; —N(Rx)2; —S(O)2Rx; —NRx(CO)Rx wherein each occurrence of Rx independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "cycloalkyl", as used herein, refers specifically to groups having three to ten, preferably three to seven carbon atoms. Suitable cycloalkyls include, but are not limited to cyclopropyl, cyclobutyl, cyclopentyl, cyclohexyl, cycloheptyl and the like, which, as in the case of aliphatic, heteroaliphatic or heterocyclic moieties, may optionally be substituted with substituents including, but not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO2; —CN; —CF3; —CH2CF3; —CHCl2; CH2OH; —CH2CH2OH; —CH2NH2; —CH2SO2CH3; —C(O)Rx; —CO2(Rx); —CON(Rx)2; —OC(O)Rx; OCO2Rx; —OCON(Rx)2; —N(Rx)2; —S(O)2Rx; —NRx(CO)Rx wherein each occurrence of Rx independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be branched or linear unbranched. In certain embodiments, heteroaliphatic moieties are substituted by independent replacement of one or more of the hydrogen atoms thereon with one or more moieties including, but not limited to aliphatic; alicyclic; heteroaliphatic; heteroalicyclic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO2; —CN; —CF3; CH2CF3; —CHCl2; —CH2OH; —CH2CH2OH; —CH2NH2; —CH2SO2CH3; —C(O)Rx; —CO2(Rx); CON(Rx)2; —OC(O)Rx; —OCO2Rx; —OCON(Rx)2; —N(Rx)2; —S(O)2Rx; —NRx(CO)Rx wherein each occurrence of Rx independently includes, but is not limited to, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heteroalicyclic", as used herein, refers to compounds which combine the properties of heteroaliphatic and cyclic compounds and include but are not limited to saturated and unsaturated mono- or polycyclic heterocycles such as morpholino, pyrrolidinyl, furanyl, thiofuranyl, pyrrolyl etc., which are optionally substituted with one or more functional groups, as defined herein.

Additionally, it will be appreciated that any of the alicyclic or heteroalicyclic moieties described above and herein may comprise an aryl or heteroaryl moiety fused thereto. Additional examples of generally applicable substituents are illustrated by the specific embodiments shown in the Examples that are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO2; —CN; CF3; —CH2CF3; —CHCl2; —CH2OH; —CH2CH2OH; —CH2NH2; —CH2SO2CH3; C(O)Rx; —CO2(Rx); CON(Rx)2; —OC(O)Rx; —OCO2Rx; —OCON(Rx)2; —N(Rx)2; —S(O)2Rx; NRx(CO)Rx wherein each occurrence of Rx independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples or generally applicable substituents are illustrated by the specific embodiments shown in the Examples, which are described herein.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heteroalicyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aryl", "heteroaryl" and the like encompass both substituted and unsubstituted groups.

3) Synthetic Methodology

As described above, the present invention provides novel capsaicin analogs having formula (I), (II) or (III) as described above and in certain classes and subclasses herein. An overview of an exemplary synthesis of the inventive compounds is provided below, as detailed in Schemes 1-3, and in the Exemplification herein. It will be appreciated that the methods as described herein can be applied to each of the compounds as disclosed herein and equivalents thereof. Additionally, the reagents and starting materials are well known to those skilled in the art. Although the following scheme describes certain exemplary compounds, it will be appreciated that the use of alternate starting materials will yield other analogs of the invention.

As depicted in Scheme 1, and as described in the examples herein, two components were coupled to give aniline analogs. Amino group in aniline was further derivatized to prepare sulfonamides, alkyl amine and amides to provide novel capsaicin analogs having formula (I).

Scheme 1

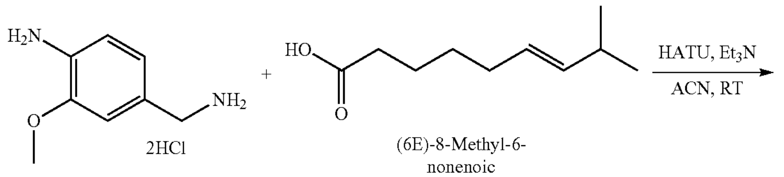

2HCl 4-(aminomethyl)-2-methoxy aniline dihydrochloride (6E)-8-Methyl-6-nonenoic acid -continued
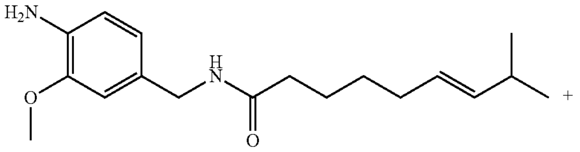
YB-2
44%
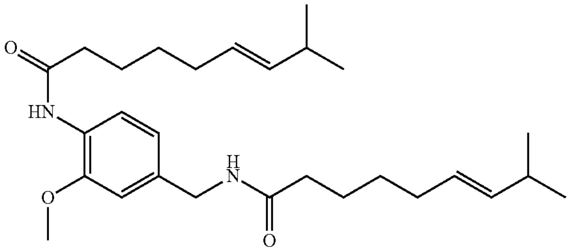
YB-1
17%
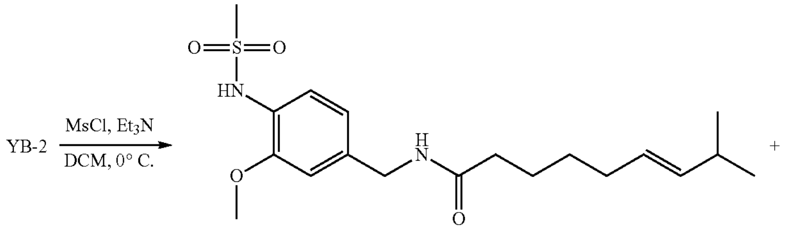
YB-6
13%
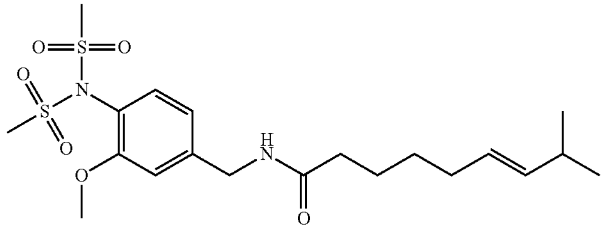
YB-7
14%
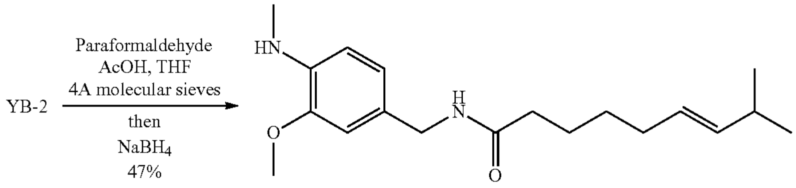
YB-8
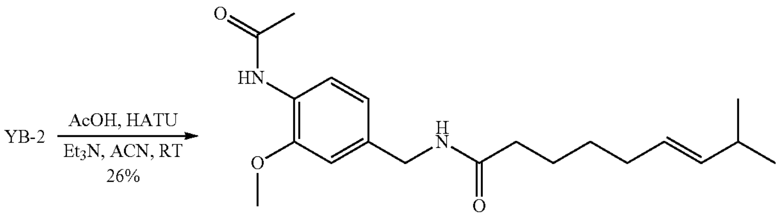
YB-9
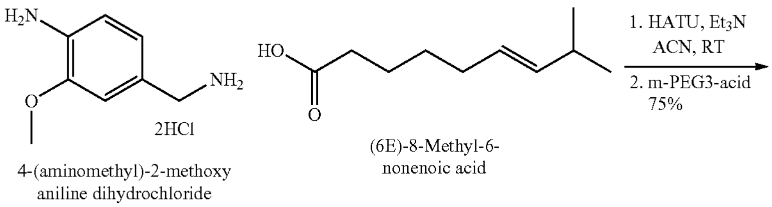
4-(aminomethyl)-2-methoxy aniline dihydrochloride
(6E)-8-Methyl-6-nonenoic acid -continued

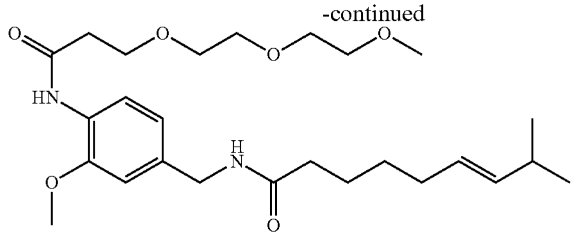

YB-13

As depicted in Scheme 2, and as described in the examples herein, after phenol protection, two components were coupled to give amide intermediates. Five-member ring was formed through a 2-step sequence to provide novel analogs having formula (II).

Scheme 2

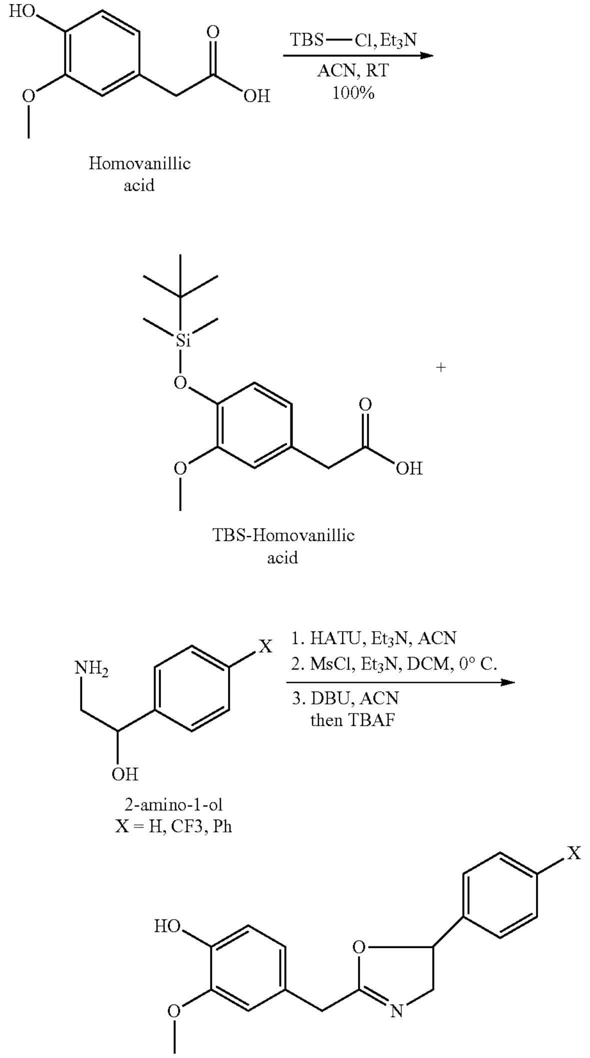

Homovanillic acid

TBS-Homovanillic acid 2-amino-1-ol
X = H, CF3, Ph

X = H, YB-3, 38%
X = CF3, YB-4, 34%
X = Ph, YB-5, 43%

As depicted in Scheme 3, and as described in the examples herein, after TBS-Homovanillic acid was converted into Pivaloyloxylamide in 2 steps, two components were coupled, followed by deprotection to provide novel analogs YB-10-12, 14-15, and 22-23 having formula (III). Similarly, after 2-(4-amino-3-methoxyphenyl)acetic acid was converted into N-pivaloyloxyl amide in 2 steps, two components were coupled, followed by deprotection to provide novel analogs YB-17-21 having formula (III). Hydroxyl group in analog YB-11 was further derivatized to prepare new analogs YB-16, 31, and 35 having formula (III). Amino group in analog YB-17 was further derivatized to prepare new analogs YB-29 and 30 having formula (III).

Scheme 3

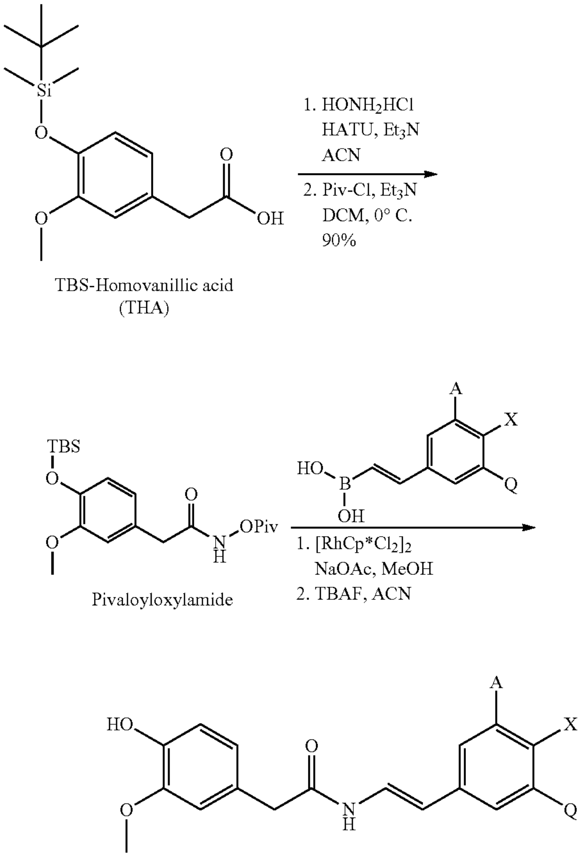

TBS-Homovanillic acid
(THA)

Pivaloyloxylamide

X = Cl, A= H, Q = H, YB-10, 4.1%
X = CF3, A= H, Q = H, YB-11, 4.8%
X = Ph, A= H, Q = H, YB=12, 3.9%
X = OMe, A = H, Q = H, YB-14, 31%
X = H, A = CF3, Q = H, YB-15, 10%
X = H, A = CF3, Q = CF3, YB-22, 15%
X = CN, A = H, Q = H, YB-23, 5%

-continued

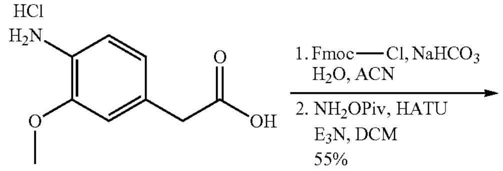

2-(4-amino-3-methoxy phenyl)acetic acid HCl salt

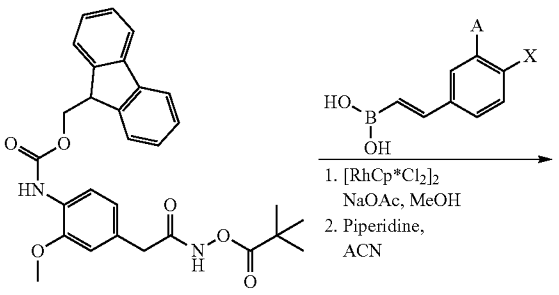

N-pivaloyloxyl amide

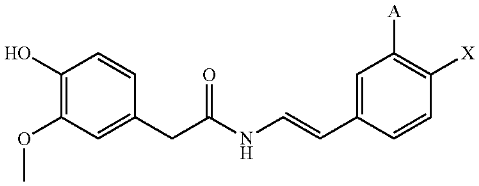

X = CF3, A = H, YB-17, 52%
X = Cl, A = H, YB-18, 63%
X = Ph, A = H, YB-19, 49%
X = OMe, A = H, YB-20, 57%
X = H, A = CF3, YB-21, 52%

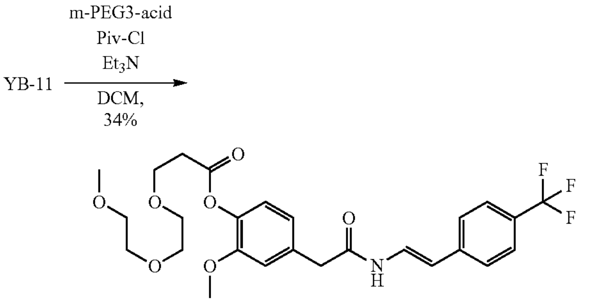

YB-16

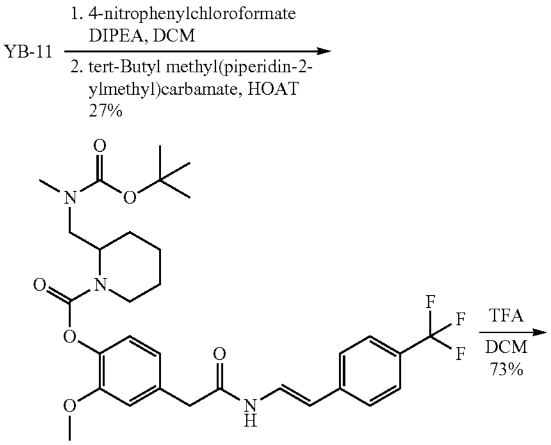

YB-31

-continued

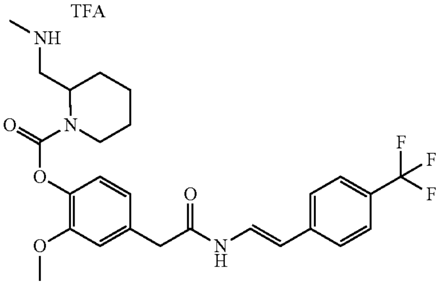

YB-35

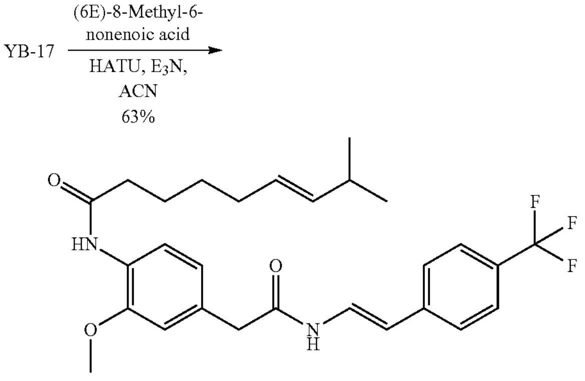

YB-29

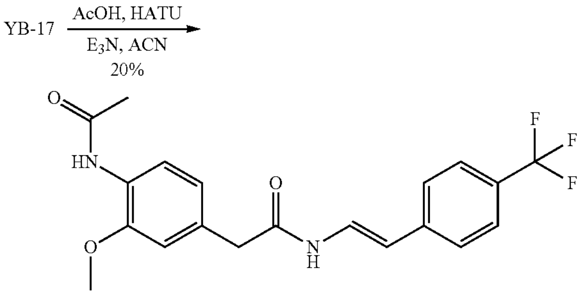

YB-30

4) Research Uses, Formulation and Administration

According to the present invention, the inventive compounds may be assayed in any of the available assays known in the art for identifying compounds having analgesic activity, anti-diabetic activity, anti-obesity activity, anti-cancer activity, TRPV1 activation activity, cancer cell growth inhibition activity, cancer cell invasion inhibition activity and Src activation inhibition activity. For example, the assay may be cellular or non-cellular, in vivo or in vitro, high- or low-throughput format, etc.

Thus, in one aspect, compounds of this invention which are of particular interest include those which have one or more of the following properties:

exhibit activity as TRPV1 activator;

exhibit analgesic effect on pains (e.g., aches and pains of muscles and joints associated with arthritis, post-surgical pain, Morton's Neuroma, backache, cancer pain, strains and sprains, diabetic pain, pain caused by shingles and HIV infection);

are useful for the treatment of Huntington's disease, neuronal affectations such as astrocytomas and mild cognitive impairment;

are useful for the treatment of psoriasis for reduction of itching;

are useful for the treatment of diabetes;

exhibit an apoptosis inducing or antiproliferative effect on cancers;
exhibit activity as cancer cell invasion inhibitor;
exhibit activity as Src protein activation inhibitor;
exhibit an anti-adipogenic effect and are useful for the treatment of obesity; and/or
exhibit a favorable therapeutic profile (e.g., safety, efficacy, solubility, and stability).

As discussed above, certain compounds of this invention as described herein exhibit activity generally as TRPV1 agonist and/or Src activation inhibitor, thus the invention provides a method for treating various central nervous system diseases, diabetes, obesity and cancers. The method involves the administration of a therapeutically effective amount of the compound or pharmaceutically acceptable derivative thereof to a subject including, for example, a mammalian subject, and specifically including a human subject, in need of it. In certain embodiments, the inventive compounds as useful for the treatment of diseases and disorders including, but not limited to aches and pains (e.g., aches and pains of muscles and joints associated with arthritis, post-surgical pain, Morton's Neuroma, backache, cancer pain, strains and sprains, diabetic pain, pain caused by shingles and HIV infection), itching caused by psoriasis, Huntington's disease, neuronal affectations such as astrocytomas and mild cognitive impairment, diabetes, obesity, and cancers, to name a few.

Pharmaceutical Compositions

As discussed above this invention provides novel compounds that have biological properties useful for the treatment of central nervous system diseases, diabetes, obesity and cancers. Accordingly, in another aspect of the present invention, pharmaceutical compositions are provided, which comprise any one of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a prodrug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans or animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. described pharmaceutically acceptable salts in detail in *J. Pharmaceutical Sciences,* 1977, 66, 1, incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hermisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl sulfonate and aryl sulfonate.

Additionally, as used herein, the term "pharmaceutically acceptable ester" refers to esters that hydrolyze in vivo and include those that break down readily in the human or other mammalian body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in humans or animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are transformed within a pharmaceutically acceptable time frame in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

In some embodiments, the compounds described herein, including their pharmaceutically acceptable derivatives, have water solubilities that are greater than the water solubility of capsaicin.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses and Formulations of Compounds of the Invention

As described in more detail herein, in general, the present invention provides compounds useful for the treatment of diseases and disorders including, but not limited to aches and pains (e.g., aches and pains of muscles and joints associated with arthritis, post-surgical pain, Morton's Neuroma, backache, cancer pain, strains and sprains, diabetic pain, pain caused by shingles and HIV infection) (*Curr Anaesth Crit Care* 2008, 19, 338-343; *Molecules,* 2016, 21, 844; *The Cochrane Database of Systematic Reviews* 2017, 1, CD007393). Without wishing to be bound by any particular theory, more generally, the compounds of the invention have been shown to activate TRPV1. TRPV1 activator has demonstrated beneficial effect on pain relief due to its high capacity to open the TRPV1 channel expressed in small-diameter neurons of the dorsal root ganglion (DRG), to increase the intracellular level of calcium and induce membrane depolarization, and to initiate the conformational change and desensitization of TRPV1, and the dysfunctionization of TRPV1-containing nerve terminals in the peripheral tissues (*Mol Pain* 2015, 11, 22; *Physiol Res* 2008, 57 Suppl 3:S59-68; *Arthritis & Rheumatology* 2019, 71, 1524; *Pharmacol Rev.* 2012, 64, 939).

In another aspect of the invention, methods for the treatment of psoriasis for reduction of itching are provided comprising administering a therapeutically effective amount of a compound of formulas (I), (II) and (III), as described herein, to a subject in need thereof.

In other embodiments, compounds of the invention are useful for treating Huntington's disease, reducing ambulatory and stereotypic activity, and increasing the activity (*Brain Res* 2005, 1050, 210).

In other embodiments, compounds of the invention are useful for treating diabetes, insulin resistance and obesity (Cells 2014, 3, 517).

In certain other embodiments, compounds of the invention are useful for treating neuronal affectations such as astrocytomas and mild cognitive impairment (*Nat. Med* 2012, 18, 1232).

In certain other embodiments, compounds of the invention are useful for treating cancer. Without wishing to be bound by any particular theory, more generally, the compounds of the invention have been shown to inhibit the cancer cell growth, inhibit the cancer cell invasion, and block the activation of the Src protein a protein that is key in regulating the proliferation, survival, and motility of the cells (www.medicalnewstoday.com/articles/324911). Phosphorylation activates Src kinase activity, and Src kinase activity regulates proliferation, migration and invasiveness of cancer cells (*Cellular Signalling,* 2012, 24, 1276-1286; *Biochimica et Biophysica Acta,* 2002, 1602, 114-130).

It will be appreciated that the compounds and compositions, according to the method of the present invention, may be administered using any amount and any route of administration effective for the treatment of disease and disorders.

Furthermore, after formulation with an appropriate pharmaceutically acceptable carrier or diluent in a desired dosage, the pharmaceutical compositions of this invention can be administered to humans and other animals intravenously, orally, subcutaneously, rectally, parenterally, intracisternally, intravaginally, intraperitoneally, topically (as by powders, ointments, creams, patches or drops), buccally, as an oral or nasal spray, ocular applications or the like. In certain embodiments, the compounds of the invention may be administered at dosage levels of about 0.001 μg/kg to about 50 mg/kg, from about 0.01 g/kg to about 25 mg/kg, or from about 0.1 μg/kg to about 10 mg/kg of subject body weight per day, one or more times a day, to obtain the desired therapeutic effect. It will also be appreciated that dosages smaller than 0.001 μg/kg or greater than 50 mg/kg (for example 50-100 mg/kg) can be administered to a subject.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, N-methyl-2-pyrrolidone, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly(orthoesters) and poly(anhydrides). Depot injectable formulations are also prepared by entrapping the drug in liposomes or microemulsions, which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions, which can be used, include polymeric substances and waxes.

The present invention encompasses pharmaceutically acceptable topical formulations of inventive compounds. The term "pharmaceutically acceptable topical formulation", as used herein, means any formulation which is pharmaceutically acceptable for intradermal administration of a compound of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allantoin, dimethicone, glycerin, petrolatum, and zinc oxide.

In certain embodiments, the pharmaceutically acceptable topical formulations of the invention comprise at least a compound of the invention and a penetration enhancing agent. The choice of topical formulation will depend on several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methyl pyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmitoleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

In certain embodiments, after application of the topical formulation to the epidermis, the area may be covered with a dressing. The term "dressing", as used herein, means a covering designed to protect a topically applied drug formulation. "Dressing" includes coverings such as a bandage, which may be porous or non-porous and various inert coverings, e.g., a plastic film wrap or other non-absorbent film. The term "dressing" also encompasses non-woven or woven coverings, particularly elastomeric coverings, which allow for heat and vapor transport. These dressings allow for cooling of the treated area, which provides for greater comfort.

In certain exemplary embodiments, pharmaceutically acceptable topical formulations of the invention are contained in a patch that is applied adjacent to the area of skin to be treated. As used herein a "patch" comprises at least a topical formulation and a covering layer, such that, the patch can be placed over the area of skin to be treated. Preferably, but not necessarily, the patch is designed to maximize drug delivery through the stratum corneum and into the epidermis or dermis, reduce lag time, promote uniform absorption, and/or reduce mechanical rub-off. In certain embodiments, when the intended use comprises the treatment of a skin condition (e.g., psoriasis), the patch is designed to minimize absorption into the circulatory system. Preferably, the patch components resemble the viscoelastic properties of the skin and conform to the skin during movement to prevent undue shear and delamination. Advantages of a patch comprising the topical formulation of the invention over conventional methods of administration include (i) that the dose is controlled by the patch's surface area, (ii) constant rate of administration, (iii) longer duration of action (the ability of to adhere to the skin for 1, 3, 7 days or longer), (iv) improved patient compliance, (v) non-invasive dosing, and (vi) reversible action (i.e., the patch can simply be removed).

In certain embodiments, a patch suitable for use with the invention contains at least: (1) a backing layer and (2) a carrier formulated with a compound of the invention. Examples of patch systems suitable for practicing the invention include, but are not limited to, matrix-type patches; reservoir-type patches; multi-laminate drug-in-adhesive-type patches; and monolithic drug-in-adhesive type-patch. See, for example Ghosh, T. K.; Pfister, W. R.; Yum, S. I. Transdermal and Topical Drug Delivery Systems, Interpharm Press, Inc. p. 249-297, which is incorporated herein by reference in its entirety. These patches are well known in the art and generally available commercially.

The matrix patch comprises matrix containing an inventive compound, an adhesive backing film overlay, and preferably, but not necessarily, a release liner. In some cases, it may be necessary to include an impermeable layer to minimize drug migration into the backing film (e.g., U.S. Pat. No. 4,336,243, incorporated herein by reference). In certain embodiments, the matrix containing the inventive compound is held against the skin by the adhesive overlay. Examples of suitable matrix materials include but are not limited to lipophilic polymers, such as polyvinyl chloride, polydimethylsiloxane, and hydrophilic polymers like polyvinylpyrrolidone, polyvinyl alcohol, hydrogels based on gelatin, or polyvinylpyrrolidone/polyethylene oxide mixtures. Suitable release liners include but are not limited to occlusive, opaque, or clear polyester films with a thin coating of pressure sensitive release liner (e.g., silicone, fluorsilicone, and perfluorocarbon based polymers).

The reservoir type patch design is characterized by a backing film coated with an adhesive, and a reservoir compartment comprising a drug formulation preferably, in the form of a solution or suspension, that is separated from the skin by a semipermeable membrane (e.g., U.S. Pat. No. 4,615,699, incorporated herein by reference). The adhesive coated backing layer reservoir adjacent to the skin.

The monolithic drug-in-adhesive patch design is characterized by the inclusion of the drug formulation in the skin contacting adhesive layer, a backing film and preferably, a release liner. The adhesive functions both to release the compound and adhere the compound matrix to the skin. The drug-in-adhesive system does not require an adhesive overlay and thus the patch size is minimized. Also, drug-in-adhesive type patches are thin and comfortable (e.g., U.S. Pat. No. 4,751,087, incorporated herein by reference).

The multi-laminate drug-in-adhesive patch design further incorporates an additional semi-permeable membrane between two distinct drug-in-adhesive layers or multiple drug-in-adhesive layers under a single backing film.

Semi permeable membranes, useful with the reservoir or multi-laminate patch, include thin non-porous ethylene vinyl acetate films or thin microporous films of polyethylene employed in microlaminate solid state reservoir patches.

Adhesives for use with the drug-in-adhesive type patches are well known in the art and a practitioner skilled in the relevant art would know how to select an adhesive suitable for the intended use. Examples of adhesives include, but are not limited to, polyisobutylenes, silicones, and acrylics. Preferably, adhesives can function under a wide range of conditions, such as, high and low humidity, bathing, sweating etc. Preferably the adhesive is a composition based on natural or synthetic rubber; a polyacrylate such as polybutylacrylate, polymethylacrylate, poly-2-ethylhexyl acrylate; polyvinylacetate; polydimethylsiloxane; pressure sensitive acrylic adhesives, for example Durotak® adhesives (e.g., Durotak® 2052, National Starch and Chemicals) or hydrogels (e.g., high molecular weight polyvinylpyrrolidone and oligomeric polyethylene oxide). The adhesive may contain a thickener, such as a silica thickener (e.g., Aerosil, Degussa, Ridgefield Park, N.J.) or a crosslinker such as, aluminum acetylacetonate.

Backing films may be occlusive or permeable and may be derived from synthetic polymers like polyolefin, polyester, polyethylene, polyvinylidene chloride, and polyurethane or from natural materials like cotton, wool, etc. Occlusive backing films, such as synthetic polyesters, result in hydration of the outer layers of the stratum corneum while non-occlusive backings allow the area to breath (i.e., promote water vapor transmission from the skin surface).

Selection of the appropriate dosage for the application site is an important consideration. The rate of compound intradermal administration from the topical formulation or patch is a function of skin permeability, and skin permeability has been shown to vary between anatomical sites depending on the thickness of the stratum corneum. For example, the permeability, in general, increases in order from planter foot arch, lateral ankle, palm, ventral forearm, dorsal forearm, back, chest, thigh, abdomen, scalp, axilla, forehead, and scrotum (Wester, R. C. and Maibach, H. I. (1989) Regional variation in Percutaneous Absorption: In Percutaneous Absorption, Mechanism, Methodology, Drug Delivery, 2nd ed., Eds. R. L. Bronaugh and H. I. Maibach, Marcel Dekker, Inc., New York, pp. 111-119 (incorporated herein by reference)). Typically, the dosages and dosing frequency will be determined by a trained medical professional.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent useful for the treatment of central nervous system disease, anticancer agent or agent useful for the treatment of obesity or diabetes), or they may achieve different effects (e.g., control of any adverse effects).

Also encompassed by the present invention are kits for conveniently and effectively carrying out the methods in accordance with the present invention. In general, the pharmaceutical pack or kit comprises one or more containers filled with one or more of the ingredients comprising the pharmaceutical compositions of the invention. Such kits are especially suited for the delivery of solid oral forms such as tablets or capsules. Such a kit preferably includes a number of unit dosages, and may also include a card having the dosages oriented in the order of their intended numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXAMPLES

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

General Description of Synthetic Methods:

The practitioner has a well-established literature of synthetic chemistry to draw upon, in combination with the information contained herein, for guidance on synthetic strategies, protecting groups, and other materials and methods useful for the synthesis of the compounds of this invention.

The various references cited herein provide helpful background information on preparing compounds similar to the inventive compounds described herein or relevant intermediates, as well as information on formulation, uses, and administration of such compounds which may be of interest.

Moreover, the practitioner is directed to the specific guidance and examples provided in this document relating to various exemplary compounds and intermediates thereof.

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive compounds or compositions including them. For example, a variety of solution phase synthetic methods such as those discussed in detail below may be used. Alternatively, or additionally, the inventive compounds may be prepared using any of a variety of combinatorial techniques, parallel synthesis and/or solid phase synthetic methods known in the art.

It will be appreciated as described below, that a variety of inventive compounds can be synthesized according to the methods described herein. The starting materials and reagents used in preparing these compounds are either available from commercial suppliers such as Fisher Scientific (Waltham, MA), MilliporeSigma (St. Louis, MO), or are prepared by methods well known to a person of ordinary skill in the art following procedures described in such references as Fieser and Fieser 1991, "Reagents for Organic Synthesis", vols 1-17, John Wiley and Sons, New York, NY, 1991; Rodd 1989 "Chemistry of Carbon Compounds", vols. 1-5 and supps, Elsevier Science Publishers, 1989; "Organic Reactions", vols 1-40, John Wiley and Sons, New York, NY, 1991; March 2001, "Advanced Organic Chemistry", 5th ed. John Wiley and Sons, New York, NY; and Larock 1990, "Comprehensive Organic Transformations: A Guide to Functional Group Preparations", 2nd ed. VCH Publishers. These schemes are merely illustrative of some methods by which the inventive compounds can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

Certain exemplary compounds of the invention and capsaicin are listed below and are referred to by compound number as indicated.

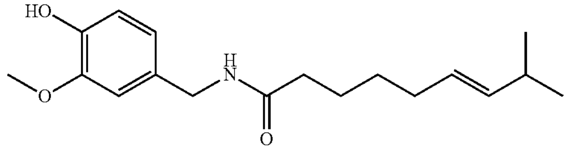

Capsaicin

-continued

YB-1

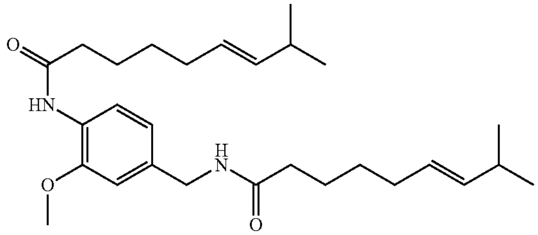

YB-2

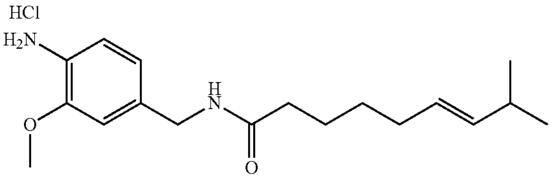

YB-3

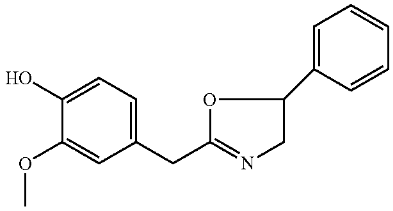

YB-4

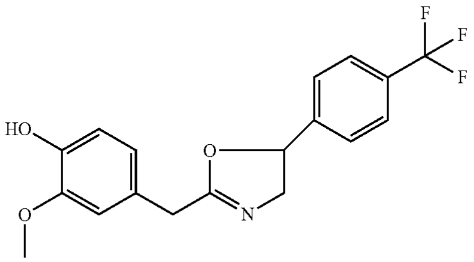

YB-5

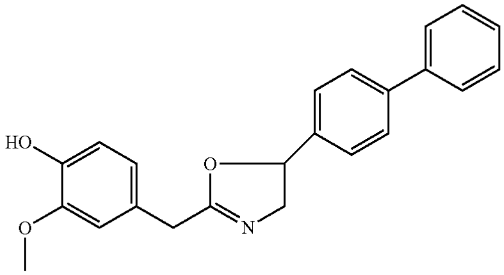

YB-6

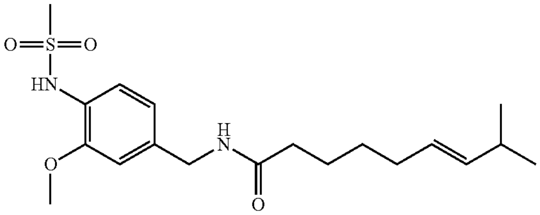

-continued
YB-7
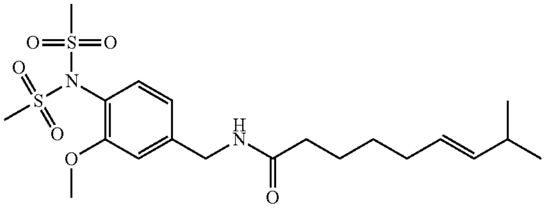
YB-8
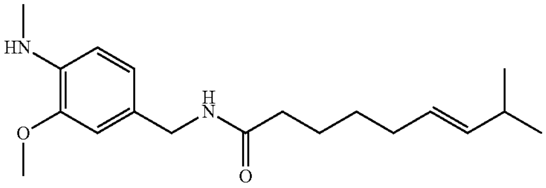
YB-9
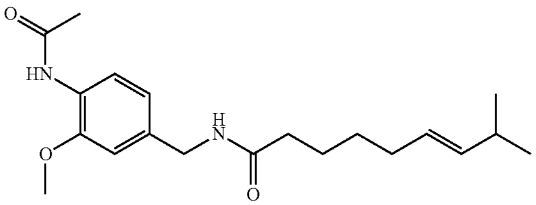
YB-10
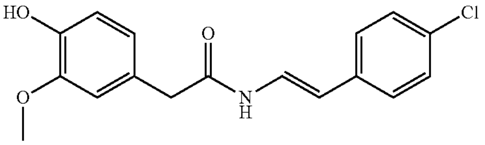
YB-11
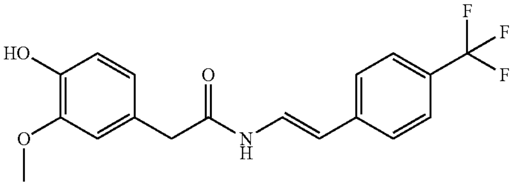
YB-12
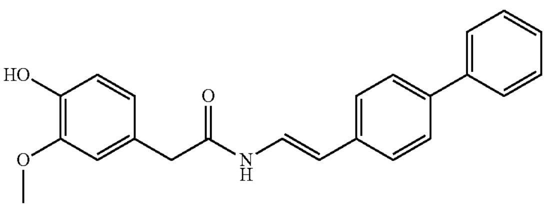
YB-13
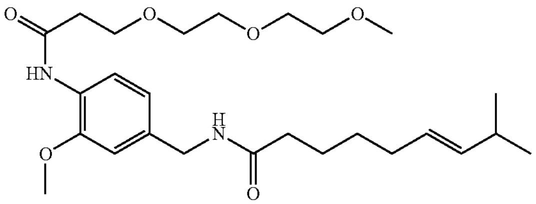
-continued
YB-14
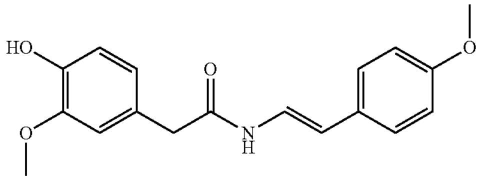
YB-15
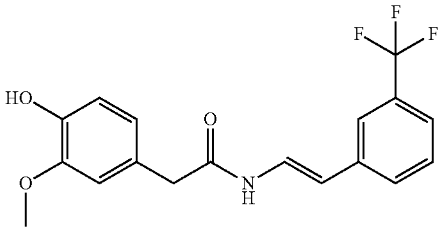
YB-16
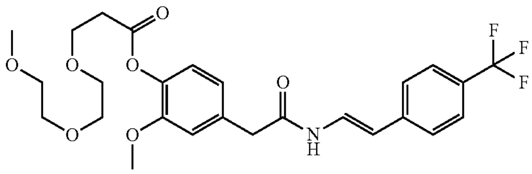
YB-17
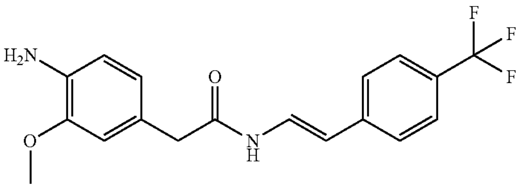
YB-18
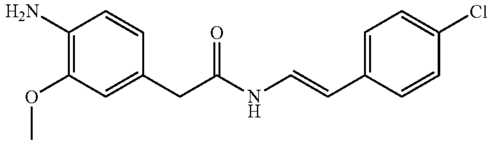
YB-19
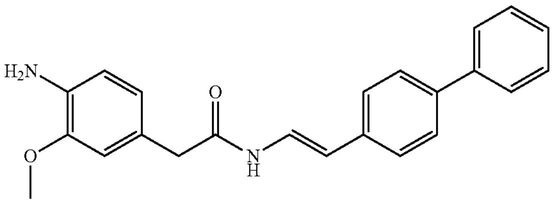
YB-20
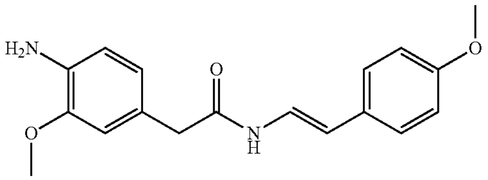

-continued

YB-21

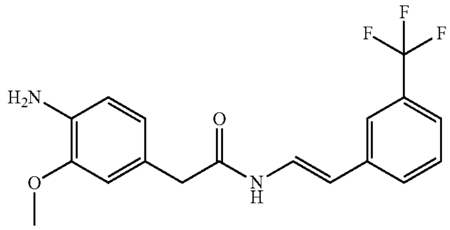

YB-22

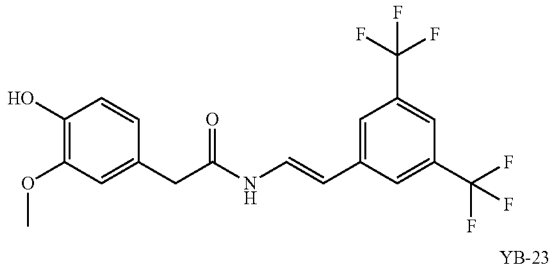

YB-23

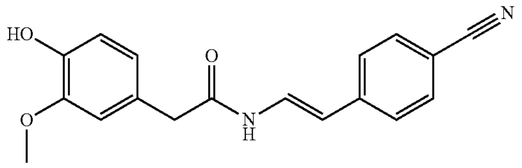

YB-29

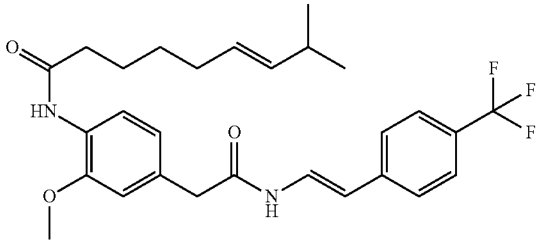

YB-30

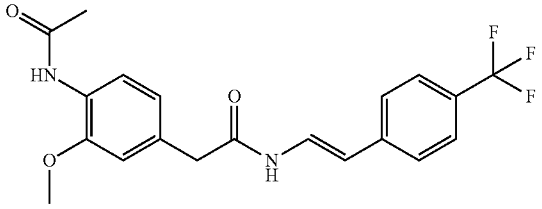

YB-31

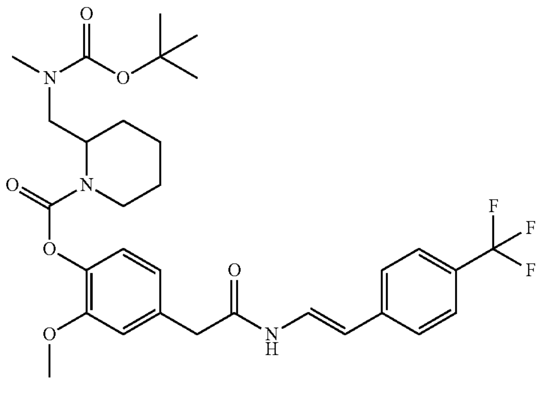

-continued

YB-35

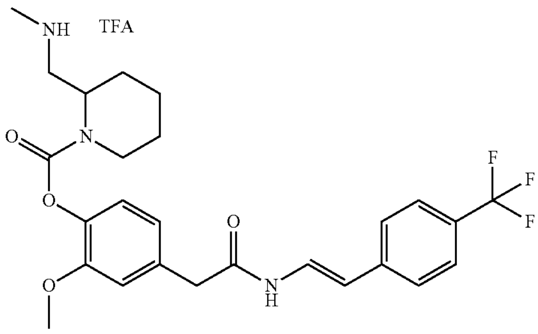

General Reaction Procedures:

Unless mentioned specifically, reaction mixtures were stirred using a magnetically driven stirrer bar. An inert atmosphere refers to either dry argon or dry nitrogen. Reactions were monitored either by thin layer chromatography, by proton nuclear magnetic resonance (NMR) or by high-pressure liquid chromatography (HPLC), of a suitably worked up sample of the reaction mixture.

Listed below are abbreviations used for some common organic reagents referred to herein:

AcOH: Acetic acid
ACN: Acetonitrile
$Boc_2O$: Boc anhydride (Di-tert-butyl dicarbonate)
$CHCl_3$: Chloroform
DCM: Dichloromethane
DIPEA: N,N-Diisopropylethylamine
DBU: 1,8-Diazabicyclo[5.4.0]undec-7-ene
EtOAc: Ethyl acetate
Fmoc-Cl: 9-Fluorenylmethoxycarbonyl chloride
HATU: Hexafluorophosphate Azabenzotriazole Tetramethyl Uronium
HOAt: 1-Hydroxy-7-azabenzotriazole
HCl: Hydrochloric acid
NaOAc: Sodium acetate
$NaHCO_3$: Sodium bicarbonate
$Na_2SO_4$: Sodium sulfate
m-PEG3-acid: 3-[2-(2-Methoxyethoxy)ethoxy]propanoic acid
Piv-Cl: Pivaloyl chloride
$[RhCp^*Cl_2]_2$: Pentamethylcyclopentadienyl rhodium dichloride
TBAF: Tetrabutylammonium fluoride
$Et_3N$: Triethylamine
TBS-Cl (TBDMS-Cl): tert-Butyldimethylsilyl chloride
TFA: Trifluoroacetic acid
THF: Tetrahydrofuran
MsCl: Methanesulfonyl chloride General Work Up Procedures:

Unless mentioned specifically, reaction mixtures were cooled to rt (room temperature) or below then quenched, when necessary, with either water or a saturated aqueous solution of ammonium chloride. Desired products were extracted by partitioning between water and a suitable water-immiscible solvent (e.g. ethyl acetate, dichloromethane, diethyl ether). The desired product containing extracts were washed appropriately with water followed by a saturated solution of brine. On occasions where the product containing extract was deemed to contain residual oxidants, the extract was washed with a 10% solution of sodium sulfite in saturated aqueous sodium bicarbonate solution, prior to the aforementioned washing procedure. On occasions where the product containing extract was deemed to contain residual acids, the extract was washed with saturated aqueous sodium bicarbonate solution, prior to the aforementioned washing procedure (except in those cases where the desired product itself had acidic character). On occasions where the product containing extract was deemed to contain residual bases, the extract was washed with 10% aqueous citric acid solution, prior to the aforementioned washing procedure (except in those cases where the desired product itself had basic character). Post washing, the desired product containing extracts were dried over anhydrous sodium sulfate, and then filtered. The crude products were then isolated by removal of solvent(s) by rotary evaporation under reduced pressure, at an appropriate temperature (generally less than 45° C.).

General Purification Procedures:

Unless mentioned specifically, chromatographic purification refers to flash column chromatography on silica (Silica gel 0.200-0.500 mm, 60 Å from Acros), using a single solvent or mixed solvent as eluent. Suitably purified desired product containing elutes were combined and concentrated under reduced pressure at an appropriate temperature (generally less than 45° C.) to constant mass. Final compounds were dissolved in 50% aqueous acetonitrile, filtered and transferred to vials, then freeze-dried under high vacuum before submission for biological testing.

Rigor, Reproducibility and Statistics:

Chemical analysis and solubility tests were performed blind to the identity of the samples. Intermediates and final analogs were analyzed by NMR (JEOL 400 MHz NMR) and HPLC/MS (Waters Acquity UPLC with SQD Mass Spec) to confirm structures and purity. Final compounds were purified to achieve >95% purity based on HPLC analysis.

For behavioral and in vitro cell-based experiments, experiments were designed with the UK 3R's Experimental Design Assistant freeware to maximize rigor and reproducibility (*PLoS biology* 2017, 15:e2003779). Experiments were completed and analyzed, blinded to group assignment (i.e., treatment or control). Statistical significance for all data was calculated via t-tests, 1-way ANOVA, or 2-way ANOVA with appropriate Bonferroni post-hoc tests. P values <0.05 was considered statistically significant. Equal cohorts of male and female animals were used.

Example 1: Procedure of the Preparation of YB-1 and YB-2

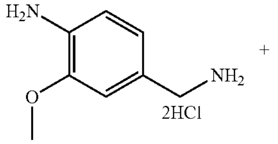

4-(aminomethyl)-2-methoxy aniline dihydrochloride

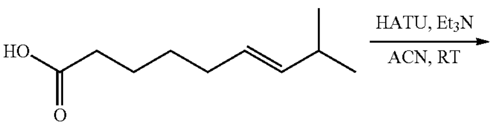

(6E)-8-Methyl-6-nonenoic acid

-continued

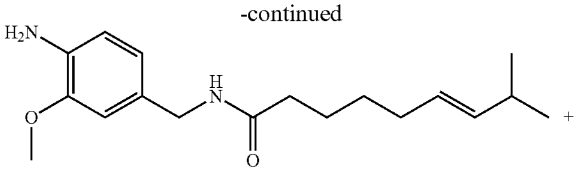

YB-2
44%

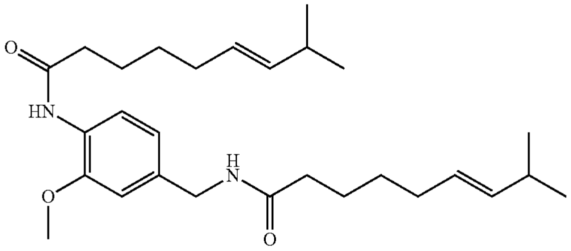

YB-1
17%

A mixture of (6E)-8-methyl-6-nonenoic acid (10 mg, 0.059 mmol; Order Number LN01303052 from LabNetwork), 4-(aminomethyl)-2-methoxyaniline dihydrochloride (13 mg, 0.059 mmol; Order Number EN300-1721327 from Enamine) in ACN (0.5 mL) was treated with $Et_3N$ (26 uL, 0.19 mmol) and HATU (24 mg, 0.062 mmol) at rt for 0.5 h, then quenched with aq. $NaHCO_3$. The mixture was vigorously stirred at rt for 15 min, then diluted with EtOAc (3 mL) and $H_2O$ (3 mL). The organic phase was separated, and the aqueous phase was extracted with EtOAc (1 mL). The combined organics were dried ($Na_2SO_4$) and concentrated to give a crude brown oil, which was purified by chromatography (2:1 EtOAc/Hexane) to afford 4.7 mg of YB-1 (0.010 mmol, 17%), $R_f$ 0.42 (2:1 EtOAc/Hexane) and 7.9 mg of YB-2 (0.026 mmol, 44%), $R_f$ 0.33 (2:1 EtOAc/Hexane).

YB-1 $^1$H-NMR (400 MHz, $CDCl_3$) δ 8.32 (d, J=8.0 Hz, 1H, ArH), 7.71 (s, 1H, ArH), 6.83 (d, J=9.8 Hz, 1H, ArH), 6.82 (s, 1H, Amide NH), 5.70 (s, 1H, amide NH), 5.19-5.39 (m, 4H, olefin Hs), 4.38 (d, J=5.5 Hz, 2H, ArCH2NH), 3.86 (s, 3H, ArOCH3), 2.38 (t, J=7.3 Hz, 2H, alkyl Hs), 2.18-2.24 (m, 4H, alkyl Hs), 1.95-2.04 (m, 4H, alkyl Hs), 1.63-1.76 (m, 4H, alkyl Hs), 1.24-1.47 (m, 4H, alkyl Hs), 0.92-0.96 (m, 12H, alkyl CH3). MS m/e 457 ($M^+$+H).

YB-2 $^1$H-NMR (400 MHz, $CDCl_3$) δ 6.63-6.71 (m, 3H, ArH), 5.62 (s, 1H, amide NH), 5.28-5.39 (m, 2H, olefin Hs), 4.31-4.32 (m, 2H, ArCH2NH), 4.11 (br s, 1H, amine NH2), 3.83 (s, 3H, ArOCH3), 3.82 (br s, 1H, amine NH2), 2.16-2.23 (m, 3H, alkyl Hs), 2.03-2.06 (m, 1H, alkyl Hs), 1.95-2.00 (m, 1H, alkyl Hs), 1.60-1.68 (m, 2H, alkyl Hs), 1.33-1.41 (m, 2H, alkyl Hs), 0.91-0.95 (m, 6H, alkyl CH3). MS m/e 305 ($M^+$+H).

Example 2: Modified Procedure of the Preparation of YB-2

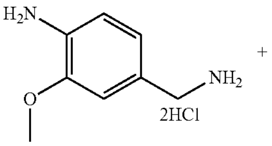

4-(aminomethyl)-2-methoxyaniline dihydrochloride

-continued

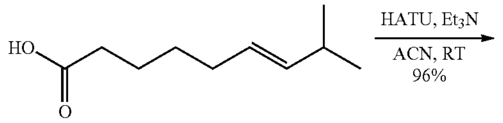

(6E)-8-Methyl-6-nonenoic acid

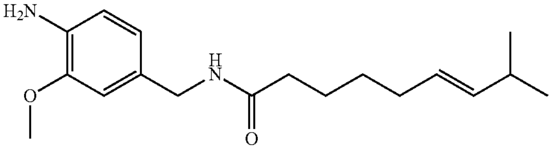

YB-2

A mixture of (6E)-8-methyl-6-nonenoic acid (0.10 g, 0.59 mmol; Order Number LN01303052 from LabNetwork), 4-(aminomethyl)-2-methoxyaniline dihydrochloride (0.14 g, 0.65 mmol; Order Number EN300-1721327 from Enamine) in ACN (5 mL) was treated with $Et_3N$ (0.26 mL, 1.9 mmol) and HATU (0.24 g, 0.62 mmol) at 0° C. for 20 min, then quenched with aq. $NaHCO_3$. The mixture was vigorously stirred at rt for 15 min, then diluted with DCM (25 mL) and $H_2O$ (20 mL). The organic phase was separated, and the aqueous phase was extracted with DCM (10 mL). The combined organics were dried ($Na_2SO_4$) and concentrated to give a crude oil, which was purified by chromatography (2:1 EtOAc/Hexane) to afford 0.17 g of YB-2 (0.57 mmol, 96%), $R_f$ 0.33 (2:1 EtOAc/Hexane). NMR and MS data same as YB-2 from the previous procedure in Example 1.

Example 3: Procedure of the Preparation of YB-3

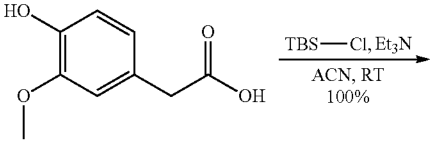

Homovanillic acid

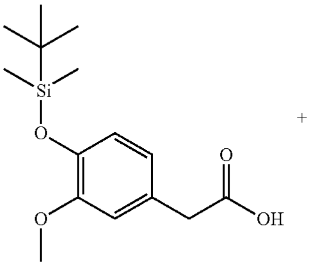

+

TBS-Homovanillic acid

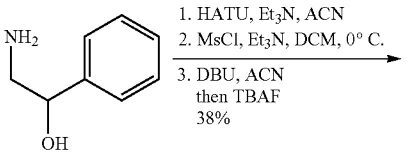

2-amino-1-phenylethan-1-ol

-continued

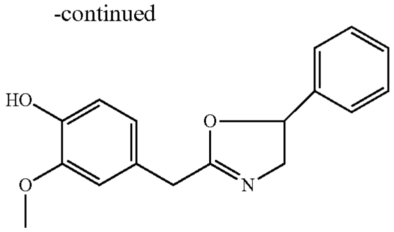

YB-3

$Et_3N$ (0.54 mL, 3.9 mmol) was added dropwise to a mixture of the Homovanillic acid (0.20 g, 1.1 mmol; Order Number EN300-179380 from Enamine) and TBDMS-Cl (0.36 g, 2.4 mmol) in ACN (5 mL) at rt. The resulting mixture was stirred vigorously at rt for 12 h, then quenched with MeOH (0.44 mL, 11 mmol). The solution was stirred at rt for 10 min, then concentrated. The residue was stirred in EtOAc (10 mL) at 0° C., and added 0.3N HCl (11 mL, 3.3 mmol). The mixture was stirred vigorously at rt for 1.5 h. The organic layer was separated, and the aqueous layer was extracted with EtOAc (5 mL). The combined organics were dried ($Na_2SO_4$) and concentrated to give 0.33 g of TBS-Homovanillic acid (1.1 mmol, 100%), which was carried into the next step without purification, $R_f$=0.50 (2:1 EtOAc/Hexane).

$Et_3N$ (18 uL, 0.13 mmol) was added dropwise to a mixture of crude TBS-Homovanillic acid (33 mg, 0.11 mmol), 2-amino-1-phenylethan-1-ol (16 mg, 0.12 mmol; Order Number EN300-19918 from Enamine) and HATU (45 mg, 0.12 mmol) in ACN (1 mL) at rt. The mixture was stirred at rt for 20 min, then quenched with aq. $NaHCO_3$. The mixture was vigorously stirred at rt for 15 min, then diluted with DCM (5 mL) and $H_2O$ (2 mL). After separation, the aqueous layer was extracted with DCM (2 mL). The combined organics were dried ($Na_2SO_4$) and concentrated to give 46 mg of alcohol intermediate (0.11 mmol, 100%).

Crude alcohol intermediate (46 mg, 0.11 mmol) in DCM (2 mL) was treated with $Et_3N$ (39 uL, 0.28 mmol) and MsCl (17 uL, 0.22 mmol) at 0° C. for 10 min, then quenched with aq. $NaHCO_3$. The mixture was vigorously stirred at rt for 30 min, then diluted with DCM (3 mL). After separation, the aqueous layer was extracted with DCM (2 mL). The combined organics were dried ($Na_2SO_4$) and concentrated to give 54 mg of mesylate intermediate (0.11 mmol, 100%).

Crude Mesylate (54 mg, 0.11 mmol) in 1 mL of ACN was treated with DBU (33 uL, 0.22 mmol) for 10 min, followed by TBAF, 70-75% in water (79 mg, 0.22 mmol) for 20 min. The mixture was quenched with pH 7 buffer (1 mL) and 1N HCl (0.22 mL, 0.22 mmol) at 0° C., then diluted with EtOAc (4 mL) and $H_2O$ (2 mL). After separation, the aqueous layer was extracted with EtOAc (2 mL). The combined organics were dried ($Na_2SO_4$) and concentrated to give a crude oil, which was purified by chromatography (2:3 EtOAc/Hexane) to afford 12 mg of YB-3 (0.042 mmol, 38%), $R_f$ 0.09 (2:3 EtOAc/Hexane).

$^1$H-NMR (400 MHz, CDCl3) δ 7.25-7.31 (m, 5H, phenyl ArH), 6.84 (d, J=8.0 Hz, 1H, vanillyl ArH), 6.68 (s, 1H, vanillyl ArH), 6.65 (d, J=8.0 Hz, 1H, vanillyl ArH), 5.86 (m, 1H, oxazoline), 4.78 (dd, J=7.3, 3.2 Hz, 1H, oxazoline), 3.84 (s, 3H, ArOCH3), 3.82 (m, 1H, oxazoline), 3.48 (s, 2H, ArCH2CO). MS m/e 284 ($M^+$+H).

Example 4: Procedure of the Preparation of YB-4

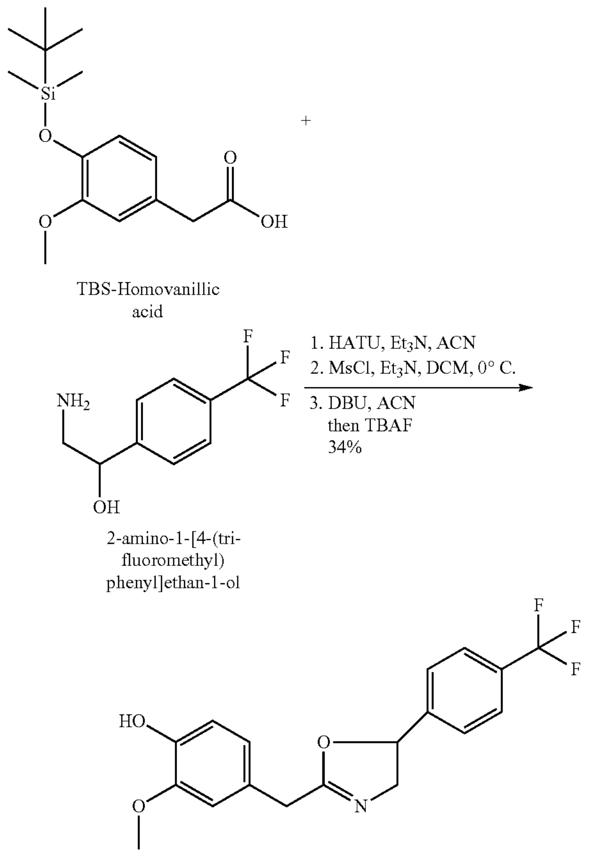

TBS-Homovanillic acid 2-amino-1-[4-(trifluoromethyl)phenyl]ethan-1-ol

YB-4

$Et_3N$ (18 uL, 0.13 mmol) was added dropwise to a mixture of crude TBS-Homovanillic acid (33 mg, 0.11 mmol), 2-amino-1-[4-(trifluoromethyl)phenyl]ethan-1-ol (25 mg, 0.12 mmol; Order Number EN300-42624 from Enamine) and HATU (45 mg, 0.12 mmol) in ACN (1 mL) at rt. The mixture was stirred at rt for 20 min, then quenched with aq. $NaHCO_3$. The mixture was vigorously stirred at rt for 15 min, then diluted with DCM (5 mL) and $H_2O$ (2 mL). After separation, the aqueous layer was extracted with DCM (2 mL). The combined organics were dried ($Na_2SO4$) and concentrated to give 53 mg of alcohol intermediate (0.11 mmol, 100%).

Crude alcohol intermediate (53 mg, 0.11 mmol) in DCM (2 mL) was treated with $Et_3N$ (39 uL, 0.28 mmol) and MsCl (17 uL, 0.22 mmol) at 0° C. for 10 min, then quenched with aq. $NaHCO_3$. The mixture was vigorously stirred at rt for 30 min, then diluted with DCM (3 mL). After separation, the aqueous layer was extracted with DCM (2 mL). The combined organics were dried ($Na_2SO_4$) and concentrated to give 62 mg of mesylate intermediate (0.11 mmol, 100%).

Crude Mesylate (62 mg, 0.11 mmol) in 1 mL of ACN was treated with DBU (33 uL, 0.22 mmol) for 10 min, followed by TBAF, 70-75% in water (79 mg, 0.22 mmol) for 20 min. The mixture was quenched with pH 7 buffer (1 mL) and 1N HCl (0.22 mL, 0.22 mmol) at 0° C., then diluted with EtOAc (4 mL) and $H_2O$ (2 mL). After separation, the aqueous layer was extracted with EtOAc (2 mL). The combined organics were dried ($Na_2SO_4$) and concentrated to give a crude oil, which was purified by chromatography (2:1 EtOAc/Hexane) to afford 13 mg of YB-4 (0.037 mmol, 34%), $R_f$ 0.33 (2:1 EtOAc/Hexane).

$^1$H-NMR (400 MHz, $CDCl_3$) δ 7.57 (d, J=8.2 Hz, 2H, CF3-ArHs), 7.26 (d, J=8.2 Hz, 2H, CF3-ArHs), 6.84-6.89 (m, 3H, vanillyl ArHs), 5.52 (dd, J=10.2, 7.7 Hz, 1H, oxazoline), 4.31 (dd, J=14.4, 10.3 Hz, 1H, oxazoline), 3.84 (s, 3H, ArOCH3), 3.73 (q, J=7.2 Hz, 1H, oxazoline), 3.64 (s, 2H, ArCH2CO). MS m/e 352 ($M^+$+H).

Example 5: Procedure of the Preparation of YB-5

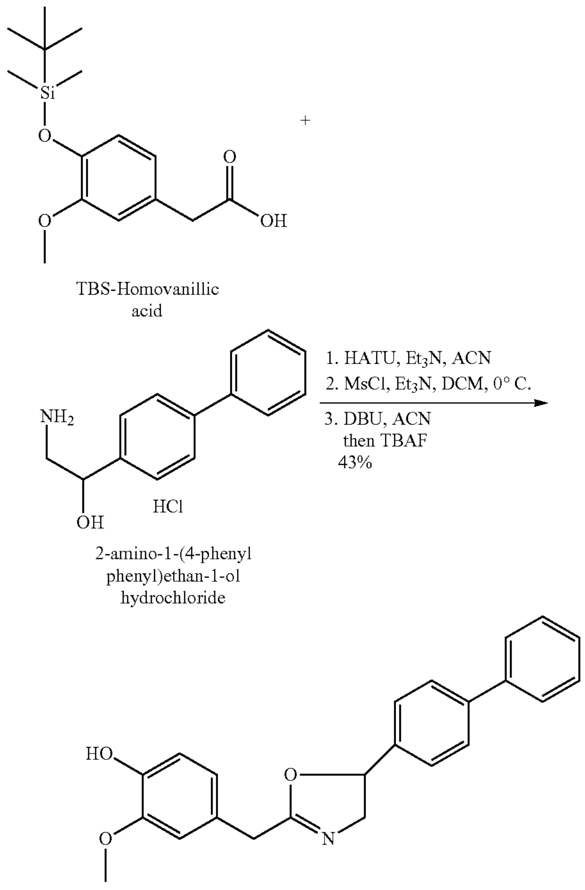

TBS-Homovanillic acid

HCl 2-amino-1-(4-phenylphenyl)ethan-1-ol hydrochloride

YB-5

$Et_3N$ (18 uL, 0.13 mmol) was added dropwise to a mixture of crude TBS-Homovanillic acid (33 mg, 0.11 mmol), 2-amino-1-(4-phenylphenyl)ethan-1-ol hydrochloride (30 mg, 0.12 mmol; Order Number EN300-139453 from Enamine) and HATU (45 mg, 0.12 mmol) in ACN (1 mL) at rt. The mixture was stirred at rt for 20 min, then quenched with aq. $NaHCO_3$. The mixture was vigorously stirred at rt for 15 min, then diluted with DCM (5 mL) and $H_2O$ (2 mL). After separation, the aqueous layer was extracted with DCM (2 mL). The combined organics were dried ($Na_2SO_4$) and concentrated to give 54 mg of alcohol intermediate (0.11 mmol, 100%).

Crude alcohol intermediate (54 mg, 0.11 mmol) in DCM (2 mL) was treated with $Et_3N$ (39 uL, 0.28 mmol) and MsCl (17 uL, 0.22 mmol) at 0° C. for 10 min, then quenched with aq. $NaHCO_3$. The mixture was vigorously stirred at rt for 30 min, then diluted with DCM (3 mL). After separation, the aqueous layer was extracted with DCM (2 mL). The combined organics were dried ($Na_2SO_4$) and concentrated to give 63 mg of mesylate intermediate (0.11 mmol, 100%).

Crude Mesylate (63 mg, 0.11 mmol) in 1 mL of ACN was treated with DBU (33 uL, 0.22 mmol) for 10 min, followed by TBAF, 70-75% in water (79 mg, 0.22 mmol) for 20 min. The mixture was quenched with pH 7 buffer (1 mL) and 1N HCl (0.22 mL, 0.22 mmol) at 0° C., then diluted with EtOAc (4 mL) and $H_2O$ (2 mL). After separation, the aqueous layer was extracted with EtOAc (2 mL). The combined organics were dried ($Na_2SO_4$) and concentrated to give a crude oil, which was purified by chromatography (EtOAc) to afford 17 mg of YB-5 (0.047 mmol, 43%), $R_f$ 0.40 (EtOAc).

$^1$H-NMR (400 MHz, $CDCl_3$) δ 7.53-7.58 (m, 4H, ArHs), 7.43 (t, J=7.5 Hz, 2H, ArHs), 7.34 (t, J=7.3 Hz, 1H, ArHs), 7.24-7.26 (m, 2H, ArHs), 6.83-6.88 (m, 3H, vanillyl ArHs), 5.50 (dd, J=10.1, 7.8 Hz, 1H, oxazoline), 4.28 (dd, J=14.2, 10.3 Hz, 1H, oxazoline), 3.83 (s, 3H, ArOCH3), 3.80 (t, 1H, J=7.4 Hz, oxazoline), 3.64 (s, 2H, ArCH2CO). MS m/e 360 ($M^+$+H).

Example 6: Procedure of the Preparation of YB-6 and YB-7

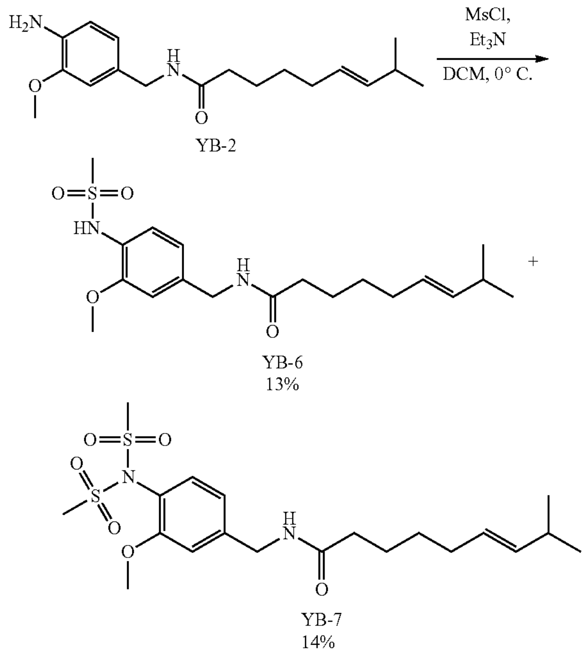

YB-2

+

YB-6
13%

YB-7
14%

A solution of YB-2 (23 mg, 0.076 mmol) and $Et_3N$ (26 uL, 0.19 mmol) in DCM (1 mL) at 0° C. was treated with MsCl (12 uL, 0.15 mmol) for 10 min, then quenched with aq. $NaHCO_3$. The mixture was vigorously stirred at rt for 30 min, then diluted with DCM (3 mL). After separation, the aqueous layer was extracted with DCM (2 mL). The combined organics were dried ($Na_2SO_4$) and concentrated to give a crude oil, which was purified by chromatography (2:1 EtOAc/Hexane) to provide 3.9 mg of YB-6 (0.010 mmol, 13%), $R_f$ 0.26 (2:1 EtOAc/Hexane) and 5.0 mg of YB-7 (0.011 mmol, 14%), $R_f$0.46 (2:1 EtOAc/Hexane).

YB-6 $^1$H-NMR (400 MHz, $CDCl_3$) δ 7.46 (d, J=8.5 Hz, 1H, ArH), 6.86 (d, J=7.3 Hz, 2H, ArH), 6.74 (s, 1H, MeSO2NH), 5.74 (s, 1H, amide NH), 5.19-5.40 (m, 2H, olefin Hs), 4.41 (d, J=6.0 Hz, 2H, ArCH2N), 3.87 (s, 3H, ArOCH3), 2.95 (s, 3H, MeSO2N), 2.17-2.26 (m, 3H, alkyl Hs), 1.96-2.03 (m, 2H, alkyl Hs), 1.62-1.70 (m, 2H, alkyl Hs), 1.35-1.45 (m, 2H, alkyl Hs), 0.95 (d, J=6.8 Hz, 6H, alkyl CH3). MS m/e 383 ($M^+$+H).

YB-7 $^1$H-NMR (400 MHz, $CDCl_3$) δ 7.23 (d, J=8.0 Hz, 1H, ArH), 6.95 (s, 1H, ArH), 6.91 (d, J=8.0 Hz, 1H, ArH), 5.73 (s, 1H, amide NH), 5.19-5.41 (m, 2H, olefin Hs), 4.46 (d, J=5.7 Hz, 2H, ArCH2N), 3.90 (s, 3H, ArOCH3), 3.42 (s, 6H, MeSO2N), 2.14-2.25 (m, 3H, alkyl Hs), 1.97-2.07 (m, 2H, alkyl Hs), 1.63-1.71 (m, 2H, alkyl Hs), 1.34-1.43 (m, 2H, alkyl Hs), 0.95 (d, J=6.8 Hz, 6H, alkyl CH3). MS m/e 461 ($M^+$+H).

Example 7: Procedure of the Preparation of YB-8

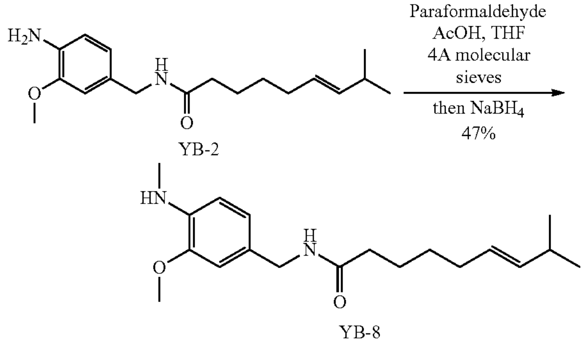

YB-2

YB-8

A mixture of YB-2 (7.9 mg, 0.026 mmol), Paraformaldehyde (4.0 mg, 0.13 mmol), AcOH (0.10 uL, 0.0026 mmol) and small amount of 4 Å molecular sieves in THF (1 mL) was stirred at rt for 12 h. The resulting mixture was carefully treated with solid $NaBH_4$ (3.0 mg, 0.078 mmol) and stirred at rt for 10 min. The reaction was quenched with $H_2O$ (2 mL) at 0° C. The mixture was vigorously stirred at rt for 5 min, then diluted with DCM (3 mL). After separation, the aqueous layer was extracted with DCM (2 mL). The combined organics were dried ($Na_2SO_4$) and concentrated to give a clear oil, which was purified by chromatography (2:1 EtOAc/Hexane) to furnish 3.9 mg of YB-8 (0.012 mmol, 47%), $R_f$0.62 (2:1 EtOAc/Hexane).

$^1$H-NMR (400 MHz, $CDCl_3$) δ 6.79 (d, J=7.8 Hz, 1H, ArH), 6.69 (s, 1H, ArH), 6.51 (d, J=7.8, 1H, ArH), 5.57 (s, 1H, amide NH), 5.18-5.40 (m, 2H, olefin Hs), 4.33 (br.s, 2H, ArCH2N), 4.12 (dd, J=7.1, 3.0 Hz, 1H, aniline NH), 3.82 (s, 3H, ArOCH3), 2.85 (s, 3H, ArNCH3), 2.16-2.23 (m, 2H, alkyl Hs), 1.95-2.05 (m, 2H, alkyl Hs), 1.61-1.68 (m, 2H, alkyl Hs), 1.34-1.41 (m, 2H, alkyl Hs), 1.25 (m, 1H, alkyl H), 0.94 (dd, J=6.8 Hz, 2.8 Hz, 6H, alkyl CH3). MS m/e 319 ($M^+$+H), 341 ($M^+$+Na).

Example 8: Procedure of the Preparation of YB-9

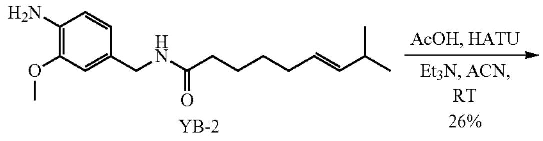

YB-2

-continued

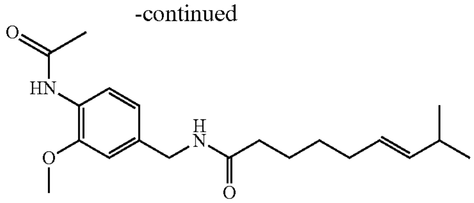

YB-9

A mixture of YB-2 (6.0 mg, 0.020 mmol) and AcOH (1.3 uL, 0.0023 mmol) in ACN (0.5 mL) was treated with $Et_3N$ (5.0 uL, 0.036 mmol) and HATU (15 mg, 0.039 mmol) at rt for 10 min, then quenched with aq. $NaHCO_3$ (2 mL) at 0° C. The mixture was vigorously stirred at rt for 15 min, then diluted with EtOAc (3 mL). After separation, the aqueous layer was extracted with EtOAc (1 mL). The combined organics were dried ($Na_2SO_4$) and concentrated to give a yellow oil, which was purified by chromatography (2:1 EtOAc/Hexane) to furnish 1.8 mg of YB-9 (0.0052 mmol, 26%), $R_f$0.17 (2:1 EtOAc/Hexane).

$^1$H-NMR (400 MHz, $CDCl_3$) δ 8.26 (d, J=7.8 Hz, 1H, ArH), 7.71 (s, 1H, ArH), 6.81 (d, J=8.2 Hz, 1H, ArH), 6.80 (s, 1H, Amide NH), 5.73 (s, 1H, amide NH), 5.18-5.34 (m, 2H, olefin Hs), 4.37 (d, J=5.7 Hz, 2H, ArCH2NH), 3.85 (s, 3H, ArOCH3), 2.17-2.21 (m, 3H, alkyl Hs), 2.18 (s, 3H, CH3CO Hs), 1.96-2.03 (m, 2H, alkyl Hs), 1.60-1.70 (m, 2H, alkyl Hs), 1.33-1.41 (m, 2H, alkyl Hs), 0.93 (d, J=6.8 Hz, 6H, alkyl CH3). MS m/e 347 ($M^+$+H).

Example 9: Procedure of the Preparation of YB-10

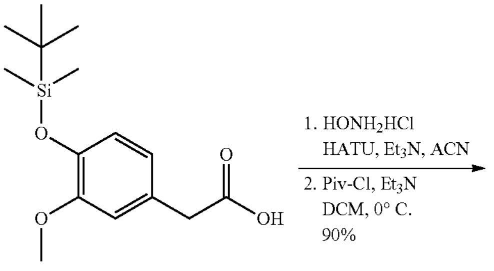

TBS-Homovanillic acid

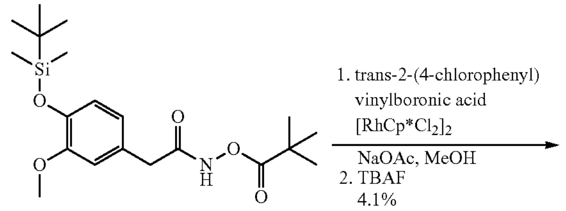

Piv-hydroxylamide

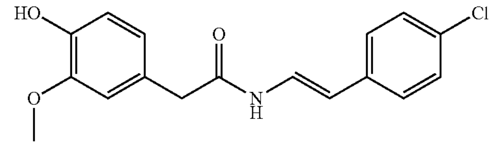

YB-10

$Et_3N$ (0.24 mL, 1.7 mmol) was added dropwise to a suspension of TBS-Homovanillic acid (0.23 g, 0.78 mmol), Hydroxylamine hydrochloride (59 mg, 0.86 mmol; Order Number H158125G from Fisher) and HATU (0.31 g, 0.82 mmol) in ACN (2 mL) at rt. The mixture was stirred at rt for 2 h, then quenched with aq. $NaHCO_3$. The mixture was vigorously stirred at rt for 15 min, then diluted with DCM (5 mL) and $H_2O$ (2 mL). After separation, the aqueous layer was extracted with DCM (2 mL). The combined organics were dried ($Na_2SO_4$) and concentrated to give a crude oil product, $R_f$ 0.33 (2:1 EtOAc/Hexane).

A solution of the crude product from the previous step in DCM (2 mL) was treated with $Et_3N$ (0.14 mL, 1.0 mmol) and Piv-Cl (0.11 mL, 0.86 mmol; Order Number T72605 from Sigma-Aldrich) at 0° C. for 10 min. The reaction was quenched with aq. $NaHCO_3$. The mixture was vigorously stirred at 0° C. for 10 min, then at rt for 15 min. The mixture was diluted with DCM (3 mL). After separation, the aqueous layer was extracted with DCM (2 mL). The combined organics were dried ($Na_2SO_4$) and concentrated to afford a crude yellow oil, which was purified by chromatography (2:3 EtOAc/Hexane) to furnish 0.28 g of Piv-hydroxylamide (0.70 mmol, 90% over 2 steps), $R_f$0.62 (2:3 EtOAc/Hexane).

A mixture of Piv-hydroxylamide prepared in the previous step (40 mg, 0.10 mmol), alkenyl boronic acid: trans-2-(4-chlorophenyl)vinylboronic acid (27 mg, 0.15 mmol; Order Number AC431340010 from Fisher), NaOAc (12 mg. 0.15 mmol), $[RhCp^*Cl_2]_2$ (0.8 mg, 0.001 mmol; Order Number 50-536-096 from Fisher) in anhydrous MeOH (0.5 mL) was stirred at rt for 12 h (*Organic Letters* 2014, 16, 3444), then concentrated to remove the solvent. The crude residue was suspended in ACN (0.5 mL) and treated with a solution of TBAF, 70-75% in water (72 mg, 0.20 mmol) in ACN (0.2 mL) for 20 min. The mixture was quenched with pH 7 buffer (1 mL) and 1N HCl (0.20 mL, 0.20 mmol) at 0° C., then diluted with DCM (4 mL) and $H_2O$ (2 mL). After separation, the aqueous layer was extracted with DCM (2 mL). The combined organics were dried ($Na_2SO_4$) and concentrated to give a crude oil, which was purified by chromatography (2:3 EtOAc/Hexane) to furnish 1.3 mg of YB-10 (0.0041 mmol, 4.1% over 2 steps), $R_f$0.62 (2:1 EtOAc/Hexane).

$^1$H-NMR (400 MHz, $CDCl_3$) δ 7.45 (dd, J=14.4 and 10.8 Hz, 1H, —C═CH—), 7.18-7.24 (m, 4H, Cl—ArHs), 6.77-6.95 (m, 3H, vanillyl ArHs), 5.91 (d, J=14.8 Hz, 1H, —CH═C—), 5.65 (s, 1H, amide NH), 4.29 (d, J=5.6 Hz, 1H, Ar—OH), 3.91 (s, 3H, ArOCH3), 3.62 (s, 2H, ArCH2CO). MS m/e 318 ($M^+$+H).

Example 10: Procedure of the Preparation of YB-11

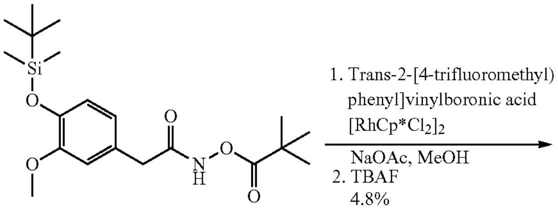

Piv-hydroxylamide

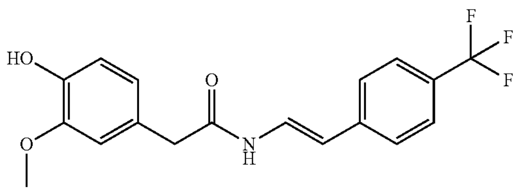

YB-11

A mixture of Piv-hydroxylamide (40 mg, 0.10 mmol), alkenyl boronic acid: Trans-2-[4-(trifluoromethyl)phenyl] vinylboronic acid (32 mg, 0.15 mmol; Order Number BB-8104 from Combi-Blocks), NaOAc (12 mg. 0.15 mmol), $[RhCp^*Cl_2]_2$ (0.8 mg, 0.001 mmol; Order Number 50-536-096 from Fisher) in anhydrous MeOH (0.5 mL) was stirred at rt for 12 h, then concentrated to remove the solvent. The crude residue was suspended in ACN (0.5 mL) and treated with a solution of TBAF, 70-75% in water (72 mg, 0.20 mmol) in ACN (0.2 mL) for 20 min. The mixture was quenched with pH 7 buffer (1 mL) and 1N HCl (0.20 mL, 0.20 mmol) at 0° C., then diluted with DCM (4 mL) and $H_2O$ (2 mL). After separation, the aqueous layer was extracted with DCM (2 mL). The combined organics were dried ($Na_2SO_4$) and concentrated to give a crude oil, which was purified by chromatography (2:3 EtOAc/Hexane) to furnish 1.7 mg of YB-11 (0.0048 mmol, 4.8% over 2 steps), $R_f$ 0.23 (2:3 EtOAc/Hexane).

$^1$H-NMR (400 MHz, $CDCl_3$) δ 7.57 (dd, J=14.6 and 11.0 Hz, 1H, —C═CH—), 7.51 (d, 2H, J=8.2 Hz, CF3-ArHs), 7.35 (d, 2H, J=8.0 Hz, CF3-ArHs), 7.15 (br. d, J=10.3 Hz, 1H, Phenol OH), 6.95 (d, J=7.5 Hz, 1H, vanillyl ArH), 6.78 (d, J=7.8 Hz, 2H, vanillyl ArHs), 5.98 (d, J=14.6 Hz, 1H, —CH═C—), 5.68 (br.d, J=9.6 Hz, 1H, amide NH), 3.91 (s, 3H, ArOCH3), 3.63 (s, 2H, ArCH2CO). MS m/e 352 ($M^+$+H).

Example 11: Modified Procedure of the Preparation of YB-11

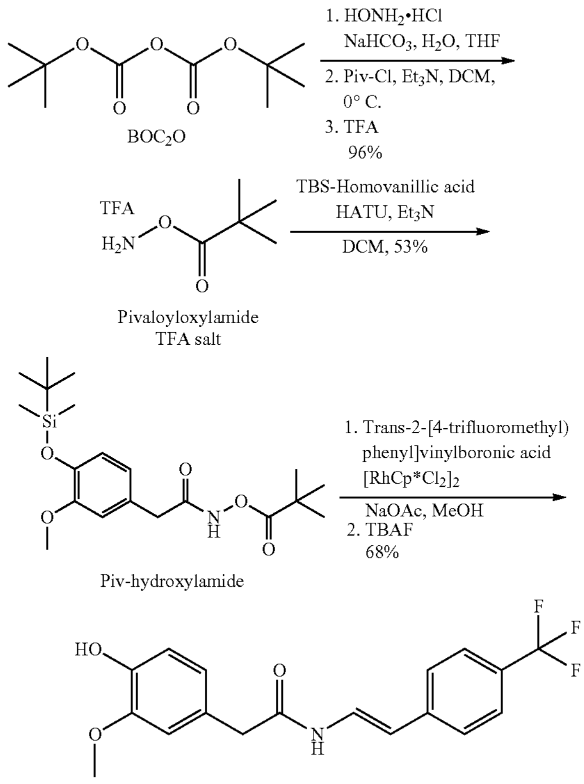

$BOC_2O$
Pivaloyloxylamide TFA salt
Piv-hydroxylamide

YB-11

A solution of $BOC_2O$ (1.1 g, 5.0 mmol) in THF (4 mL) was added to a solution of Hydroxylamine hydrochloride (0.52 g, 7.5 mmol; Order Number H158125G from Fisher), $NaHCO_3$ (1.1 g, 13 mmol) in $H_2O$ (4 mL) at rt. The mixture was vigorously stirred overnight, then concentrated to afford a white solid. The residue was suspended in $CHCl_3$ (10 mL), dried ($Na_2SO_4$) and filtered. The resulted solution was concentrated to give crude N-Boc-hydroxylamine.

$Et_3N$ (0.84 mL, 6.0 mmol) was introduced to a mixture of N-Boc-hydroxylamine and small amount of 4 Å molecular sieves in DCM (16 mL). The mixture was stirred at rt for 10 min before being cooled to 0° C. After the addition of Piv-Cl (0.65 mL, 5.3 mmol; order Number T72605 from Sigma-Aldrich) dropwise via syringe, the mixture was stirred at 0° C. for 15 min, then quenched with aq. $NaHCO_3$. The resulted suspension was vigorously stirred at rt for 5 min. After separation, the aq. layer was extracted with EtOAc. The combined organics were dried ($Na_2SO_4$) and concentrated to give a crude solid, which was dissolved in DCM and passed through a short plug of silica gel (2:1 EtOAc/hexane) to obtain BOC—NH—O-Piv.

BOC—NH—O-Piv $^1$H-NMR (400 MHz, $CDCl_3$) δ 7.76 (s, 1H, CONH), 1.49 (s, 9H, Boc 3 CH3s), 1.30 (s, 9H, Piv 3 CH3s).

BOC—NH—O-Piv was treated with a solution of TFA (2 mL) in DCM (2 mL) at rt for 10 min, then concentrated to remove the volatiles. The residue was diluted with DCM, evaporated and repeated one more time to give 1.1 g of TFA NH2-O-Piv (4.8 mmol, 96% yield).

TBS-Homovanillic acid (0.33 g, 1.1 mmol) in DCM (55 mL) at 0° C. was treated with $Et_3N$ (0.40 mL, 2.9 mmol), 0.25M of TFA $NH_2$—O-Piv in DCM (6.0 mL, 1.5 mmol), then HATU (0.61 g, 1.6 mmol) in 3 portions over 30 min. The mixture was stirred at 0° C. for 10 min, then warmed up to rt. After 40 min, the mixture was quenched with aq. $NaHCO_3$ at 0° C., and the resulted suspension was vigorously stirred at rt for 15 min. After separation, the aqueous layer was extracted with EtOAc. The combined organics were dried ($Na_2SO_4$) and concentrated. The crude product was purified by chromatography (2:3 EtOAc/Hexane) to furnish 0.23 g of Piv-hydroxylamide (0.58 mmol, 53%), $R_f$ 0.21 (1:4 EtOAc/Hexane). TLC showed Piv-hydroxylamide prepared using this route had better purity than the material prepared using the previous route in Example 9.

A mixture of Piv-hydroxylamide (40 mg, 0.10 mmol) prepared in the previous step, alkenyl boronic acid: Trans-2-[4-(trifluoromethyl)phenyl]vinylboronic acid (32 mg, 0.15 mmol; Order Number BB-8104 from Combi-Blocks), NaOAc (12 mg. 0.15 mmol), $[RhCp^*Cl_2]_2$ (0.8 mg, 0.001 mmol; Order Number 50-536-096 from Fisher) in anhydrous MeOH (0.5 mL) was stirred at rt for 12 h, then concentrated to remove the solvent. The crude residue was suspended in ACN (0.5 mL) and treated with a solution of TBAF, 70-75% in water (72 mg, 0.20 mmol) in ACN (0.2 mL) for 20 min. The mixture was quenched with pH 7 buffer (1 mL) and 1N HCl (0.20 mL, 0.20 mmol) at 0° C., then diluted with DCM (4 mL) and $H_2O$ (2 mL). After separation, the aqueous layer was extracted with DCM (2 mL). The combined organics were dried ($Na_2SO_4$) and concentrated to give a crude oil, which was purified by chromatography (2:3 EtOAc/Hexane) to furnish 24 mg of YB-11 (0.068 mmol, 68% over 2 steps), $R_f$ 0.23 (2:3 EtOAc/Hexane). NMR and MS data same as YB-11 from the previous procedure in Example 10.

Example 12: Procedure of the Preparation of YB-12

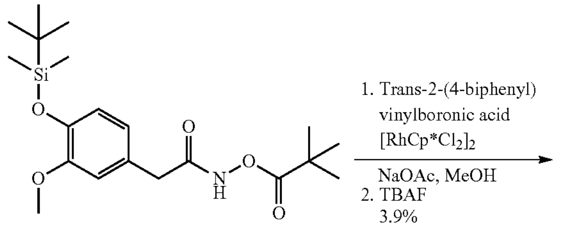

Piv-hydroxylamide

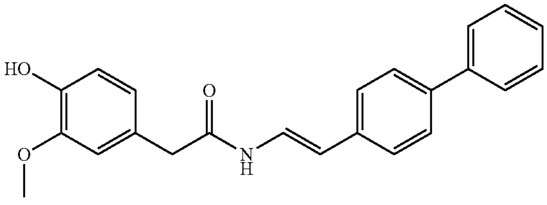

YB-12

A mixture of Piv-hydroxylamide (40 mg, 0.10 mmol) prepared using the route in Example 9, alkenyl boronic acid: Trans-2-(4-biphenyl)vinylboronic acid (34 mg, 0.15 mmol; Order Number BB-8214 from Combi-Blocks), NaOAc (12 mg, 0.15 mmol), $[RhCp^*Cl_2]_2$ (0.8 mg, 0.001 mmol; Order Number 50-536-096 from Fisher) in anhydrous MeOH (1.0 mL) was stirred at rt for 12 h, then concentrated to remove the solvent. The crude residue was suspended in ACN (0.5 mL) and treated with a solution of TBAF, 70-75% in water (72 mg, 0.20 mmol) in ACN (0.2 mL) for 20 min. The mixture was quenched with pH 7 buffer (1 mL) and 1N HCl (0.20 mL, 0.20 mmol) at 0° C., then diluted with DCM (4 mL) and $H_2O$ (2 mL). After separation, the aqueous layer was extracted with DCM (2 mL). The combined organics were dried ($Na_2SO_4$) and concentrated to give a crude oil, which was purified by chromatography (2:3 EtOAc/Hexane) to furnish 1.4 mg of YB-12 (0.0039 mmol, 3.9% over 2 steps), $R_f$ 0.22 (2:3 EtOAc/Hexane).

$^1$H-NMR (400 MHz, $CDCl_3$) δ 7.30-7.56 (m, 10H, —C═CH—, Ar—ArHs), 6.79-6.97 (m, 3H, vanillyl ArHs), 6.00 (d, J=14.8 Hz, 1H, —CH═C—), 5.65 (br.s, 1H, amide NH), 4.29 (d, J=5.6 Hz, 1H, Ar—OH), 3.92 (s, 3H, ArOCH3), 3.63 (s, 2H, ArCH2CO). MS m/e 360 ($M^+$+H).

Example 13: Procedure of the Preparation of YB-13

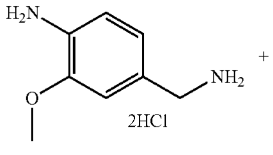

+

4-(aminomethyl)-2-methoxyaniline dihydrochloride

-continued

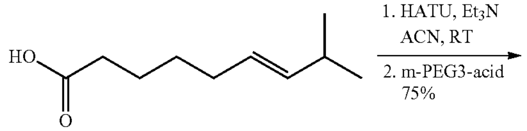

(6E)-8-Methyl-6-nonenoic acid

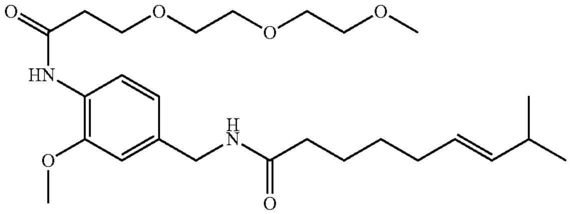

YB-13

$Et_3N$ (39 uL, 0.28 mmol) was added dropwise to a suspension of (6E)-8-methyl-6-nonenoic acid (10 mg, 0.059 mmol; Order Number LN01303052 from LabNetwork), 4-(aminomethyl)-2-methoxyaniline dihydrochloride (14 mg, 0.065 mmol; Order Number EN300-1721327 from Enamine) and HATU (46 mg, 0.12 mmol) in ACN (1 mL) at 0° C. The mixture was stirred at 0° C. for 20 min. After the addition of m-PEG3-acid (17 mg, 0.089 mmol; Cat #BP-20981 from Broadpharm), the mixture was stirred at rt for 40 min, then quenched with aq. $NaHCO_3$ at 0° C. The resulted mixture was vigorously stirred at rt for 15 min, then diluted with DCM (2 mL). After separation, the aqueous phase was extracted with DCM (1 mL). The combined organics were dried ($Na_2SO_4$) and concentrated to give a crude oil, which was purified by chromatography (1:13 MeOH/DCM) to furnish 21 mg of YB-13 (0.044 mmol, 75% over 2 steps), $R_f$ 0.20 (1:20 MeOH/DCM).

$^1$H-NMR (400 MHz, $CDCl_3$) δ 8.61 (s, 1H, Ar—NH—CO), 8.31 (d, J=8.0 Hz, 1H, ArH), 6.83 (d, J=9.8 Hz, 2H, ArHs), 5.68 (s, 1H, Amide NH), 5.19-5.40 (m, 2H, olefin Hs), 4.38 (d, J=5.7 Hz, 2H, ArCH2NH), 3.86 (s, 3H, ArOCH3), 3.82 (t, J=5.6 Hz, 2H, CH2O), 3.71 (s, 4H, 2 CH2O), 3.63-3.65 (m, 2H, CH2O), 3.48-3.53 (m, 2H, CH2O), 3.36 (s, 3H, OCH3), 2.66 (t, J=5.7 Hz, 2H, COCH2), 2.18-2.23 (m, 3H, alkyl Hs), 1.98 (q, J=6.9 Hz, 1H, alkyl H), 1.61-1.69 (m, 3H, alkyl Hs), 1.34-1.42 (m, 2H, alkyl Hs), 0.92-0.95 (d, J=3.4 Hz, 6H, alkyl CH3s). MS m/e 479 ($M^+$+H).

Example 14: Procedure of the Preparation of YB-14

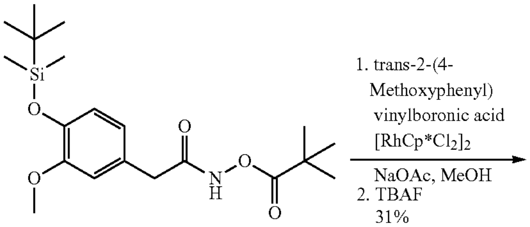

Piv-hydroxylamide

-continued

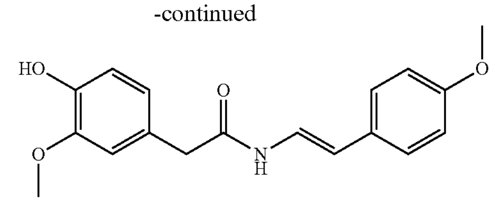

YB-14

A mixture of Piv-hydroxylamide (20 mg, 0.050 mmol) prepared using the route in Example 9, alkenyl boronic acid: trans-2-(4-Methoxyphenyl)vinylboronic acid (14 mg, 0.075 mmol; Order Number BB-8136 from Combi-blocks), NaOAc (6.0 mg. 0.075 mmol), $[RhCp^*Cl_2]_2$ (0.4 mg, 0.0006 mmol; Order Number 50-536-096 from Fisher) in anhydrous MeOH (0.5 mL) was stirred at rt for 12 h, then concentrated to remove the solvent. The crude residue was suspended in ACN (0.5 mL) and treated with a solution of TBAF, 70-75% in water (72 mg, 0.20 mmol) in ACN (0.2 mL) for 20 min. The mixture was quenched with pH 7 buffer (1 mL) and 1N HCl (0.20 mL, 0.20 mmol) at 0° C., then diluted with DCM (4 mL) and $H_2O$ (2 mL). After separation, the aqueous layer was extracted with DCM (2 mL). The combined organics were dried ($Na_2SO_4$) and concentrated to give a crude oil, which was purified by chromatography (2:3 EtOAc/Hexane) to furnish 4.8 mg of YB-14 (0.015 mmol, 31% over 2 steps), $R_f$0.13 (2:3 EtOAc/Hexane).

$^1$H-NMR (400 MHz, $CDCl_3$) δ 7.35 (dd, J=14.6, 10.7 Hz, 1H, —C═CH—), 7.20 (d, 2H, J=8.7 Hz, MeO—ArHs), 7.05 (br.d, J=10.3 Hz, 1H, Phenol OH), 6.94 (d, J=8.5 Hz, 1H, vanillyl ArH), 6.81 (d, J=8.7 Hz, 2H, MeO—ArHs), 6.78 (d, J=5.9 Hz, 2H, vanillyl ArHs), 5.92 (d, J=14.6 Hz, 1H, —CH═C—), 5.30 (s, 1H, amide NH), 3.91 (s, 3H, vanillyl ArOCH3), 3.78 (s, 3H, CH30-Ar), 3.61 (s, 2H, ArCH2CO). MS m/e 314 ($M^+$+H).

Example 15: Procedure of the Preparation of YB-15

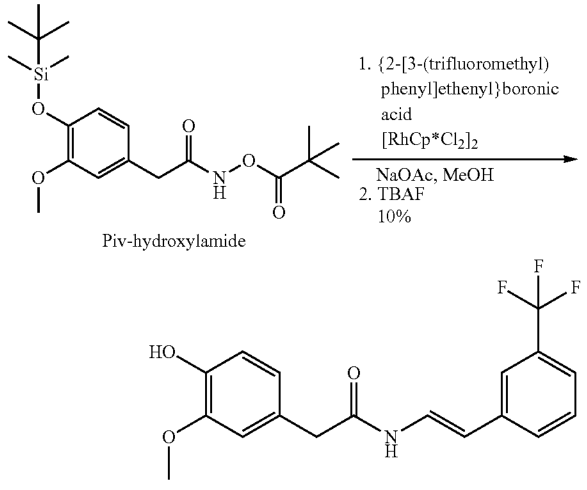

Piv-hydroxylamide

YB-15

A mixture of Piv-hydroxylamide (20 mg, 0.05 mmol) prepared using the route in Example 9, alkenyl boronic acid: {2-[3-(trifluoromethyl)phenyl]ethenyl}boronic acid (E/Z mixture) (16 mg, 0.075 mmol; Order Number EN300-310386 from Enamine), NaOAc (6.0 mg. 0.075 mmol), $[RhCp^*Cl_2]_2$ (0.4 mg, 0.0006 mmol; Order Number 50-536-096 from Fisher) in anhydrous MeOH (0.5 mL) was stirred at rt for 12 h, then concentrated to remove the solvent. The crude residue was suspended in ACN (0.5 mL) and treated with a solution of TBAF, 70-75% in water (72 mg, 0.20 mmol) in ACN (0.2 mL) for 20 min. The mixture was quenched with pH 7 buffer (1 mL) and 1N HCl (0.20 mL, 0.20 mmol) at 0° C., then diluted with DCM (4 mL) and $H_2O$ (2 mL). After separation, the aqueous layer was extracted with DCM (2 mL). The combined organics were dried ($Na_2SO_4$) and concentrated to give a crude oil, which was purified by chromatography (2:3 EtOAc/Hexane) to furnish 1.7 mg of YB-15 (0.0048 mmol, 10% over 2 steps), $R_f$0.20 (2:3 EtOAc/Hexane).

$^1$H-NMR (400 MHz, $CDCl_3$) δ 7.54 (dd, J=14.6 and 11.0 Hz, 1H, —C═CH—), 7.49 (s, 1H, CF3-ArH), 7.37-7.45 (m, 3H, CF3-ArHs), 7.14 (br. d, J=10.3 Hz, 1H, Phenol OH), 6.95 (d, J=8.0 Hz, 1H, vanillyl ArH), 6.79 (d, J=7.3 Hz, 2H, vanillyl ArHs), 5.99 (d, J=14.6 Hz, 1H, —CH═C—), 5.65 (s, 1H, amide NH), 3.91 (s, 3H, ArOCH3), 3.64 (s, 2H, ArCH2CO). MS m/e 352 ($M^+$+H).

Example 16: Procedure of the Preparation of YB-16

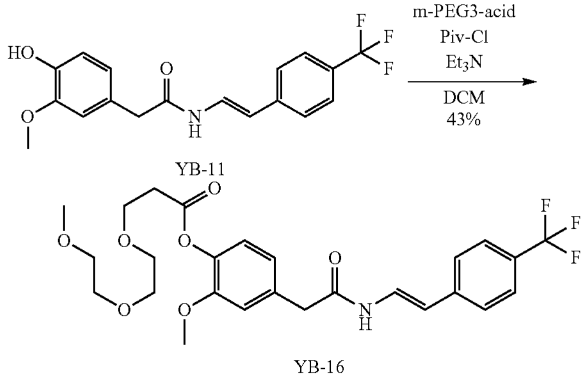

YB-11

YB-16

$Et_3N$ (4.7 uL, 0.034 mmol) was introduced to a mixture of m-PEG3-acid (11 mg, 0.059 mmol; Cat #BP-20981 from Broadpharm) and small amount of 4 Å molecular sieves in DCM (1 mL). The mixture was stirred at rt for 10 min before the addition of Piv-Cl (7.1 uL, 0.058 mmol; order Number T72605 from Sigma-Aldrich). The mixture was stirred at rt for 10 min to form the mixed anhydride.

$Et_3N$ (4.9 uL, 0.035 mmol) was introduced to a mixture of YB-11 (10 mg, 0.028 mmol) and small amount of 4 Å molecular sieves in DCM (1 mL) at 0° C. The mixture was stirred at 0° C. for 10 min before the addition of the freshly prepared mixed anhydride. The resulted mixture was stirred for 12 h at rt and purified by chromatography (2:1 EtOAc/Hexane) to furnish 6.4 mg of YB-16 (0.012 mmol, 43%), $R_f$0.17 (2:1 EtOAc/Hexane).

$^1$H-NMR (400 MHz, $CDCl_3$) δ 7.56 (dd, J=14.6 and 11.0 Hz, 1H, —C═CH—), 7.51 (d, J=8.0 Hz, 2H, CF3-ArHs), 7.36 (d, J=8.2 Hz, 2H, CF3-ArHs), 7.07 (d, J=8.0 Hz, 1H, vanillyl ArH), 6.84-6.88 (m, 2H, vanillyl ArHs), 6.04 (d, J=14.9 Hz, 1H, —CH═C—), 3.89 (t, J=6.5 Hz, 2H, CH2O), 3.83 (s, 3H, ArOCH3), 3.65-3.73 (m, 8H, ArCH2CO, 3 CH2O), 3.55-3.57 (m, 2H, CH2O), 3.38 (s, 3H, OCH3), 2.90 (t, J=6.4 Hz, 2H, COCH2). MS m/e 526 ($M^+$+H).

Example 17: Procedure of the Preparation of YB-17

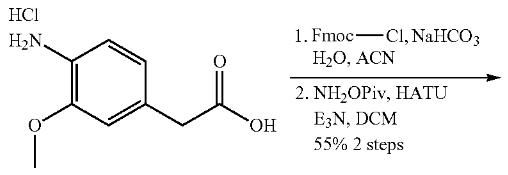

2-(4-amino-3-methoxyphenyl)acetic acid HCl salt

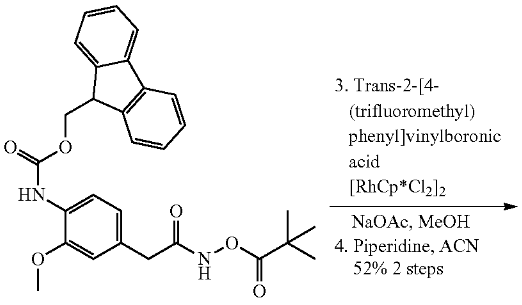

N-pivaloyloxylamide

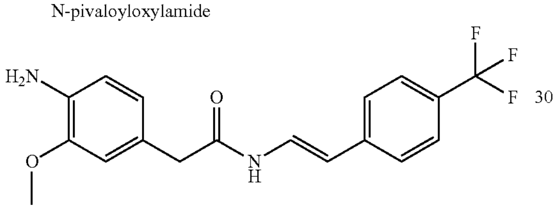

YB-17

A solution of $NaHCO_3$ (50 mg, 0.60 mmol) in $H_2O$ (2 mL) was added to a suspension of 2-(4-amino-3-methoxyphenyl) acetic acid hydrochloride (44 mg, 0.20 mmol; Order Number FCH886354 from Chem-space) and Fmoc-Cl (78 mg, 0.30 mmol) in ACN (2 mL) at rt. The suspension was completely dissolved after the addition. After the solution was vigorously stirred overnight, white solid precipitated out. The mixture was diluted with 1:3 EtOAc/Hexane (6 mL), stirred at 0° C. for 5 min, then filtered to give 85 mg of 2-[4-(Fmoc-amino)-3-methoxyphenyl]acetic acid sodium salt (0.20 mmol, 100%).

A suspension of 2-[4-(Fmoc-amino)-3-methoxyphenyl] acetic acid sodium salt (85 mg, 0.20 mmol) in DCM (10 mL) at 0° C. was treated with 0.25 M of TFA $NH_2$—O-Piv in DCM (1.2 mL, 0.30 mmol), $Et_3N$ (49 uL, 0.35 mmol), then HATU (80 mg, 0.21 mmol) in 3 portions over 30 min. The mixture was stirred at 0° C. for 10 min, then warmed to rt for 1 h 20 min. The mixture was quenched with aq. $NaHCO_3$ at 0° C., and the resulted suspension was vigorously stirred at rt for 15 min. After separation, the aqueous layer was extracted with EtOAc (5 mL). The combined organics were dried ($Na_2SO_4$) and concentrated to give a crude solid, which was purified by chromatography (2:3 EtOAc/Hexane) to furnish 53 mg of N-Pivaloyloxylamide (0.11 mmol, 55% over 2 steps), $R_f$ 0.28 (2:3 EtOAc/Hexane).

N-Pivaloyloxylamide $^1$H-NMR (400 MHz, $CDCl_3$) δ 8.55 (br.s, 1H, NH), 8.05 (br. s, 1H NH), 7.78 (d, J=7.3 Hz, 2H, Fmoc ArHs), 7.63 (d, J=7.3 Hz, 2H, Fmoc ArHs), 7.41 (t, J=7.4 Hz, 2H, Fmoc ArHs), 7.32 (t, J=7.4 Hz, 2H, Fmoc ArHs), 7.27 (m, 1H, ArH), 6.85 (m, 2H, ArHs), 4.50 (d, J=6.2 Hz, 2H, Fmoc CH2), 4.29 (t, J=6.9 Hz, 1H, Fmoc CH), 3.90 (s, 3H, ArOCH3), 3.61 (s, 2H, ArCH2CO), 1.28 (s, 9H, Piv 3 CH3s).

A mixture of N-Pivaloyloxylamide (21 mg, 0.042 mmol), alkenyl boronic acid: Trans-2-[4-(trifluoromethyl)phenyl] vinylboronic acid (16 mg, 0.075 mmol; Order Number BB-8104 from Combi-Blocks), NaOAc (6.0 mg. 0.075 mmol), $[RhCp*Cl_2]_2$ (0.4 mg, 0.0006 mmol; Order Number 50-536-096 from Fisher) in anhydrous MeOH (1.0 mL) was stirred at rt for 12 h, then concentrated to remove the solvent. The crude residue was treated with a 20% solution of piperidine in ACN (1.0 mL) at rt for 20 min, then concentrated to give a crude solid, which was purified by chromatography (2:1 EtOAc/Hexane) to furnish 7.6 mg of YB-17 (0.022 mmol, 52% over 2 steps), $R_f$0.44 (2:1 EtOAc/Hexane).

$^1$H-NMR (400 MHz, $CDCl_3$) δ 7.56 (dd, J=14.6 and 11.2 Hz, 1H, —C═CH—), 7.50 (d, J=8.2 Hz, 2H, CF3-ArHs), 7.35 (d, J=8.2 Hz, 2H, CF3-ArHs), 7.20 (br.d, J=10.3 Hz, 1H, NH), 6.68-6.75 (m, 3H, vanillyl ArHs), 5.95 (d, J=14.6 Hz, 1H, —CH═C—), 3.87 (s, 3H, ArOCH3), 3.61 (s, 2H, ArCH2CO). MS m/e 351 ($M^+$+H).

Example 18: Procedure of the Preparation of YB-18

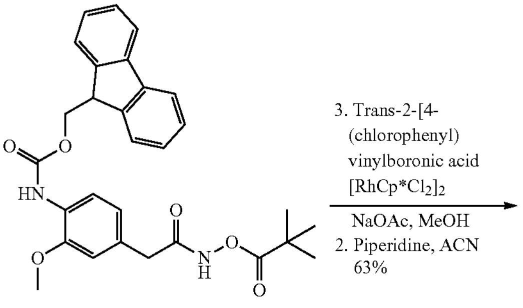

N-pivaloyloxylamide

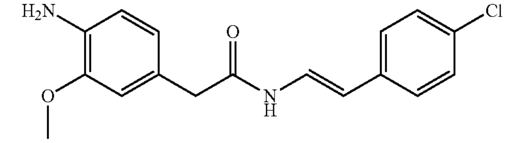

YB-18

A mixture of N-Pivaloyloxylamide (11 mg, 0.021 mmol), alkenyl boronic acid: trans-2-(4-chlorophenyl)vinylboronic acid (5.8 mg, 0.032 mmol; Order Number AC431340010 from Fisher), NaOAc (2.6 mg. 0.032 mmol), $[RhCp*Cl_2]_2$ (0.2 mg, 0.0003 mmol; Order Number 50-536-096 from Fisher) in anhydrous MeOH (1.0 mL) was stirred at rt for 12 h, then concentrated to remove the solvent. The crude residue was treated with a 20% solution of piperidine in ACN (1.0 mL) at rt for 20 min, then concentrated to give a crude solid, which was purified by chromatography (3:2 EtOAc/Hexane) to furnish 4.2 mg of YB-18 (0.013 mmol, 63% over 2 steps), $R_f$0.44 (2:1 EtOAc/Hexane).

$^1$H-NMR (400 MHz, $CDCl_3$) δ 7.45 (dd, J=14.6 and 10.7 Hz, 1H, —C═CH—), 7.12-7.23 (m, 4H, Cl—ArHs), 6.67-6.74 (m, 3H, vanillyl ArHs), 5.88 (d, J=14.6 Hz, 1H, —CH═C—), 3.86 (s, 3H, ArOCH3), 3.59 (s, 2H, ArCH2CO). MS m/e 317 ($M^+$+H).

Example 19: Procedure of the Preparation of YB-19

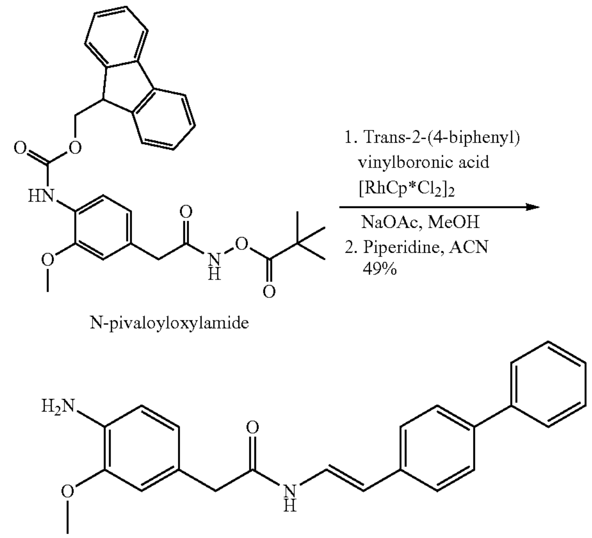

N-pivaloyloxylamide

YB-19

A mixture of N-Pivaloyloxylamide (11 mg, 0.021 mmol), alkenyl boronic acid: Trans-2-(4-biphenyl)vinylboronic acid (7.2 mg, 0.032 mmol; Order Number BB-8214 from Combi-Blocks), NaOAc (2.6 mg. 0.032 mmol), $[RhCp^*Cl_2]_2$ (0.2 mg, 0.0003 mmol; Order Number 50-536-096 from Fisher) in anhydrous MeOH (1.0 mL) was stirred at rt for 12 h, then concentrated to remove the solvent. The crude residue was treated with a 20% solution of piperidine in ACN (1.0 mL) at rt for 20 min, then concentrated to give a crude solid, which was purified by chromatography (3:2 EtOAc/Hexane) to furnish 3.7 mg of YB-19 (0.010 mmol, 49% over 2 steps), $R_f$0.46 (2:1 EtOAc/Hexane).

$^1$H-NMR (400 MHz, $CDCl_3$) δ 7.57 (d, J=8.0 Hz, 2H, Ar—ArHs), 7.50-7.53 (m, 3H, —C═CH—, Ar—ArHs), 7.42 (t, J=7.5 Hz, 2H, Ar—ArHs), 7.30-7.35 (m, 3H, Ar—ArHs), 7.16 (br. d, J=10.7 Hz, 1H, NH), 6.69-6.75 (m, 3H, vanillyl ArHs), 5.97 (d, J=14.6 Hz, 1H, —CH═C—), 3.87 (s, 3H, ArOCH3), 3.61 (s, 2H, ArCH2CO). MS m/e 359 ($M^+$+H).

Example 20: Procedure of the Preparation of YB-20

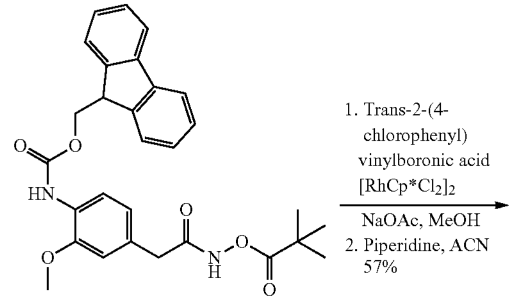

N-pivaloyloxylamide

-continued

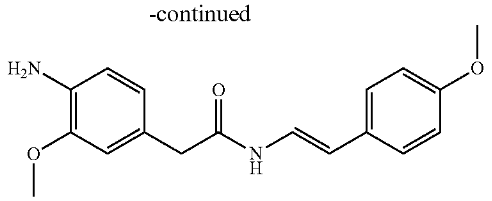

YB-20

A mixture of N-Pivaloyloxylamide (11 mg, 0.021 mmol), alkenyl boronic acid: trans-2-(4-Methoxyphenyl)vinylboronic acid (5.7 mg, 0.032 mmol; Order Number BB-8136 from Combi-block), NaOAc (2.6 mg. 0.032 mmol), $[RhCp^*Cl_2]_2$ (0.2 mg, 0.0003 mmol; Order Number 50-536-096 from Fisher) in anhydrous MeOH (1.0 mL) was stirred at rt for 12 h, then concentrated to remove the solvent. The crude residue was treated with a 20% solution of piperidine in ACN (1.0 mL) at rt for 20 min, then concentrated to give a crude solid, which was purified by chromatography (3:2 EtOAc/Hexane) to furnish 3.9 mg of YB-20 (0.012 mmol, 57% over 2 steps), $R_f$0.35 (2:1 EtOAc/Hexane).

$^1$H-NMR (400 MHz, $CDCl_3$) δ 7.35 (dd, J=14.5, 10.9 Hz, 1H, —C═CH—), 7.20 (d, 2H, J=8.5 Hz, MeO—ArHs), 7.08 (br.d, J=10.7 Hz, 1H, NH), 6.81 (d, J=8.7 Hz, 2H, MeO—ArHs), 6.68-6.74 (m, 3H, vanillyl ArHs), 5.89 (d, J=14.6 Hz, 1H, —CH═C—), 3.86 (s, 3H, vanillyl ArOCH3), 3.78 (s, 3H, CH30-Ar), 3.58 (s, 2H, ArCH2CO). MS m/e 313 ($M^+$+H).

Example 21: Procedure of the Preparation of YB-21

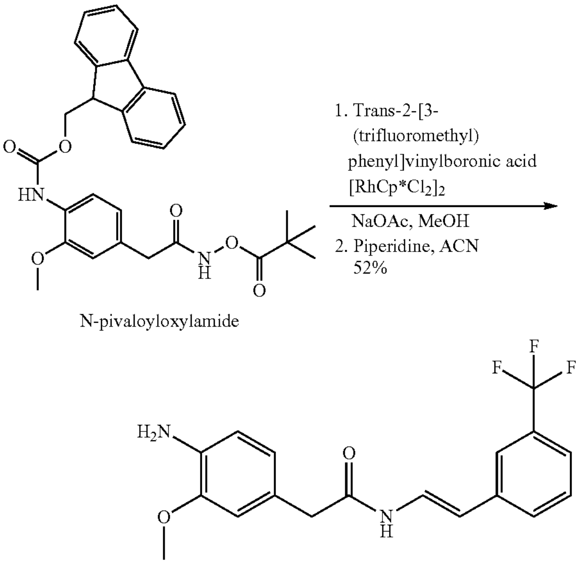

N-pivaloyloxylamide

YB-21

A mixture of N-Pivaloyloxylamide (11 mg, 0.021 mmol), alkenyl boronic acid: {2-[3-(trifluoromethyl)phenyl] ethenyl}boronic acid (E/Z mixture) (6.9 mg, 0.032 mmol; Order Number EN300-310386 from Enamine), NaOAc (2.6 mg. 0.032 mmol), $[RhCp^*Cl_2]_2$ (0.2 mg, 0.0003 mmol; Order Number 50-536-096 from Fisher) in anhydrous MeOH (1.0 mL) was stirred at rt for 12 h, then concentrated to remove the solvent. The crude residue was treated with a 20% solution of piperidine in ACN (1.0 mL) at rt for 20 min, then concentrated to give a crude solid, which was purified by chromatography (3:2 EtOAc/Hexane) to furnish 4.0 mg of YB-21 (0.011 mmol, 52% over 2 steps), $R_f$0.50 (2:1 EtOAc/Hexane).

$^1$H-NMR (400 MHz, $CDCl_3$) δ 7.54 (dd, J=14.6 and 11.0 Hz, 1H, —C═CH—), 7.48 (s, 1H, CF3-ArH), 7.36-7.44 (m, 3H, CF3-ArHs), 7.19 (br. d, J=11.0 Hz, 1H, NH), 6.68-6.75 (m, 3H, vanillyl ArHs), 5.95 (d, J=14.6 Hz, 1H, —CH═C—), 3.86 (s, 3H, ArOCH3), 3.61 (s, 2H, ArCH2CO). MS m/e 351 ($M^+$+H).

Example 22: Procedure of the Preparation of YB-22

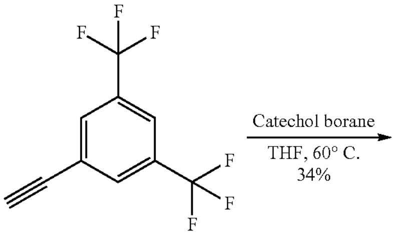

3,5-Bis(trifluoromethyl) phenylacetylene

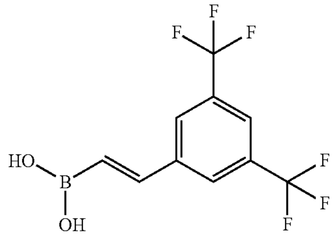

Trans-2-[3,5-bis(trifluoromethyl) phenyl]vinylboronic acid

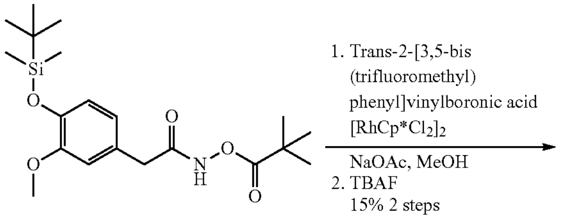

Piv-hydroxylamide

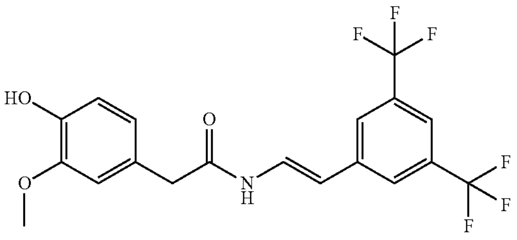

YB-22

3,5-Bis(trifluoromethyl)phenylacetylene (0.12 g, 0.50 mmol; Order Number SS-4899 from Combi-Blocks) was treated with 1 M solution of catechol borane in THF (0.75 mL, 0.75 mmol) under nitrogen atmosphere at 60° C. for 17 h. The mixture was quenched with water (2.5 mL) and vigorously stirred at rt for 4 h, then concentrated to give a white solid residue, which was purified by chromatography (EtOAc) to furnish 49 mg of Trans-2-[3,5-bis(trifluoromethyl)phenyl]vinylboronic acid (0.17 mmol, 34%), $R_f$0.43 (EtOAc).

A mixture of Piv-hydroxylamide (11 mg, 0.028 mmol) prepared using the route in Example 9, alkenyl boronic acid: Trans-2-[3,5-bis(trifluoromethyl)phenyl]vinylboronic acid (12 mg, 0.042 mmol), NaOAc (3.4 mg. 0.042 mmol), $[RhCp^*Cl_2]_2$ (0.2 mg, 0.0004 mmol; Order Number 50-536-096 from Fisher) in anhydrous MeOH (0.5 mL) was stirred at rt for 12 h, then concentrated to remove the solvent. The crude residue was suspended in ACN (0.5 mL) and treated with a solution of TBAF, 70-75% in water (20 mg, 0.056 mmol) in ACN (0.2 mL) for 20 min. The mixture was quenched with pH 7 buffer (1 mL) and 1N HCl (0.20 mL, 0.20 mmol) at 0° C., then diluted with DCM (4 mL) and $H_2O$ (2 mL). After separation, the aqueous layer was extracted with EtOAc (2 mL). The combined organics were dried ($Na_2SO_4$) and concentrated to give a crude oil, which was purified by chromatography (2:3 EtOAc/Hexane) to furnish 1.7 mg of YB-22 (0.0041 mmol, 15% over 2 steps), $R_f$ 0.25 (2:3 EtOAc/Hexane).

$^1$H-NMR (400 MHz, $CDCl_3$) δ 7.66 (s, 2H, CF3-ArHs), 7.63 (s, 1H, CF3-ArH), 7.61 (dd, J=14.8 and 10.8 Hz, 1H, —C═CH—), 7.45 (br. s, 1H, Phenol OH), 6.95 (d, J=8.5 Hz, 1H, vanillyl ArH), 6.78-6.80 (m, 2H, vanillyl ArHs), 6.02 (d, J=14.6 Hz, 1H, —CH═C—), 5.69 (s, 1H, amide NH), 3.91 (s, 3H, ArOCH3), 3.64 (s, 2H, ArCH2CO). MS m/e 420 ($M^+$+H).

Example 23: Procedure of the Preparation of YB-23

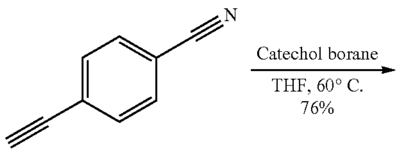

4-ethynylbenzonitrile

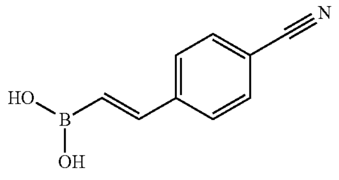

Trans-2-(4-cyanophenyl) vinylboronic acid

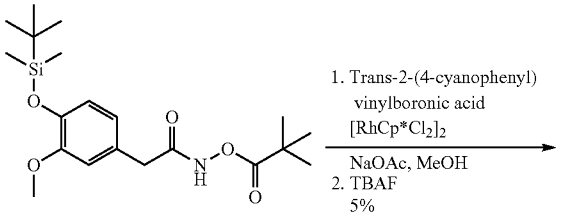

Piv-hydroxylamide

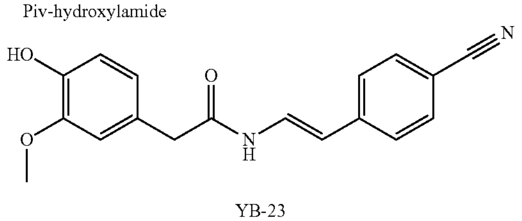

YB-23

4-Ethynylbenzonitrile (0.13 g, 1.0 mmol; Order Number QA-3961 from Combi-Blocks) was treated with 1 M solution of catechol borane in THF (2.0 mL, 2.0 mmol) under nitrogen atmosphere at 60° C. for 3 days. The mixture was quenched with water (4 mL) and vigorously stirred at rt for 4 h, then concentrated to obtain a residue, which was purified by chromatography (EtOAc) to furnish 0.13 g of Trans-2-(4-cyanophenyl)vinylboronic acid (0.76 mmol, 76%), $R_f$0.34 (EtOAc).

A mixture of Piv-hydroxylamide (11 mg, 0.028 mmol) prepared using the route in Example 9, alkenyl boronic acid: Trans-2-(4-cyanophenyl)vinylboronic acid (7.3 mg, 0.042 mmol), NaOAc (3.4 mg. 0.042 mmol), $[RhCp^*Cl_2]_2$ (0.2 mg, 0.0004 mmol; Order Number 50-536-096 from Fisher) in anhydrous MeOH (0.5 mL) was stirred at rt for 12 h, then concentrated to remove the solvent. The crude residue was suspended in ACN (0.5 mL) and treated with a solution of TBAF, 70-75% in water (20 mg, 0.056 mmol) in ACN (0.2 mL) for 20 min. The mixture was quenched with pH 7 buffer (1 mL) and 1N HCl (0.20 mL, 0.20 mmol) at 0° C., then diluted with DCM (4 mL) and $H_2O$ (2 mL). After separation, the aqueous layer was extracted with EtOAc (2 mL). The combined organics were dried ($Na_2SO_4$) and concentrated to give a crude oil, which was purified by chromatography (2:3 EtOAc/Hexane) to furnish 0.4 mg of YB-23 (0.001 mmol, 5% over 2 steps), $R_f$ 0.10 (2:3 EtOAc/Hexane).

$^1$H-NMR (400 MHz, $CDCl_3$) δ 7.59 (dd, J=14.8 and 11.2 Hz, 1H, —C═CH—), 7.54 (d, 2H, J=8.4 Hz, CN—ArHs), 7.33 (d, 2H, J=8.2 Hz, CN—ArHs), 6.91-6.97 (m, 1H, vanillyl ArH), 6.77-6.79 (m, 2H, vanillyl ArHs), 5.95 (d, J=14.4 Hz, 1H, —CH═C—), 5.66 (s, 1H, amide NH), 3.91 (s, 3H, ArOCH3), 3.64 (s, 2H, ArCH2CO). MS m/e 309 ($M^+$+H).

Example 24: Procedure of the Preparation of YB-29

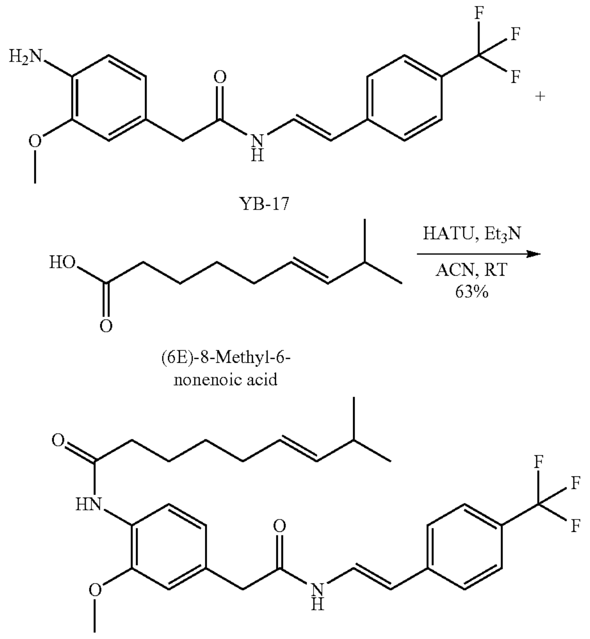

YB-17

(6E)-8-Methyl-6-nonenoic acid

YB-29

A mixture of YB-17 (3.0 mg, 0.0086 mmol) and (6E)-8-methyl-6-nonenoic acid (2.2 mg, 0.013 mmol; Order Number LN01303052 from LabNetwork) in ACN (0.5 mL) was treated with $Et_3N$ (1.4 uL, 0.010 mmol) and HATU (3.4 mg, 0.0090 mmol) at rt for 12 h, then quenched with aq. $NaHCO_3$. The mixture was vigorously stirred at rt for 15 min, then diluted with EtOAc (3 mL) and $H_2O$ (3 mL). The organic phase was separated, and the aqueous phase was extracted with EtOAc (1 mL). The combined organics were dried ($Na_2SO_4$) and concentrated to give a crude material, which was purified by chromatography (1:1 EtOAc/Hexane) to afford 2.7 mg of YB-29 (0.0054 mmol, 63%), $R_f$ 0.53 (1:1 EtOAc/Hexane).

$^1$H-NMR (400 MHz, $CDCl_3$) δ 8.41 (d, J=8.2 Hz, 1H, ArH), 7.76 (s, 1H, ArH), 7.55 (dd, J=14.8, 11.1 Hz, 1H, —C═CH—), 7.50 (d, J=8.2 Hz, 2H, CF3-ArHs), 7.35 (d, J=8.2 Hz, 2H, CF3-ArHs), 6.88 (d, J=8.2, 1H, ArH), 6.80 (s, 1H, Amide NH), 5.99 (d, J=14.6 Hz, 1H, —C═CH—), 5.37 (dd, J=7.8, 5.7 Hz, 2H, olefin Hs), 3.90 (s, 3H, ArOCH3), 3.66 (s, 2H, ArCH2CO), 2.39-2.62 (m, 3H, alkyl Hs), 2.19-2.27 (m, 1H, alkyl H), 2.03 (q, J=6.8 Hz, 1H, alkyl H), 1.70-1.76 (m, 2H, alkyl Hs), 1.41-1.49 (m, 1H, alkyl Hs), 1.04 (d, J=6.9 Hz, 1H, alkyl H), 0.96 (d, J=6.8 Hz, 6H, 2 alkyl CH3s). MS m/e 503 ($M^+$+H).

Example 25: Procedure of the Preparation of YB-30

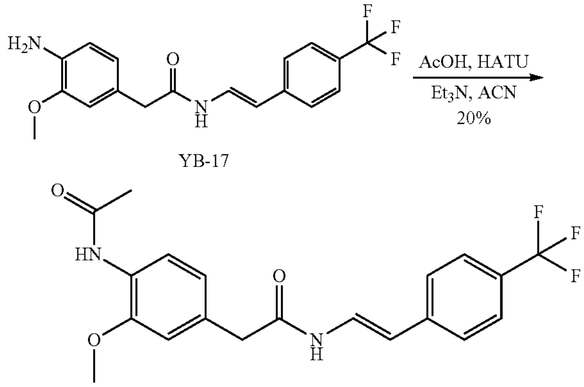

YB-17

YB-30

A mixture of YB-17 (3.0 mg, 0.0086 mmol) and AcOH (0.74 uL, 0.013 mmol) in ACN (0.5 mL) was treated with $Et_3N$ (1.4 uL, 0.010 mmol) and HATU (3.4 mg, 0.0090 mmol) at rt for 12 h, then quenched with aq. $NaHCO_3$. The mixture was vigorously stirred at rt for 15 min, then diluted with EtOAc (3 mL) and $H_2O$ (3 mL). The organic phase was separated, and the aqueous phase was extracted with EtOAc (1 mL). The combined organics were dried ($Na_2SO_4$) and concentrated to give a crude material, which was purified by chromatography (1:1 EtOAc/Hexane) to afford 0.7 mg of YB-30 (0.002 mmol, 20%), $R_f$ 0.09 (1:1 EtOAc/Hexane).

$^1$H-NMR (400 MHz, $CD_3OD$) δ 7.88 (d, J=8.0 Hz, 1H, ArH), 7.48-7.62 (m, 5H, —C═CH—, 4 CF3-ArHs), 7.00 (s, 1H, ArH), 6.88 (d, J=8.4 Hz, 1H, ArH), 6.28 (d, J=14.9 Hz, 1H, —C═CH—), 3.90 (s, 3H, ArOCH3), 3.60 (s, 2H, ArCH2CO), 2.15 (s, 3H, CH3CO). MS m/e 393 ($M^+$+H).

Example 26: Procedure of the Preparation of YB-31 and YB-35

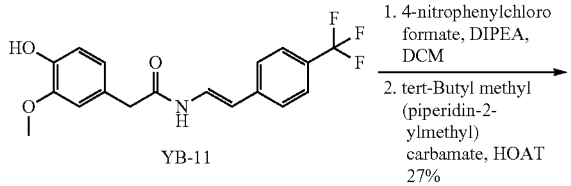

YB-11

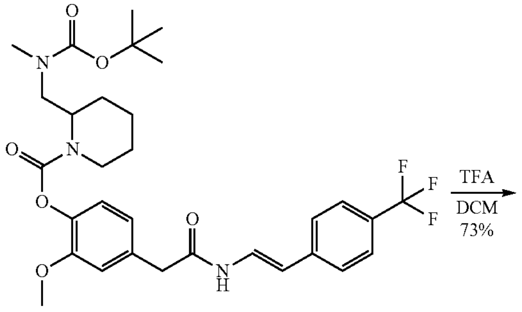

YB-31

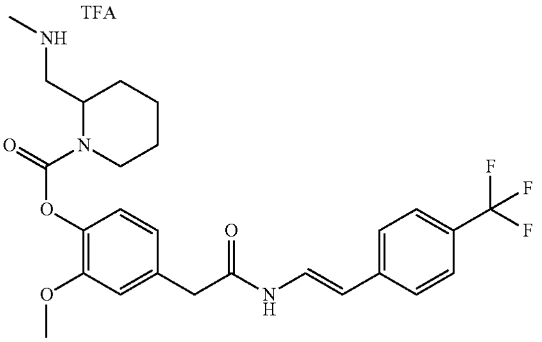

YB-35

A solution of YB-11 (26 mg, 0.074 mmol) in DCM (1 mL) was treated with DIPEA (38 uL, 0.22 mmol) and 4-nitrophenylchloroformate (15 mg, 0.074 mmol; Cat #AAA1874222, Fisher) at rt for 15 min, then further treated with HOAt (0.7 mg, 0.007 mmol; Cat #50-190-4970, Fisher) and tert-butyl methyl(piperidin-2-ylmethyl)carbamate (20 mg, 0.089 mmol; Cat #AC100240, Ascension Chemical Company) for 12 h, then quenched with aq. $NaHCO_3$. The mixture was vigorously stirred at rt for 10 min, then diluted with EtOAc (3 mL) and $H_2O$ (3 mL). The organic phase was separated, and the aqueous phase was extracted with EtOAc (1 mL). The combined organics were dried ($Na_2SO_4$) and concentrated to give a crude material, which was purified by chromatography (2:1 EtOAc/Hexane) to afford 12 mg of YB-31 (0.020 mmol, 27%), $R_f$ 0.58 (2:1 EtOAc/Hexane).

YB-31 $^1$H-NMR (400 MHz, $CDCl_3$) δ 7.49-7.62 (m, 3H, —C═CH—, 2 CF3-ArHs), 7.35 (d, J=8.0 Hz, 2, 2H, CF3-ArHs), 7.08-7.13 (m, 1H, vanillyl ArH), 6.78-6.83 (m, 2H, vanillyl ArHs), 6.06 (d, J=14.0 Hz, 1H, —CH═C—), 4.65 & 4.53 (br.s, 1H, NH), 4.18 (br.s, 1H, NCH), 3.83 (s, 3H, ArOCH3), 3.63 (s, 2H, ArCH2CO), 3.59-3.77 (m, 2H, NCH2), 3.32 (br.s, 1H, NCH), 2.92 (s, 3H, NCH3), 2.88 (br.s, 1H, NCH), 1.71 (br.s, 4H, 2 CH2s), 1.46 (br.s, 2H, CH2), 1.45 (s, 9H, 3 BOC CH3s). MS m/e 628 ($M^+$+Na), 606 ($M^+$+H).

YB-31 (8.9 mg, 0.015 mmol) was treated with a dry solution of 1:3 TFA-DCM (1 mL; dried with 4 Å molecular sieves) at rt for 1 h, then concentrated to remove the volatiles. The residue was suspended in $CHCl_3$ and filtered to collect 7.0 mg of solid YB-35 as a TFA salt (0.011 mmol, 73% yield).

YB-35 $^1$H-NMR (400 MHz, $CD_3OD$) δ 7.48-7.61 (m, —C═CH—, 5H, CF3-ArHs), 7.08 (d, J=7.5 Hz, 2H, vanillyl ArHs), 6.93 (d, J=7.8 Hz, 1H, vanillyl ArH), 6.30 (d, J=14.6 Hz, 1H, —CH═C—), 3.08-4.28 (m, 5H, NCH), 3.87 (s, 3H, ArOCH3), 3.64 (s, 2H, ArCH2CO), 2.78 (s, 3H, NCH3), 1.28-1.88 (m, 6H, 3 CH2s). MS m/e 506 ($M^+$+H).

Example 27: In Vitro $Ca^{2+}$ Flux Assay Development

Capsaicin-like TRPV1 agonists with potent in vitro activity ($EC_{50}$<1 μM in $Ca^{2+}$ flux assay) are proven to show significant analgesic properties in vivo (*J. Med. Chem.* 1993, 36, 2362). It is important to test the compounds in an in vitro assay like $Ca^{2+}$ flux assay with in vivo predictability. Therefore, $Ca^{2+}$ flux assay was developed to evaluate the synthetic compounds.

Figure 2:
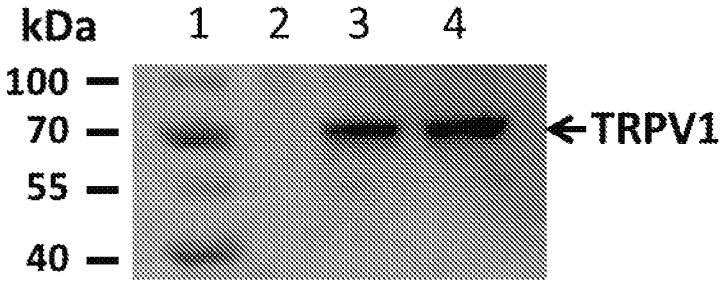
FIG. 2 is a photograph of a gel showing TRPV1 protein expression in HEK 293 cells detected by Western blot. Lane 1: protein ladders, Lane 2: HEK 293 cell alone, Lane 3: 18 h post-transfection, Lane 4: 23 h post-transfection.

The plasmid DNA carrying a human TRPV1 coding sequence (Cat #OHu19934, GenScript Biotech Corp, Piscataway, NJ) was introduced into *E. coli* DH5α™ Competent Cells (Cat #18265017, Invitrogen) to prepare large scale plasmid DNA (FIG. 1). After transient transfection of FreeStyle™ 293-F Cells (FreeStyle™ 293 Expression System, cat #K9000-01, Invitrogen) with plasmid DNA, western blot was used to confirm the TRPV1 expression in transfected HEK 293 cells (FIG. 2). After 23 h, the transfected cells were harvested and stored in liquid nitrogen until screening use. High-throughput $Ca^{2+}$ influx assay was established in a 96-well format (Cat #3882, Corning) using the TRPV1 overexpressing cells pre-treated with calcium dye (FLIPR® Calcium 5 Assay Kit, Cat #R8185, Molecular Device, San Jose, CA). After the addition of compounds, the fluorescence signals were read on a fluorometric imaging plate reader (Synergy H1 Multi-Mode Reader, BioTek® Instruments, Inc. Winooski, Vermont) (*J Biomol Screen* 2007, 12, 61). Capsaicin, a known TRRV1 agonist (Cat #098839, Matrix Scientific), was used as a positive control and PBS was used as a negative control for the assay. In vitro $Ca^{2+}$ flux assays using human TRPV3 or TRPA1 overexpressing cells were developed using the similar procedure as TRPV1. TRPV3 and TRPA1 assays were used in the counter-screens to eliminate false positives due to interference of the assay by the compounds (e.g., fluorescent compounds) and evaluate the specificity of active hits.

Example 28: In Vitro TRPV1 Activity and Specificity Screening

Figure 3A:
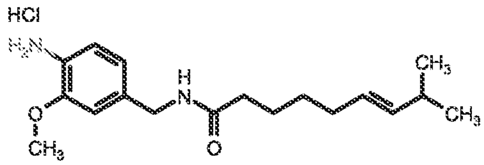
FIGS. 3A and 3B represent a structure of YB-2 and dose response curve in a calcium uptake assay using human TRPV1 transfected HEK 293 cells.
Figure 3B:
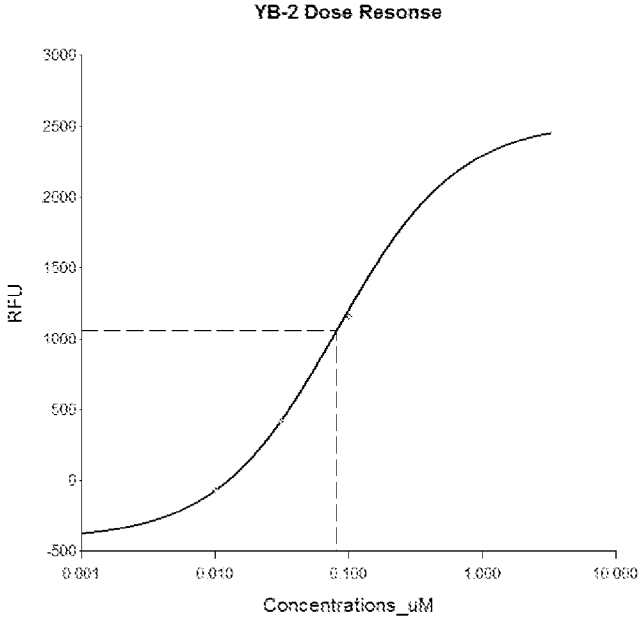

Synthesized capsaicin analogs were screened in the TRPV1 $Ca^{2+}$ flux assay and counter-screened in the TRPV3 and TRPA1 $Ca^{2+}$ flux assays. Each compound was assigned a random code and tested, blinded to compound identity. A 3-min kinetic reading protocol with blank-subtraction was set up using the Gen5 software. The Excitation wavelength was set as 485 nm and the Emission wavelength was set as 525 nm. After initial background reading, compound solutions were added to the plate with a multichannel pipette and the 3-min kinetic reading started immediately. The maximum value for each kinetic reading was subtracted by the background value of the same well to give the net value. The net values were plotted against the corresponding concentrations to generate dose response curves (FIG. 3) and $EC_{50}$ data in Table 1 are shown as Means±SEM from three independent experiments. Twenty of twenty-seven analogs were fairly active with $EC_{50}$s<10 μM. YB-2, YB-10, YB-11 and YB-15 were among the most potent with $EC_{50}$s<0.1 μM. All these analogs were inactive up to 10 μM in TRPV3 or TRPA1 overexpressing cell-based $Ca^{2+}$ flux assays, suggesting the specific activity for TRPV1.

TABLE 1

In vitro human TRPV1 agonistic activity and specificity

| Compound | TRPV1 $EC_{50}$ (μM) | TRPV3 $EC_{50}$ (μM) | TRPA1 $EC_{50}$ (μM) |
|---|---|---|---|
| Capsaicin | 0.11 ± 0.021 | >10 | >10 |
| YB-1 | 27 ± 3.8 | >10 | >10 |
| YB-2 | 0.082 ± 0.015 | >10 | >10 |
| YB-3 | >10 | >10 | >10 |
| YB-4 | 0.68 ± 0.12 | >10 | >10 |
| YB-5 | 2.0 ± 0.29 | >10 | >10 |
| YB-6 | >10 | >10 | >10 |
| YB-7 | >10 | >10 | >10 |
| YB-8 | 1.9 ± 0.23 | >10 | >10 |
| YB-9 | 0.96 ± 0.12 | >10 | >10 |
| YB-10 | 0.047 ± 0.0075 | >10 | >10 |
| YB-11 | 0.012 ± 0.0033 | >10 | >10 |
| YB-12 | 0.60 ± 0.069 | >10 | >10 |
| YB-13 | 3.1 ± 0.41 | >10 | >10 |
| YB-14 | 0.33 ± 0.041 | >10 | >10 |
| YB-15 | 0.048 ± 0.0057 | >10 | >10 |
| YB-16 | 0.93 ± 0.082 | >10 | >10 |
| YB-17 | 1.1 ± 0.29 | >10 | >10 |
| YB-18 | 1.0 ± 0.20 | >10 | >10 |
| YB-19 | 45 ± 3.3 | >10 | >10 |
| YB-20 | 4.9 ± 0.73 | >10 | >10 |
| YB-21 | 0.34 ± 0.065 | >10 | >10 |
| YB-22 | 0.21 ± 0.052 | >10 | >10 |
| YB-23 | 0.30 ± 0.074 | >10 | >10 |
| YB-29 | >10 | >10 | >10 |
| YB-30 | 8.8 ± 0.90 | >10 | >10 |
| YB-31 | >10 | >10 | >10 |
| YB-35 | 0.71 ± 0.14 | >10 | >10 |

As a result of the medicinal chemistry work, the synthetic analogs with novel structural features as described herein significantly expanded the limited SAR of capsaicin scaffold and rectified some erroneous conclusions from the previously reported SAR studies in literature: 1. Phenol functional group in the aromatic region was considered crucial for activity and previous attempts by chemists to modify phenol group resulted in loss of activity (*J. Med. Chem.* 1993, 36, 2362). Promising activities of amine analogs YB-2, YB-8, YB-9, YB-13, YB-17, YB-18, YB-20 and YB-21 demonstrate that phenol group can be replaced with amino, alkylamino, and amide groups; 2. NH group in amide region was considered required for activity and previous attempts by chemists to protect or replace NH group resulted in loss of activity (*J. Med. Chem.* 1993, 36, 2373). In the absence of NH group at amide region, the new oxazoline analogs YB-4 and YB-5 were fairly active. This suggests that N-methylation of the amide group (capsaicin analog 3d in reference: *J. Med. Chem.* 1993, 36, 2373; $EC_{50}$>100 μM in $Ca^{2+}$ influx assay) likely affects the conformation of the molecule, rather than disrupting amide NH from acting as a hydrogen bonding donor to the TRPV1 receptor. This is consistent with the low energy conformations calculated by MOE 2020.0901 using the LowModeMD method (Chemical Computing Group). Low energy conformation of Capsaicin is similar to that of YB-4 and is quite different from that of N-Me capsaicin (FIG. 4). This is also supported by the lack of direct interaction between capsaicin amide NH group and TRPV1 receptor based on the analysis of cryoEM structure of capsaicin bound to TRPV1 (FIG. 5) (*Nat Commun* 2021, 12, 2154; *PNAS* 2016, 113, E137-E145); 3. Overall size and hydrophobicity were considered more important than the detailed structure variations in the hydrophobic side chain region (*J. Med. Chem.* 1993, 36, 2381). Although the cryoEM structure indicates that lipophilicity is a key driver of activity in this region of the molecule and the binding pocket has ample space, detailed structure variations can still make significant impact on the activity. Compared to YB-2, N-[(4-amino-3-methoxyphenyl)methyl]-Nonanamide (Structure in references section. *J. Med. Chem.* 1993, 36, 2362) lacks the unsaturated olefin functionality and methyl substitution group. The absence of these structural features completely abolished the activity ($EC_{50}$>10 μM in $Ca^{2+}$ influx assay as reported in literature). The potent activity of YB-2 suggests the importance of unsaturation and/or substitution in the side chain region. The structures of oxazoline analogs YB-3, YB-4 and YB-5 are similar, their activities are quite different, and YB-4 with a trifluoromethyl substitution on the side chain is most potent with an $EC_{50}$ of 0.68 μM. Similarly, although structures of enamide analogs YB-10, YB-11, YB-12, YB-14, YB-15, YB-22 and YB-23 are similar, their activities are quite different, and analogs YB-10, YB-11 and YB-15 with a trifluoromethyl substitution or a chloro substitution on the side chain are most potent with $EC_{50}$S of 0.012-0.048 μM. Similarly, although structures of enamide amine analogs YB-17, YB-18, YB-19, YB-20 and YB-21 are similar, their activities are quite different, and analogs YB-17, YB-18 and YB-21 with a trifluoromethyl substitution or a chloro substitution on the side chain are most potent with $EC_{50}$S of 0.34-1.1 μM. This suggests the importance of certain structural features with appropriate size and lipophilicity on the side chain. Excessive size and lipophilicity can reduce the activity (CF3-substituted analog YB-11: $EC_{50}$ 0.012 μM vs di-CF3-substituted analog YB-22: $EC_{50}$ 0.21 μM vs Ph-substituted analog YB-12: $EC_{50}$ 0.60 μM), and possibly lead to poor solubility and other undesired drug properties, e.g. Resiniferatoxin (RTX), a potent TRPV1 agonist with a large lipophilic side chain in region C, is insoluble in water and toxic (*PNAS* 2016, 113, E137-E145); 4. Enamides represent key structural motifs in various bioactive natural products (*Organic Letters,* 2014, 16, 3444). Introduction of a rigid trans-enamide motif in enamide phenol analogs provided favorable conformation for TRPV1 binding and increased the potency (more discussion in Example 30; FIG. 5). Enamide phenol analog YB-11 showed the highest potency with an $EC_{50}$ of 0.012 μM. Introduction of trans-enamide motif in aniline analogs decreased the potency (YB-11 $EC_{50}$ of 0.012 μM vs. YB-17 $EC_{50}$ of 1.1 μM), possibly due to the added desolvation energy required for the aniline; 5. Introducing polar PEG (polyethylene glycol) substitution on amine analog and phenol analog resulted in decreased potency (YB-13 $EC_{50}$ of 3.1 μM vs. YB-2 $EC_{50}$ of 0.082 μM; YB-16 $EC_{50}$ of 0.93 μM vs. YB-11 $EC_{50}$ of 0.012 μM).

Example 29: Select YB Analogs Desensitize TRPV1 in Mouse Neurons

Figure 6:
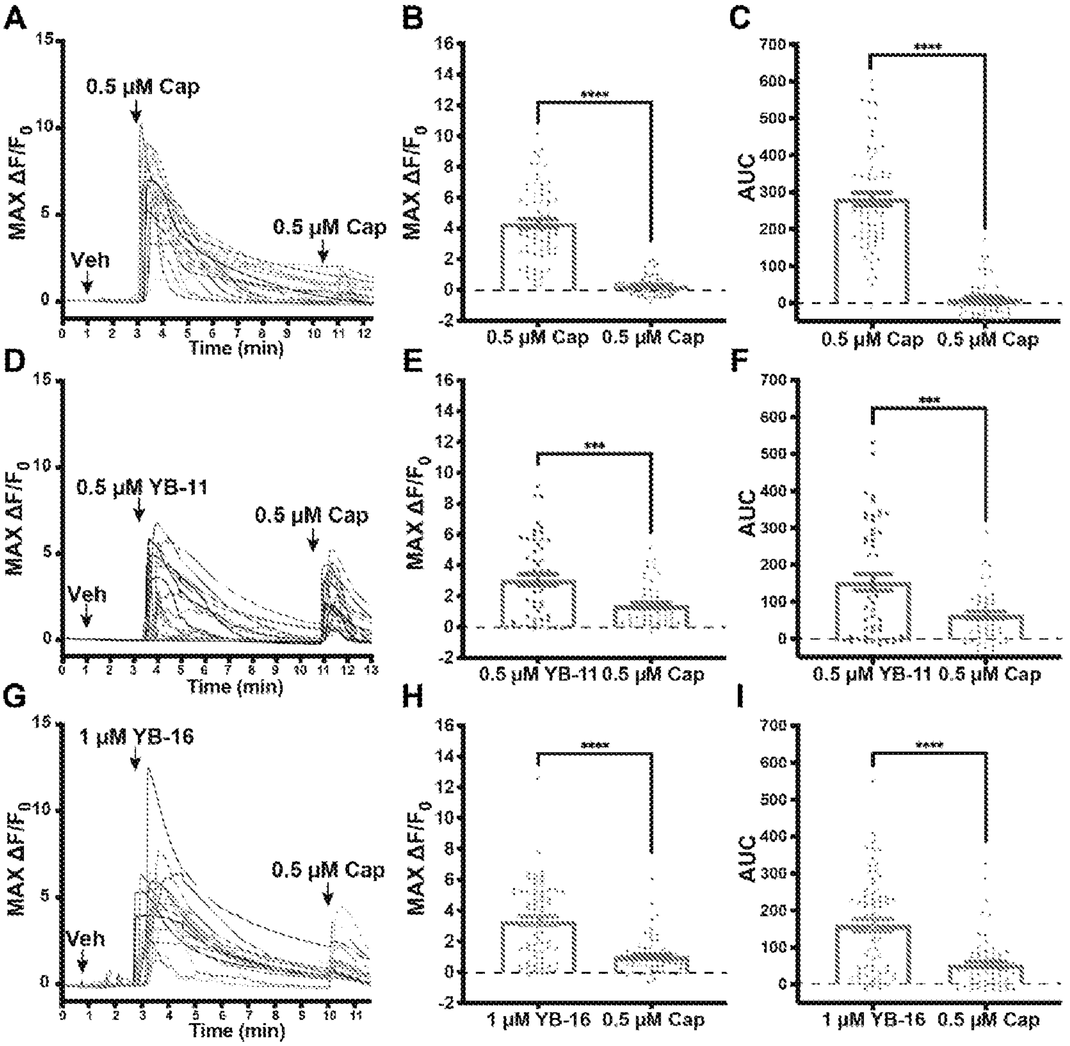
FIG. 6 represents the graphs showing YB-11 and YB-16 desensitizing TRPV1-sensitive dorsal root ganglion as assessed with in vitro $Ca^{2+}$ imaging. A. Representative traces from an experiment where dissociated DRG neurons were treated with capsaicin (0.5 μM) approximately 7.5 minutes before another treatment with capsaicin (0.5 μM). B. The max $Ca^{2+}$ signal from capsaicin was significantly reduced after initial capsaicin response. C. The area under of the curve for the $Ca^{2+}$ signal from capsaicin was significantly reduced after initial capsaicin response. D. Representative traces from an experiment where dissociated DRG neurons were treated with YB-11 (0.5 μM) approximately 7.5 minutes before a treatment with capsaicin (0.5 μM). E. The max $Ca^{2+}$ signal from capsaicin was significantly reduced after initial YB-11 response. F. The area under of the curve for the $Ca^{2+}$ signal from capsaicin was significantly reduced after initial YB-11 response. G. Representative traces from an experiment where dissociated DRG neurons were treated with YB-16 (1.0M) approximately 7.5 minutes before a treatment with capsaicin (0.5 μM). H. The max $Ca^{2+}$ signal from capsaicin was significantly reduced after initial YB-16 response. I. The area under of the curve for the $Ca^{2+}$ signal from capsaicin was significantly reduced after initial YB-16 response. Paired t-test *P<0.001, **P<0.0001. Error bars in B, C, E, F, H, I shown as mean±SEM.

To further evaluate the impact of YB analogs on TRPV1 function, YB-11 and YB-16 were tested in primary mouse dorsal root ganglion (DRG) neurons using $Ca^{2+}$ imaging. DRG was isolated from male and female mice expressing GCaMP6f in neurons (B6J.Cg-Gt(ROSA) $26Sor^{tm95.1(CAG-GCaMP6f)Hze}$/MwarJ×B6.Cg-Tg(Nes-cre) 1Kln/J). After isolation, neurons were dissociated and prepared as described (Neuroscience 2001, 103, 219). DRG neurons respond to capsaicin with an extracellular $Ca^{2+}$ influx that desensitizes with multiple bath applications of the capsaicin (*J Neurosci* 1997, 17, 3525*; Cell Calcium* 2004, 35, 471). Corroborating these data, it was found that 0.5 μM capsaicin reduced a subsequent application of 0.5 μM capsaicin with 96% TRPV1-sensitive neurons showing desensitization (FIG. 6A-C). This included a statistically significant reduction in max signal of the second application (Paired t-test P<0.0001; FIG. 6B) and area under the curve of the second application (Paired t-test P<0.0001; FIG. 6C). This experiment was repeated but used YB-11 and YB-16 as the first treatment compounds followed by capsaicin application. A strong $Ca^{2+}$ signal after YB-11 (0.5 μM) application was found along with a reduction in the subsequent capsaicin application with 67% TRPV1-sensitive neurons showing desensitization (FIG. 6D-F). This included a statistically significant reduction in max signal of the second application (Paired t-test P<0.001; FIG. 6E) and area under the curve of the second application (Paired t-test P<0.001; FIG. 6F). A strong $Ca^{2+}$ signal after YB-16 (1.0 μM) application was also found along with a reduction in the subsequent capsaicin (0.5 μM) application with 79% TRPV1-sensitive neurons showed desensitization (FIG. 6G-I). This included a statistically significant reduction in max signal of the second application (Paired t-test P<0.0001; FIG. 6H) and area under the curve of the second application (Paired t-test P<0.001; FIG. 6I).

Example 30: Pungency Test for Select YB Analogs

The high pungency of capsaicin causes serious side effects and limits the dosing level in clinical use. It is important to identify less pungent capsaicin analogs. Three analogs (YB-2, 11, and 16) were selected for pungency testing. To assess compound pungency in the Relative Pain-producing Potency (RPP) scale, the rodent eye wiping assay was used (*Eur J Med Chem* 2009, 44, 3345). 5 μl of vehicle (20% Tween-80 in saline) or dilute compound (capsaicin 0.01, 0.1, 0.25, 1 mg/ml; YB-2 0.01, 0.1, 1 mg/ml; YB-11 0.01, 0.1, 1 mg/ml; YB-16 0.1, 0.25, 1, 1.5 mg/ml in vehicle) was applied to the eyes of mice (equal numbers of male and female mice used). The number of forearm wipes to the eye was recorded over 1 min. All wipe values were normalized to the control vehicle group (n=6; 10.12±1.88 SEM wipes) by subtracting the vehicle mean from measured wipes for each individual trial. The dose that produced 10 normalized wipes was defined as the moderate pain producing potency (MPP) for capsaicin and all YB compounds. The MPP for capsaicin was set to a relative pain-producing potency of 100 and YB MPP values were used to calculated YB RPP values. A wash-out period of ≥3 days was used between re-testing any individual mouse.

Figure 7:
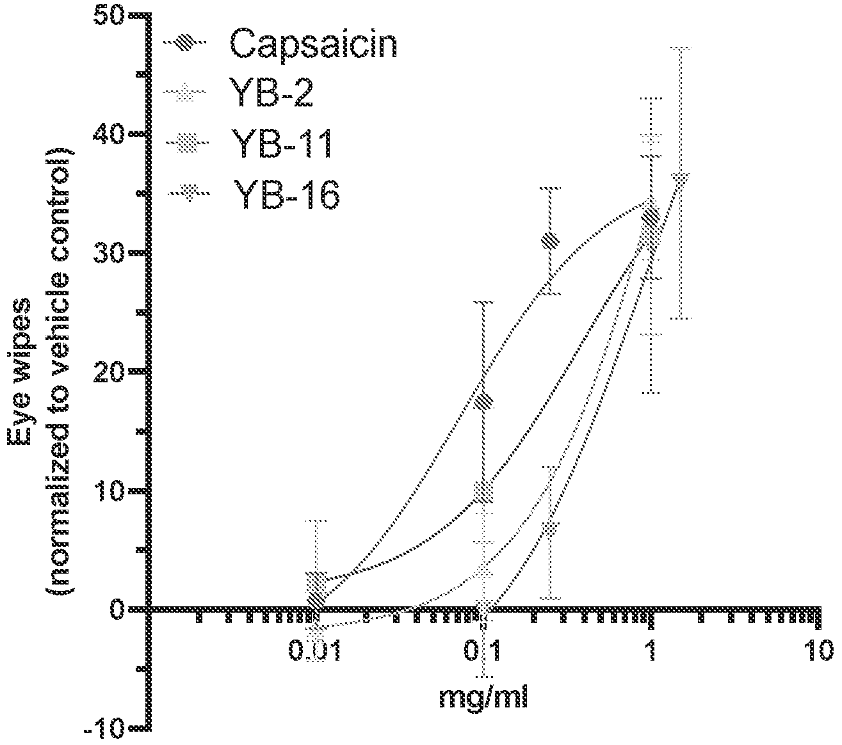
FIG. 7 is a graph showing the Dose Response Curves for Pungency Analysis. Dose-response curves obtained based on the number of protective eye wipes after dilute concentrations were instilled into the eye of male and female mice (at least 3 concentrations per compound). n=8 for capsaicin, YB-16. n=6 for YB-2 and YB-11. Data presented as normalized mean±SEM. Eye wipes normalized to vehicle control (n=8) response.

All three analogs showed lower relative pain-producing potency (RPP) than capsaicin, with YB-16 showing >7-fold reduction in pungency (Table 2; FIG. 7). These results indicate that the undesired pungency in capsaicin can be reduced by structural modifications.

TABLE 2

Pungency comparison from rodent eye wiping assay

| Compound | Pungency (SHU) | MPP mg/ml | Pungency (RPP) |
|---|---|---|---|
| Capsaicin | 16,000,000 | 0.041 | 100 |
| YB-2 | n.t. | 0.233 | 17.6 |
| YB-11 | n.t. | 0.101 | 40.6 |
| YB-16 | n.t. | 0.302 | 13.6 |

Figure 8:
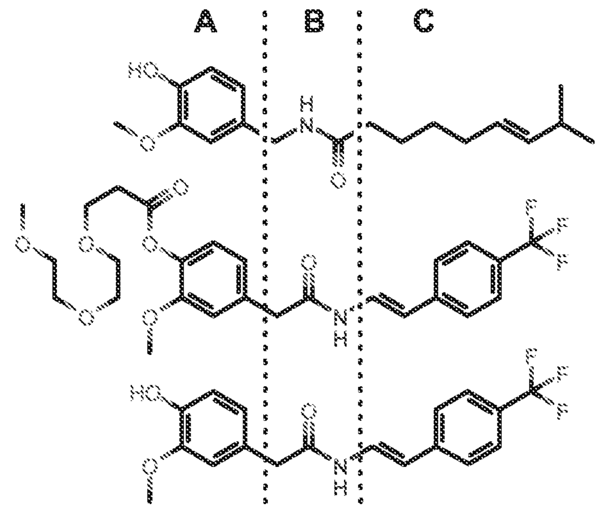
FIG. 8 is a graph showing the structures of Capsaicin, YB-16, and YB-11.

SHU—Scoville Heat Units;
MPP—Moderate Pain-Producing Potency concentration;
RPP—Relative Pain-Producing Potency with Capsaicin set to 100;
n.t.—not tested TRPV1 has a complex polymodal activation profile because it is able to sense multiple stimuli, such as noxious pain, heat, protons, ligand binding, and a number of products of cellular mechanisms (*Nat Commun* 2021, 12, 2154*; PNAS* 2016, 113, E137-E145). Several TRPV1 antagonist candidate drugs have failed in clinical trials because, by interfering with the detection of the aforementioned stimuli, they triggered serious side effects such as hyperthermia and impaired detection of painful heat. Thus, successful TRPV1 modulators need to interfere selectively with only a subset of these activation modalities leaving the others unperturbed. The ligand-bounded TRPV1 structures were studied and investigated for these ligands:TRPV1 interactions. Structural changes in regions B & C (FIG. 8) transformed the flexible natural product into a rigid compound with a favorable binding conformation, resulted in additional ligand: receptor interactions such as H-bonding with Tyr513 and Arene-H interaction with Leu671 (FIG. 5). Ligand rigidification is a proven strategy that is used to improve selectivity for conformationally flexible targets (*Eur J Med Chem* 2018, 146, 519). In analogs YB-16/YB-11, reverse trans-enamide linked with aromatic chain effectively rigidifies the flexible natural product, which increases the ligand-receptor interaction, and improves the selectivity and limits the interaction of YB-16/YB-11 with only a small subset of the TRPV1 activation modalities leaving the others unperturbed. That explains why YB-16/YB-11 are highly effective, but less pungent and less toxic in animal models of pain than capsaicin (in vivo efficacy and toxicity study in Example 33).

Example 31: Comparison Between YB-2, YB-11, YB-16 and Capsaicin

As described herein, the TRPV1 activity of capsaicin can be separated from its inherent pungency and hydrophobicity has now been demonstrated. Compared to capsaicin, analogs YB-2 and YB-11 improved human TRPV1 activation potency, decreased pungency and improved the aqueous solubility (Table 3). PEG-ester side chain on YB-16 is labile, and in plasma YB-16 was readily hydrolyzed to form YB-11 (in vivo PK data in Example 32). YB-16 is a prodrug of YB-11 with decreased pungency and improved solubility.

TABLE 3

| Comparison between YB-2, YB-11, YB-16 and Capsaicin | | | |
|---|---|---|---|
| Compound | TRPV1 $EC_{50}$ (μM) | Solubility (mg/mL) | Pungency RPP |
| Capsaicin | 0.11 | 0.013 | 100 |
| YB-2* | 0.082 | 20 | 17.6 |
| YB-11 | 0.012 | 0.027 | 40.6 |
| YB-16 | 0.93 | 0.16 | 13.6 |

Note:

*YB-2 was tested as a HCl salt.

RPP—Relative Pain-Producing Potency with Capsaicin set to 100.

Example 32: DMPK Evaluation for Select YB Compounds

In vitro and in vivo DMPK evaluation was conducted for select YB compounds. YB-2 was stable in mouse plasma with a $T_{1/2}$ of 2189 min and 2 control compounds performed as expected (Table 4). YB-2 was rapidly metabolized by mouse liver microsome with a $T_{1/2}$ of 3.1 min and the control compound performed as expected (Table 5). After YB-2 PO administration (0.4 mg/kg), YB-2 concentrations in mouse plasma were below quantitation limit (1 ng/mL). For IV administration, YB-2 had a $T_{1/2}$ of 0.17 hr (Table 6). For SubQ administration (2 mg/kg), YB-16 had a $T_{1/2}$ of 1.2 hr (YB-16 is a prodrug and readily converted into YB-11 in vivo; YB-11 was the target compound in PK sample analysis). Based on PK data, IV and SubQ was optimized for systematic administrations instead of PO in addition to intraplantar administration, a common method of TRPV1 modulator delivery. PK formulation [35% NMP (N-Methyl-2-Pyrrolidone) in saline] was used as vehicle for efficacy studies in animal models of pain. PK doses were used to guide the design of dosing parameters for the efficacy experiments.

TABLE 4

| Mouse plasma stability | | | | |
|---|---|---|---|---|
| Compound | Species | Concentration (μM) | $T_{1/2}$ (min) | % Remaining at $T_{120}$ |
| YB-2 | C57BL6 | 2 | 2189 | 97 |
| Propantheline | mouse | 5 | 55 | 20 |
| Lovastatin | | 5 | 12 | 0.2 |

TABLE 5

| Mouse liver microsome stability | | | | | |
|---|---|---|---|---|---|
| Compound | Species | Concentration (μM) | $T_{1/2}$ (min) | % Remaining at $T_{120}$ | $Cl_{int}$ (L/hr/kg) |
| YB-2 | C57BL6 | 2 | 3.1 | 0.1 | 107 |
| Verapamil | mouse | 2 | 5 | 0 | 65 |

TABLE 6

| In vivo mouse PK summary | | | | | | | | | |
|---|---|---|---|---|---|---|---|---|---|
| Compound | Species | Route | Dose (mg/kg) | λz (1/hr) | $T_{1/2}$ (hr) | $T_{max}$ (hr) | $C_{max}$ (ng/mL) | $AUC_{last}$ (hr*ng/mL) | MRT (hr) |
| YB-2 | C57BL6 | IV | 0.4 | 4.1 | 0.17 | 0.083 | 123 | 38 | 0.16 |
| YB-16* | mouse | SubQ | 2 | 0.59 | 1.2 | 0.5 | 104 | 173 | 1.2 |

Note: λz: The elimination rate constant; AUClast: area under a concentration of analyte vs. time calculated from time zero to the time of the last positive Y value; MRT: Mean Residence Time. *YB-16 dose (2 mg/kg) was calculated based on YB-11; YB-11 was the target compound in PK sample analysis.

Example 33: In Vivo Efficacy Studies in Three Animal Models of Pain

The potential for the synthetic analogs described herein to reduce pain-like behavior in the formalin test, hot plate test, and an operant pain tolerance test (Table 7) was evaluated. The impact of YB compounds, a positive control (capsaicin), and a negative vehicle control on pain-related behaviors were tested in mice and the experiments were completed and analyzed, blinded to group assignment (i.e., treatment or control). Dosing estimations were guided by PK data and by comparing in vitro agnostic activity in $Ca^2$-flux assay to similar compounds. Dosing for positive control was based on the literature (*Molecular Pain* 2015, 11, 22). C57BL6 mice (male/female 1:1) were ordered from Charles River. Oral delivery was not considered due to poor oral bioavailability (Example 32). IV delivery was tested but was found to be ineffective, possibly due to short half-life (Example 32). The other two most common methods of TRPV1 modulator delivery are intraplantar (ventral surface of the paw) or SubQ. These were utilized for all in vivo testing described below. Briefly, it was found that (1) intraplantar YB-16 and YB-11 were able to reduce spontaneous formalin behavior, (2) subcutaneous YB-16 was able to reduce hot plate algesia, and (3) intraplantar YB-16 trended to reduce sensitivity to hot plate after inflammatory injury compared to vehicle. YB compound treatments were well-tolerated by animals and did not cause adverse effect. All experiments were designed with the 3R's Experimental Design Assistant to maximize scientific rigor and blinding. These data are described as follows.

TABLE 7

Summary of in vivo efficacy tests for YB-16 and Capsaicin

| In vivo models | Milestone Metric | Route of Administration | YB-16 Outcome | Capsaicin Outcome |
|---|---|---|---|---|
| 1. Formalin Assay | Analgesia effect | Intraplantar (paw injection) | 60% & 54% reductions in first & second phase pain behavior with no animal death or sedation | 44% reduction in first phase pain behavior with animal death and sedation |
| 2. Hot-Plate Assay | Anti-hyperalgesic effect | SubQ (systematic) | Reduction in hot-plate reaction (270% MPE increase compared to vehicle) with no animal death or sedation | Trial in female mice had to be stopped after the first two female mice died within minutes of treatment; One male mouse had sedative effect |
| 3. Operant Pain Tolerance Assay | Anti-hyperalgesic effect | Intraplantar (paw injection) | Trend for reduced sensitivity to hot plate (spend 145% more time on hot side compared to vehicle) after inflammatory injury with no sedation | Weak trend for reduced sensitivity to hot plate (spend 47% more time on hot side compared to vehicle) after inflammatory injury with sedation |

Figure 9:
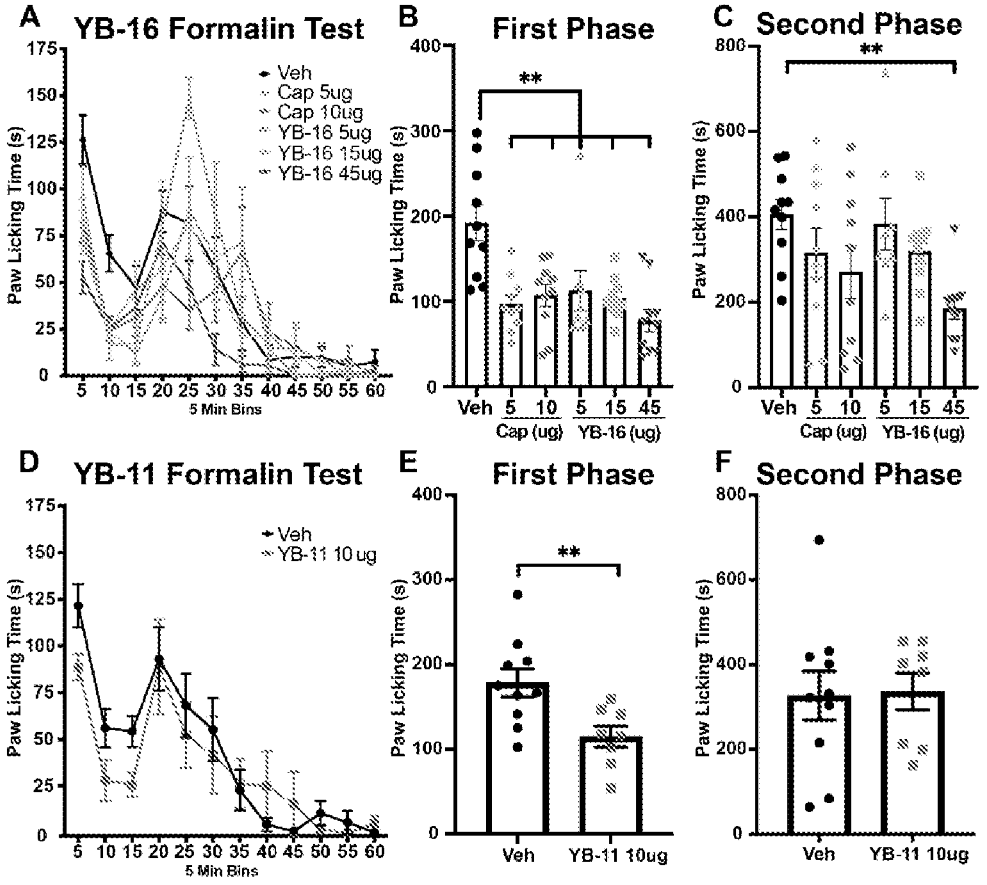
FIG. 9 is a graph showing anti-hyperalgesic effect of YB-16 and YB-11 on formalin-induced pain. A. YB-16 (5, 15, 45 μg) and capsaicin (5, 10 μg) reduce spontaneous pain-like behavior in a dose-related manner (two-way ANOVA P<0.01 main effect treatment, time, and interaction) with significant effects in the (B) first phase (all doses all treatments) and (C) second phase (45 μg YB-16 only) of the test. D. YB-11 (10 μg) impact on spontaneous pain-like behavior (two-way ANOVA P<0.01 main effect time) with significant effects in the (E) first phase but not (F) second phase of the test. **P< 0.01 Dunnett's multiple comparison (B-C) and t-test (E). N=8-10 all groups. Data shown as mean±SEM.

Model 1—The formalin test measures spontaneous pain-like behavior following intraplantar formalin injection. This behavior is a stereotyped two phase response. Mice were tested in the right hind paw with YB-2 (3.3, 10, 30 μg), YB-16 (5, 15, 45 g), YB-11 (10 g), capsaicin (5, 10 g), or vehicle (35% NMP in saline) 2 hr prior to formalin injection in the right hind paw. In agreement with previous findings (*Molecular Pain* 2015, 11, 22), capsaicin at 5-10 g dose was able to reduce first phase spontaneous behavior by 44% (FIG. 9B), but reduction in the second phase was not statistically significant (FIG. 9C). Both YB-16 (FIG. 9B) and YB-11 (FIG. 9E) reduced formalin first phase behavior (60% for 45 g YB-16 and 36% for 10 g YB-11). YB-16 (45 g) treatment group was the only group that showed statistically significant decrease (54%) in the second phase of the formalin test (FIG. 9C). YB-2 did not reduce formalin behavior at any dose tested for the full cohort but had a significant analgesic effect in the second phase for male mice only (data not shown). One of the capsaicin treated animals died and capsaicin also induced sedation in 20% of animals in 10 g dosing group. So 5 g is capsaicin's maximum tolerated dose (MTD). No mice treated with YB-16, YB-11 or YB-2 died or experienced sedative reaction despite YB-16 was dosed up to 9× above capsaicin's MTD (45 g vs. 5 g).

Model 2—The impact of systemic delivery of YB compounds in the hot-plate assay (a classic test of analgesia) was evaluated. Mice were treated subcutaneously with YB-16 (3, 6 mg/kg), capsaicin (2 mg/kg), or vehicle. Consistent with the results from the formalin tests, a significant impact of YB-16 on hot plate analgesia in mice [270% MPE (maximum possible effect) increase for 6 mg/kg YB-16 compared to vehicle control] (FIG. 10A) was found. Most strikingly, however, was the lack of any negative reaction from YB-16 treatment compared to a serious adverse reaction in female mice from capsaicin treatment. Based on the literature (*Naunyn Schmiedebergs Arch Pharmacol* 1982, 320, 205-16; Neuropharmacology 1981, 20, 505), capsaicin dosed at 2 mg/kg had previously been shown to be analgesic and safe in mice with SubQ administration. However, the trial in female mice had to be stopped after the first two female mice died within minutes of capsaicin treatment. No male animals died, but one male animal experienced sedative effect. No mice (male or female) died or sedated following treatment with YB-16 including at 6 mg/kg.

Figure 10:
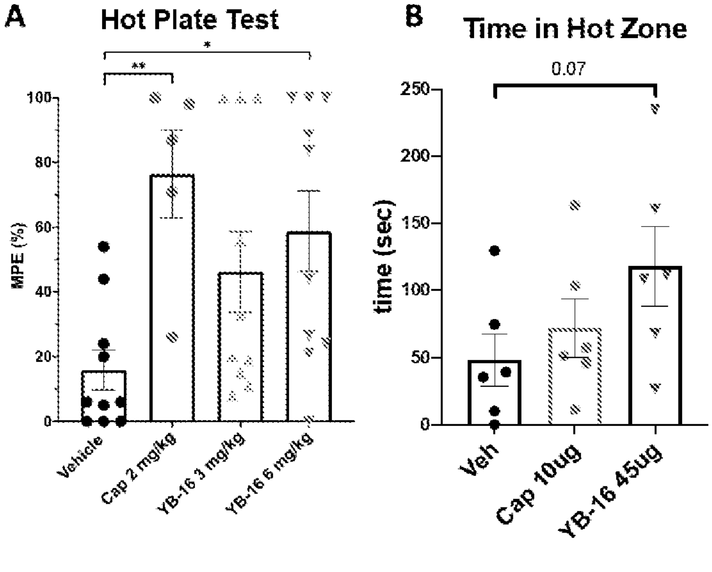
FIG. 10 is a graph showing effect of YB-16 on Thermal Sensitivity. (A) YB-16 (3 and 6 mg/kg) subcutaneously and capsaicin (2 mg/kg) reduced hotplate sensitivity compared to vehicle. One Way ANOVA P=0.01. (B) YB-16 (45 g) intraplantar trended to increase time in a 42° C. chamber. T-test P=0.07. N=5-10 all groups. *P<0.05; **P<0.01.

Model 3—The ability of YB-16 to increase pain tolerance was tested using a newly published Operant Pain Tolerance Assay (*eNeuro* 2020, 7, ENEURO.0210-19.2020). In the assay, mice were trained to seek a sucrose reward that was on a hot 42° C. plate (versus no reward on a neutral 30° C. plate). It was noticed that intraplantar YB-16 treated mice with paw inflammatory injury [induced by Complete Freund's adjuvant (CFA) 24 hrs prior to treatment] trended to spend 145% more time on the hot side of the assay but not necessarily additional time near the sucrose bottle compared to vehicle treated mice (FIG. 10B). These data are consistent with an inflammatory pain relieving effect of YB-16.

Compared to capsaicin, YB-16 demonstrated improved solubility, deceased pungency, strong analgesic effectiveness and lower toxicity in animal models of pain, making it a promising compound that can be dosed at highly efficacious level (≥9× above capsaicin dose based on Formalin Model) in clinical trials. As a result, it will be much easier to achieve therapeutic endpoints.

Example 34: Anticancer Activity Against Human Cancer Cell Lines

Capsaicin shows inhibitory effects against cancer cells of different origin. To evaluate the anticancer potential of the synthetic analogs, these compounds were screened in a human cancer cell growth inhibition assay, which was modified from an ATP Assay (Molecular Probes' ATP Determination Kit, Cat #A22066, Invitrogen). Aggressive, triple-negative breast cancer cell line MDA-MB-231, non-small-cell lung cancer cell line NCI-H460, and ovarian cancer cell line OVACR-8 were selected for screening. These 3 cell lines were selected for 2 reasons: 1. These cell lines express TRPV1; 2. The burden and impact of breast, lung, and ovarian cancers on our society. Cancer cells (4,000-5,000 cells/well) in 96 well half area cell culture plate (Cat #3688, Corning) were incubated in 37° C. with 5% $CO_2$ for 2 h. After the addition of compounds or DMSO control, the cell culture plate was further incubated in 37° C. with 5% $CO_2$ for 4 days. The ATP assay reagent (Cat #A22066, Invitrogen) was added to the cell culture plate and the luminescence signal from each well was recorded on the plate reader (Synergy H1 Multi-Mode Reader, BioTek® Instruments, Inc.; Integration time: 1 second; Emission Maximum: 560 nm; Gain: 135; Read Height: 1.00 mm). The values were plotted against the corresponding concentrations to generate dose response curves and the $IC_{50}$s were calculated. $IC_{50}$ data in Table 8 are shown as Means±SEM from three independent experiments. Capsaicin and most of the new analogs showed moderate growth inhibition activity against these 3 cell lines. Compared to capsaicin, YB-1 was 10-fold more potent against MDA-MB-231 cell line, 18-fold more potent against NCI-H460 cell line and 6-fold more potent against OVACR-8 cell line.

TABLE 8

Human cancer cell growth inhibition activity

| Compound | MDA-MB-231, $IC_{50}$, μM | NCI-H460, $IC_{50}$, μM | OVCAR-8, $IC_{50}$, μM |
|---|---|---|---|
| Capsaicin | 387 ± 120 | 200 ± 65 | 234 ± 31 |
| YB-1 | 38 ± 9.0 | 11 ± 3.7 | 38 ± 8.0 |
| YB-2 | 342 ± 30 | 350 ± 25 | 200 ± 22 |
| YB-3 | 430 ± 90 | 320 ± 86 | 500 ± 120 |
| YB-4 | 469 ± 130 | 270 ± 45 | 300 ± 60 |
| YB-5 | 542 ± 101 | 210 ± 48 | 150 ± 42 |
| YB-6 | 867 ± 72 | 400 ± 46 | 400 ± 51 |
| YB-7 | 386 ± 107 | 200 ± 49 | 310 ± 45 |
| YB-8 | 311 ± 31 | 250 ± 23 | 500 ± 81 |
| YB-9 | 75 ± 20 | 65 ± 15 | 34 ± 12 |
| YB-10 | 115 ± 28 | 73 ± 18 | 34 ± 8.5 |
| YB-11 | 129 ± 21 | 87 ± 10 | 65 ± 7.5 |
| YB-12 | 136 ± 29 | 61 ± 21 | 129 ± 20 |
| YB-13 | 107 ± 7.5 | 100 ± 11 | 200 ± 16 |
| YB-14 | 300 ± 46 | >300 | 500 ± 57 |
| YB-15 | 250 ± 38 | >300 | 101 ± 17 |
| YB-16 | >100 | >100 | 16 ± 3.9 |
| YB-17 | 140 ± 22 | 139 ± 19 | 161 ± 26 |
| YB-18 | 69 ± 16 | 133 ± 18 | 200 ± 21 |
| YB-19 | 103 ± 18 | 117 ± 16 | 100 ± 15 |
| YB-20 | 86 ± 14 | 279 ± 42 | 283 ± 38 |
| YB-21 | 101 ± 20 | 103 ± 13 | 65 ± 14 |
| YB-22 | 74 ± 9.7 | 84 ± 12 | 58 ± 6.5 |
| YB-23 | 90 ± 12 | 88 ± 9.7 | 73 ± 7.8 |

Example 35: Inhibition of Cancer Cell Invasion

After treating cancer cells with capsaicin, researchers found that capsaicin stopped the first stage of metastasis, which is called "invasion". Most cancer deaths occur as a result of the cancer metastasizing, or spreading, to distant parts of the body. It is of great importance to identify capsaicin analogs that are effective in inhibiting cancer cell invasion.

Figure 11:
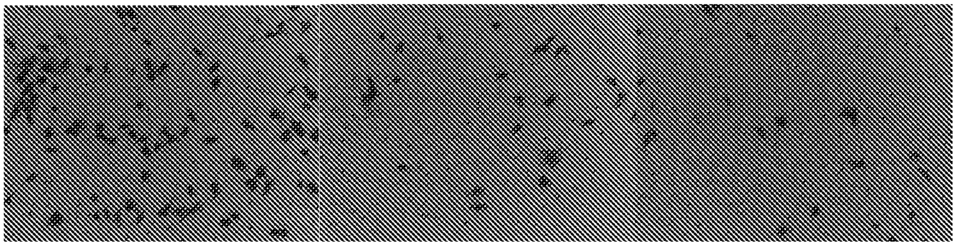
FIG. 11 represents the images of MDA-MB-231 cell invasion assay. Image 1: Control (Cells treated with DMSO), Image 2: Cells treated with Capsaicin (40 μM), Image 3: Cells treated with YB-1 (10 μM).
Figure 12A:
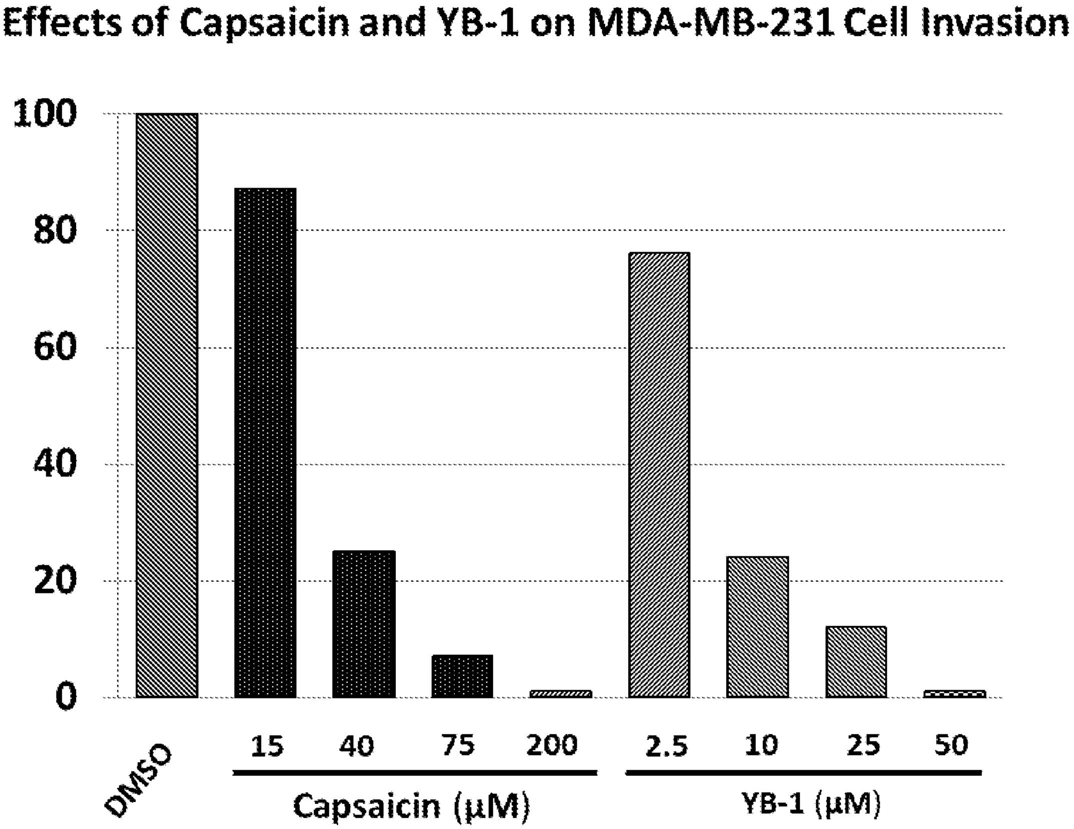
FIGS. 12A-C are the graphs showing the dose-response effects of capsaicin and YB-1 on MDA-MB-231, NCI-H460, and OVCAR-8 cell invasion.

A cancer cell invasion assay was developed based on literature protocols (*Methods* 2005, 37, 208; *EMBO J* 2002, 21, 6289; *Cellular Signalling* 2012, 24, 1276). Membrane matrix gel (Cat #A1413201, ThermoFisher) was diluted in ice-cold, serum-free RPMI 1640 Medium (Cat #31800022, ThermoFisher) at a concentration of 0.5-0.6 mg/mL. Then it was added to the upper compartment (100 μL per cup) of millicell inserts (Cat #PI8P01250, ThermoFisher) placed in a 24-well plate (Part no. 229123, Celltreat). The plate was incubated at 37° C. for 2 h to allow the liquid gel to solidify. RPMI 1640 Medium supplemented with 10% FBS (300 μL) was added to the well of the plate (lower compartment) as attractant, then DMSO or compounds were added. Human cancer cells ($1\times10^5$ cells in 200 μL of RPMI 1640 Medium) were added to the upper compartment of the insert, then DMSO or compounds were added. After the plate was incubated at 37° C. for 24 h, the cells were fixed on the lower side of the insert membrane with 4% formaldehyde and stained with 1% crystal violet (Part no. IS12146, Innovating Science). The invaded cells on the lower side of the filter were counted under an inverted microscope equipped with either a 4× or a 10× objective (FIG. 11). The cell numbers from 5 random views were averaged and plotted as percentage against the DMSO control (FIG. 12A).

YB-1 and capsaicin dose-dependently inhibited the MDA-MB-231, NCI-H460, and OVCAR-8 cell invasion. YB-1 was about 4-fold (MDA-MB-231), 10-fold (NCI-H460), and 3-fold (OVCAR-8) more potent than capsaicin (FIGS. 11 and 12A-C). The higher potency of YB-1 vs. capsaicin in inhibiting the cancer cell invasion was consistent with the cancer cell growth inhibition activity (Table 8). YB-1 is a more promising anticancer compound than capsaicin based on the activity in cancer cell growth inhibition assay and cell invasion assay.

Figure 13A:
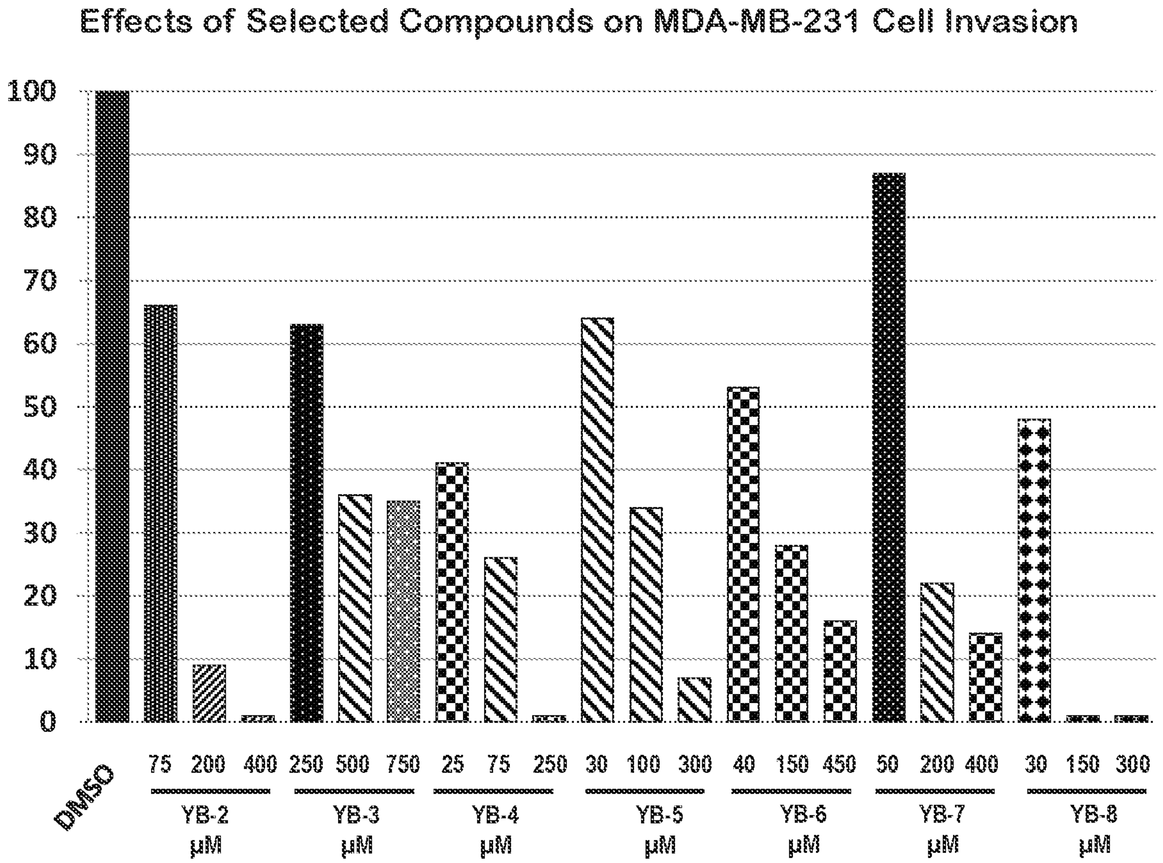
FIGS. 13A-C are the graphs showing the dose-response effects of the select compounds on MDA-MB-231 and NCI-H460 cell invasion.
Figure 13B:
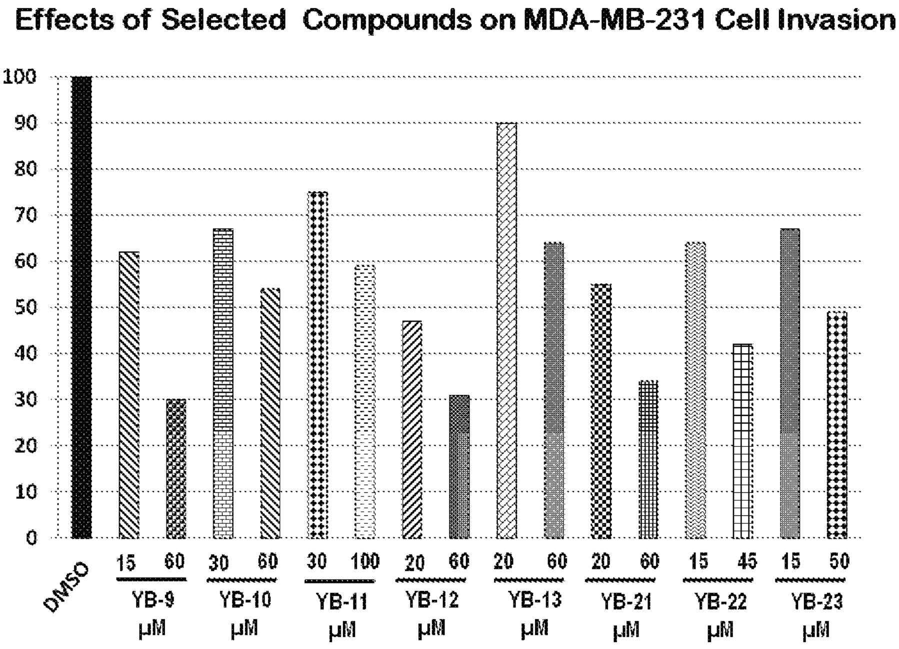
Figure 13C:
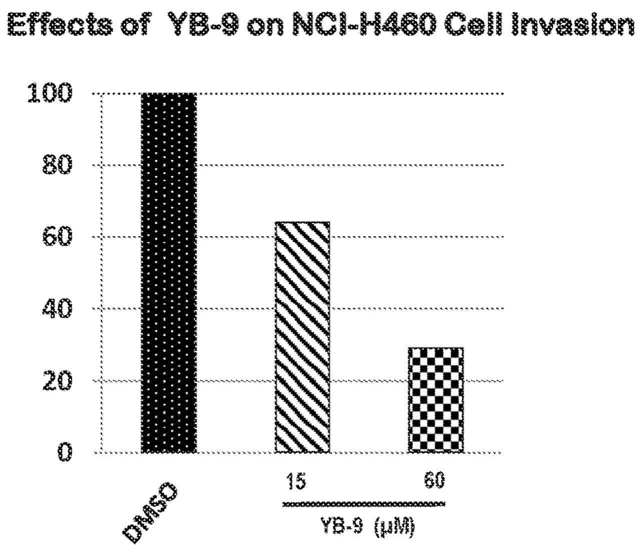

Select analogs (YB-2, YB-3, YB-4, YB-5, YB-6, YB-7, YB-8, YB-9, YB-10, YB-11, YB-12, YB-13, YB-21, YB-22 and YB-23) were tested in the MDA-MB-231 cell invasion assay (FIGS. 13A-B). All the tested compounds dose-dependently inhibited MDA-MB-231 cell invasion. The potency of these compounds in inhibiting cell invasion was consistent with the cancer cell growth inhibition activity (Table 8). YB-9 was also tested in the NCI-H460 cell invasion assay and dose-dependently inhibited the NCI-H460 cell invasion from 15 μM to 60 μM (FIG. 13C).

Example 36: Block the Activation of the Src Protein

The data indicated that TRPV1 agonistic activity of the tested compounds did not correlate with their anticancer activity. For example, although YB-1 was more potent than capsaicin in the cancer cell growth inhibition assay and cell invasion assay, TRPV1 agonistic activity of YB-1 was weaker than that of capsaicin (Table 1). This suggests that biological target in addition to TRPV1 may contribute to the anticancer activity.

Capsaicin can block the activation of the Src protein a protein that is key in regulating the proliferation, survival, and motility of the cells. A cancer cell immunocytochemistry assay was developed to study the effect of capsaicin and synthetic analogs on the activation of the Src protein (*Cellular Signalling* 2012, 24, 1276).

Figure 14A:
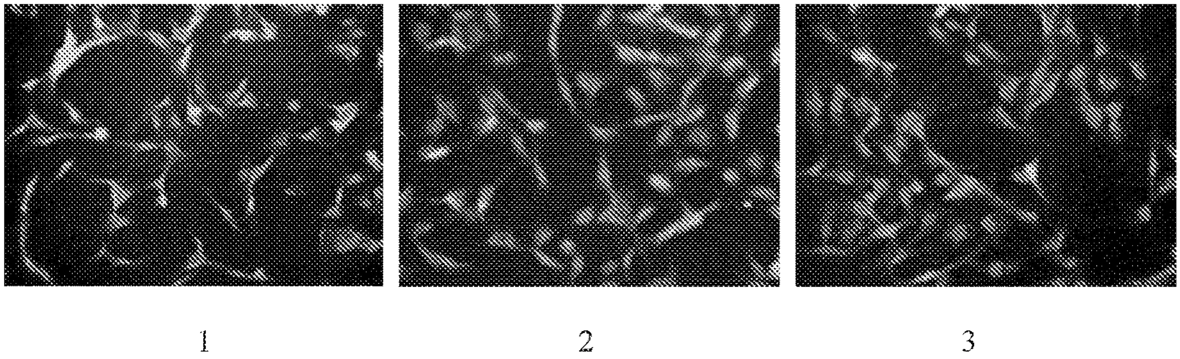
FIGS. 14A-C represent the images of MDA-MB-231 (FIG. 14A), NCI-H460 (FIG. 14B), and OVCAR-8 (FIG. 14C) cell immunocytochemistry assay. Image 1: Control (DMSO); Image 2: Capsaicin (50 μM, 4 h); Image 3: YB-1 (15 μM, 4 h). Green: Human Phospho-Src (Y416), the activated form of Src protein; Blue: DAPI (stain nucleus of cell).
Figure 14B:
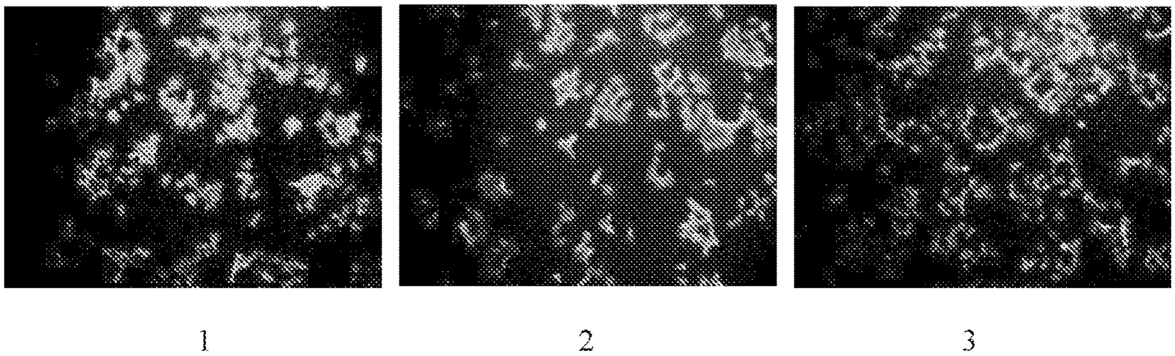
Figure 14C:
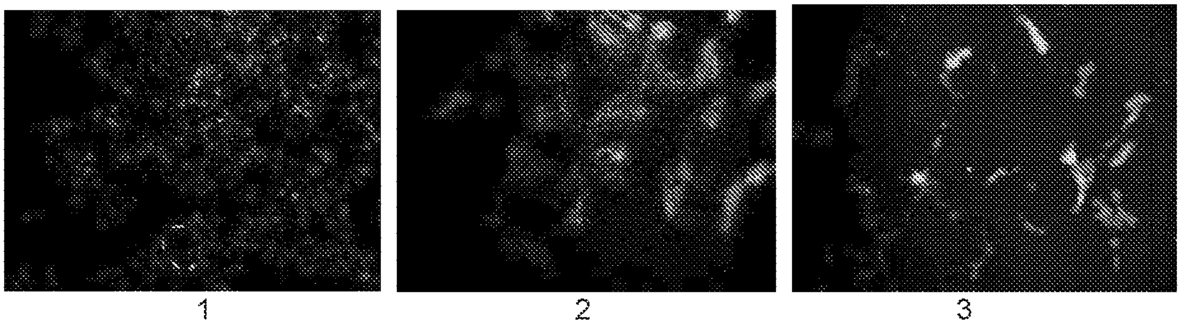

Human cancer cells (15,000 cells/well) in 96 well half area microplate (Cat #3882, Corning) were incubated overnight at 37° C., then compounds or DMSO control were added to the cell culture and incubated at 37° C. for 1-6 h. The cells were sequentially fixed with 4% formalin, permeabilized with 0.5% Triton X-100, blocked with 5% BSA in PBS, incubated with Human Phospho-Src (Y416) Antibody (Cat #MAB2685, R&D Systems) at rt for 2 h, incubated with the secondary antibody Goat Ant-Rabbit IgG H&L (Alexa Fluor 488) (Cat #ab150077, abeam) for 45 min, and incubated with DAPI (Cat #D9542, Sigma-Aldrich) for 5 min. Finally, the cells were washed and covered with PBS. The cell images were visualized on an inverted fluorescence microscope (Leica DMIL Fluorescent Inverted Microscope with Digital Camera, Leica Microsystems). Pictures were taken [FIGS. 14A-C. Green: Human Phospho-Src (Y416), the activated form of the Src protein; Blue: DAPI (stain nucleus of cell)]. The fluorescence intensity values from 5 random cells were averaged, subtracted by the background value (area between cells) and the blank value [the blank control without the Human Phospho-Src (Y416) Antibody], then plotted as percentage against the DMSO control to indicate the effects of compound treatment on the cellular Src kinase phosphorylation levels in the cancer cells (FIGS. 15A-D).

Figure 12B:
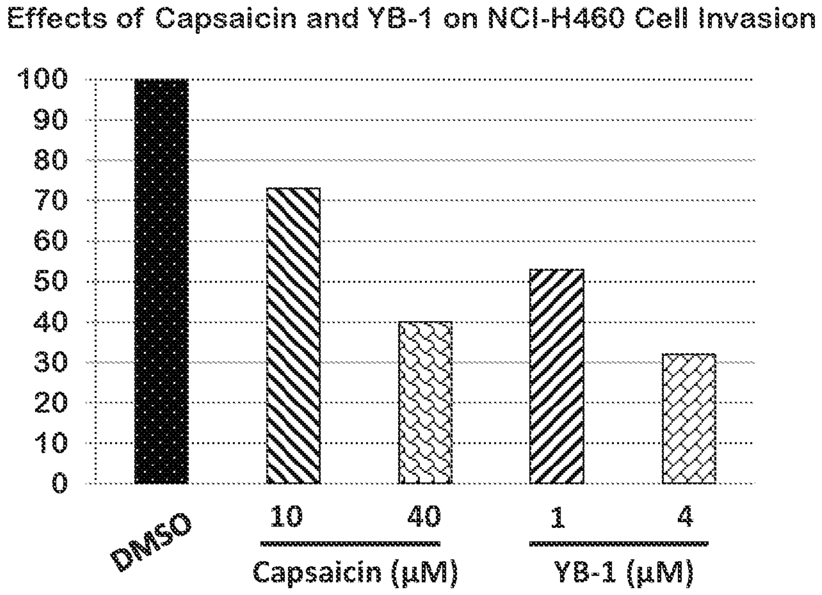
Figure 12C:
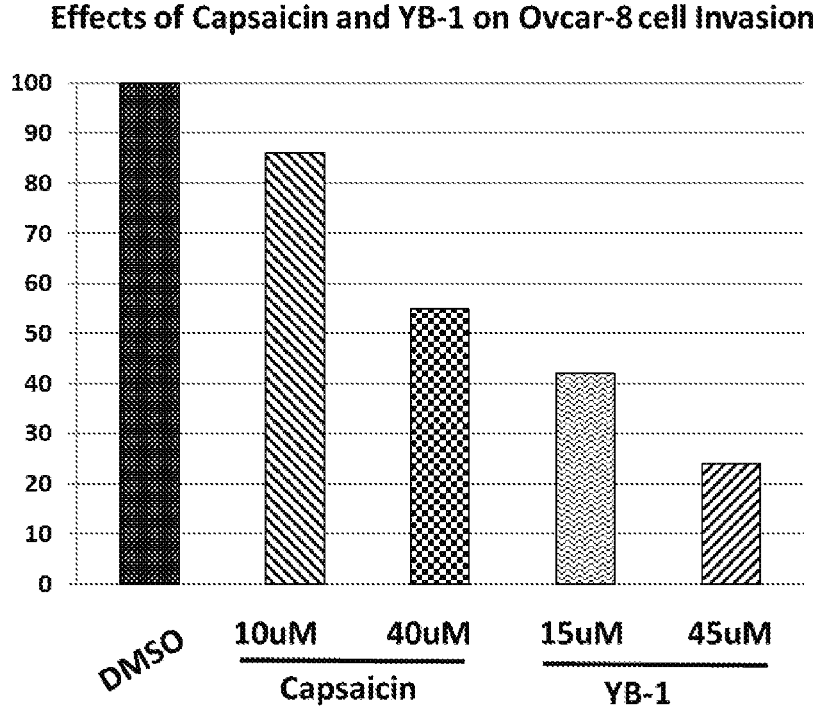
Figure 15A:
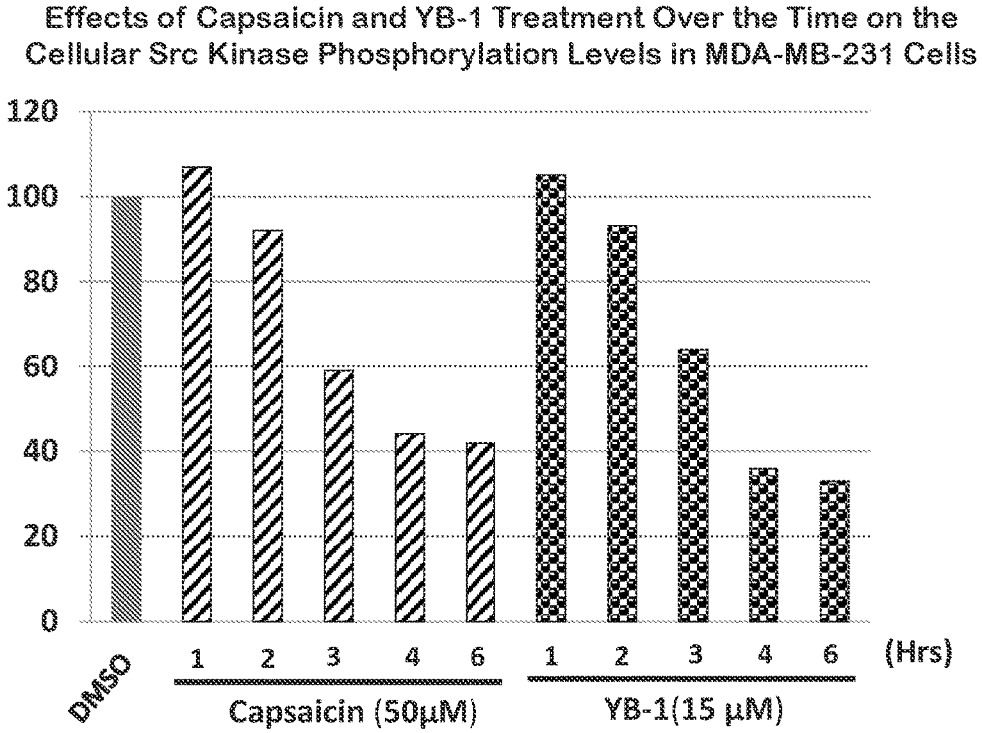
FIGS. 15A, 15C, and 15D are the graphs showing the time-dependent effects of capsaicin and YB-1 treatment on the cellular Src kinase phosphorylation levels in MDA-MB-231 (FIG. 15A), NCI-H460 (FIG. 15C), and OVCAR-8 (FIG. 15D) cells.
Figure 15B:
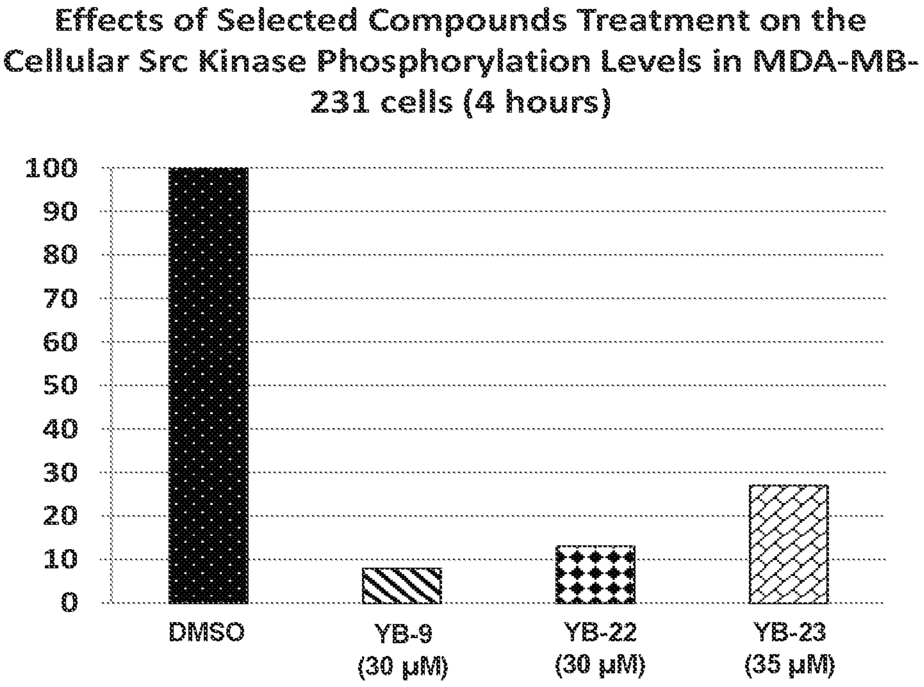
FIG. 15B is the graph showing the effects of select analogs treatment on the cellular Src kinase phosphorylation levels in MDA-MB-231 cells in 4 h.
Figure 15C:
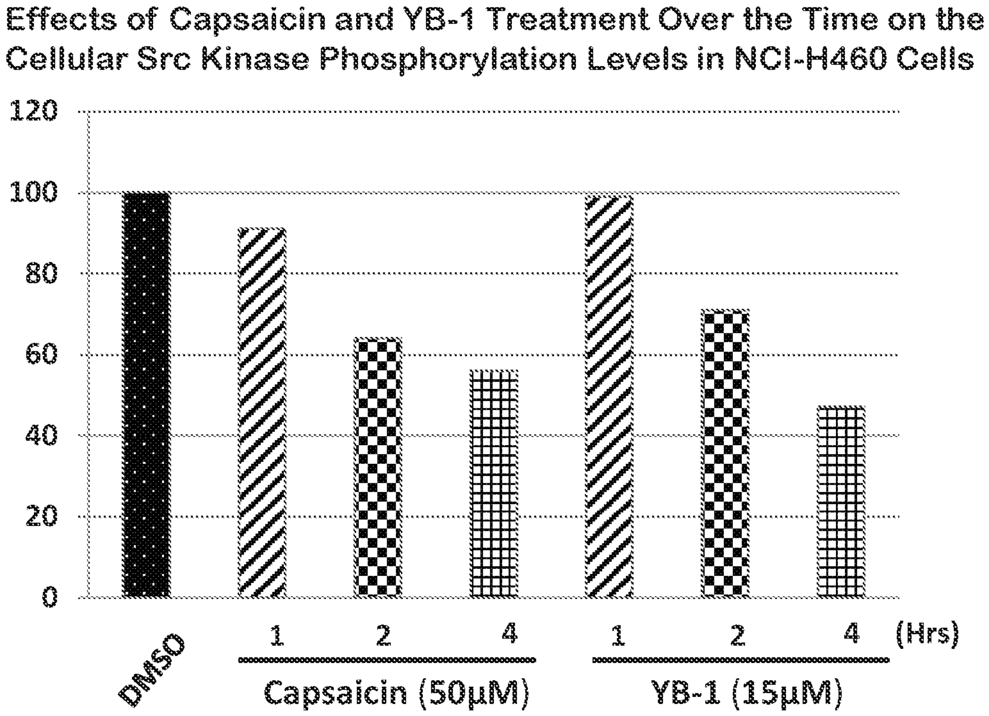
Figure 15D:
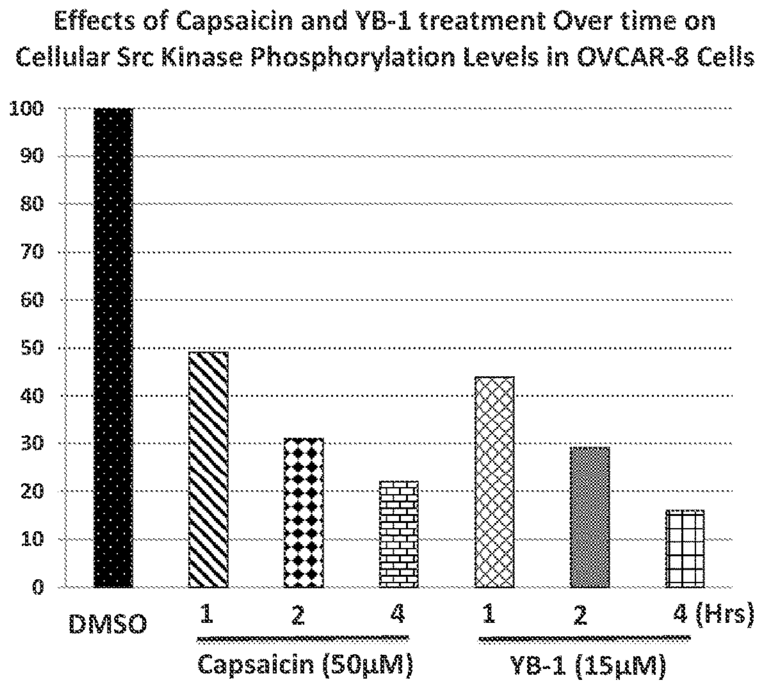

Treatment of MDA-MB-231, NCI-H460, and OVCAR-8 cells with YB-1 (15 μM) or capsaicin (50 μM) time-dependently reduced the cellular Src kinase phosphorylation levels and the effect reached the high level in 4-6 h (FIGS. 15A, 15C, and 15D). YB-1 was at least 3-fold more potent than capsaicin in inhibiting Src protein activation in these 3 cell lines. These results were consistent with the higher potency of YB-1 in inhibiting cancer cell growth and cell invasion (Table 8; FIGS. 12A-C). Treatment of MDA-MB-231 cells with select analogs YB-9, 22, and 23 (at about 40% of $IC_{50}$ concentration from cell growth inhibition assay) also significantly reduced the cellular Src kinase phosphorylation levels in 4 h (FIG. 15B). Phosphorylation activates Src kinase activity, and Src kinase activity regulates proliferation, migration and invasiveness of cancer cells (*Cellular Signalling,* 2012, 24, 1276*; Biochimica et Biophysica Acta,* 2002, 1602, 114; www.medicalnewstoday.com/articles/324911). Taking together, it is reasonable to believe that inhibition of Src protein activation by capsaicin, YB-1 and other analogs contributes to their anti-proliferating activity and anti-invasion activity.

Example 37: In Vivo Anticancer Activity

Figure 16A:
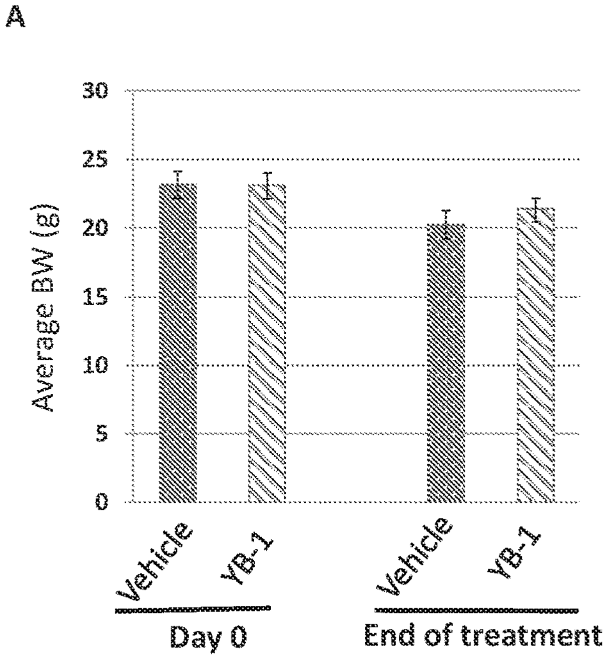
FIGS. 16A-B are the graphs showing YB-1 reduces tumor burden in vivo: A, Quantification of average body weight (BW) of the mice before and after treatment. B, Quantification of tumor burden (average radiant efficiency as measured with IVIS imaging) normalized to day 0. Data shown as mean±SEM. N=5-6 both groups.
Figure 16B:
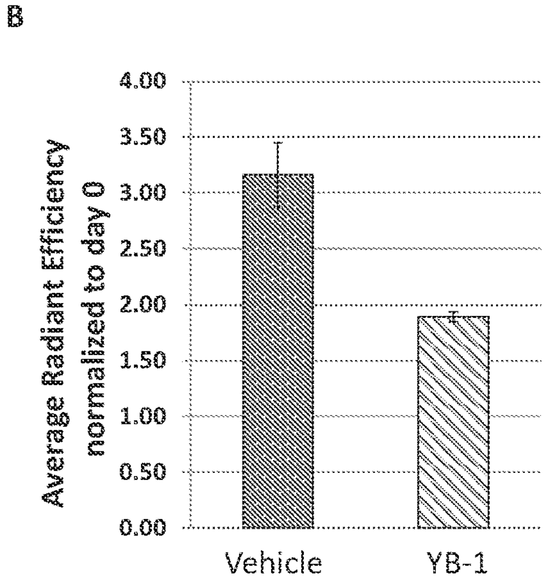

OVCAR-8 cells expressing red fluorescent protein were xenografted intraperitoneally in athymic nude mice to form tumors (*Mol Cancer Ther* 2020, 19, 89). After 4 weeks, mice were dosed with YB-1 or vehicle control (10% N-Methylpyrrolidone-72% PEG400—18% water) for 2 weeks (dosage: 5 mg/kg; ip treatment twice per week). As shown in FIGS. 16A-B, compared to vehicle group, animals treated with YB-1 for 2 weeks had 40% less tumor burden based on average radiant efficiency measured with IVIS and reduced approximately half of the body weight loss (7% average body weight loss for YB-1 treatment group vs. 13% average body weight loss for vehicle group). This indicates that YB-1 treatment inhibited OVCAR-8 ovarian tumor growth in mice and protected the animals from cancer-related body weight loss.

Capsaicin synergized with camptothecin to induce increased apoptosis in human small cell lung cancers (*Biochem pharmacol.* 2017, 129, 54). The in vitro and in vivo anticancer activities suggest that YB-1 and related analogs are promising candidates that can be further developed into novel therapies to combat cancer as single therapies or combination therapies with other anticancer agents, such as camptothecin.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound having the structure (III) as defined below:

(III)

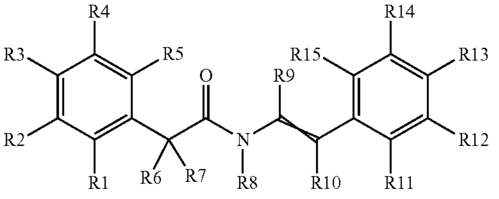

or pharmaceutically acceptable derivative thereof;

wherein R1 is hydrogen;

R2 is hydroxyl, or protected hydroxyl;

R3 is hydroxyl, protected hydroxyl except for alkoxy, amine or protected amine;

R4 is hydrogen;

R5 is hydrogen;

R6 is hydrogen;

R7 is hydrogen;

R8 is hydrogen;

R9 is hydrogen;

R10 is hydrogen;

R11 is hydrogen;

R12 is hydrogen, or haloalkyl;

R13 is hydrogen, or haloalkyl;

R14 is hydrogen, or haloalkyl; and

R15 is hydrogen, wherein at least one of R12, R13, or R14 is haloalkyl.

2. The compound of claim 1, wherein the compound has the structure:

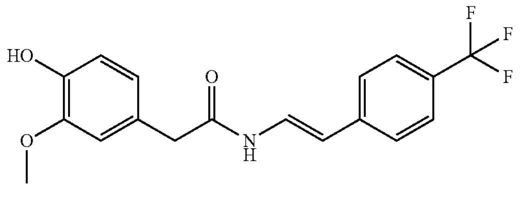

or pharmaceutically acceptable derivative thereof.

3. The compound of claim 1, wherein the compound has the structure:

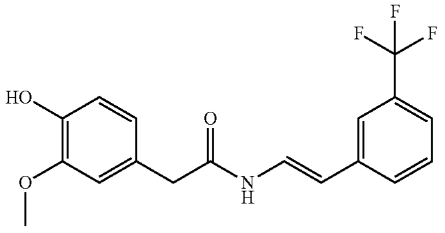

or pharmaceutically acceptable derivative thereof.

4. The compound of claim 1, wherein the compound has the structure:

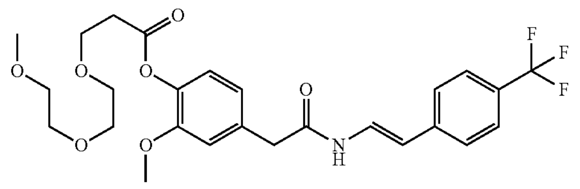

or pharmaceutically acceptable derivative thereof.

5. The compound of claim 1, wherein the compound has the structure:

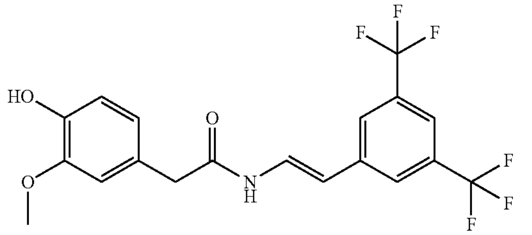 [SMILES: COc1cc(CC(=O)N/C=C/c2cc(C(F)(F)F)cc(C(F)(F)F)c2)ccc1O]

or pharmaceutically acceptable derivative thereof.

6. The compound of claim 1, wherein the compound has the structure:

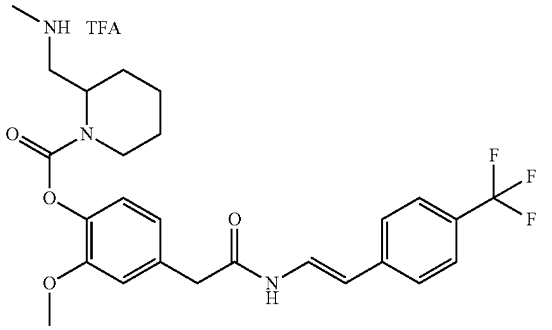 [SMILES: CNCC1CCCCN1C(=O)Oc1ccc(CC(=O)N/C=C/c2ccc(C(F)(F)F)cc2)cc1OC]

or pharmaceutically acceptable derivative thereof.

7. A pharmaceutical composition comprising the compound of claim 1, wherein the compound is present in a therapeutically effective amount sufficient to activate TRPV1 in a subject.

8. A pharmaceutical composition comprising the compound of claim 1, wherein the compound is present in a therapeutically effective amount sufficient to block the activation of Src protein in a subject.

9. A method for treating a disorder associated with a TRP receptor and/or Src protein, the method comprising increasing, or enhancing, the biological activity of a TRP receptor and/or blocking the activation of Src protein in a subject, by administering to the subject a therapeutically effective amount of a compound having the structure:

(III)

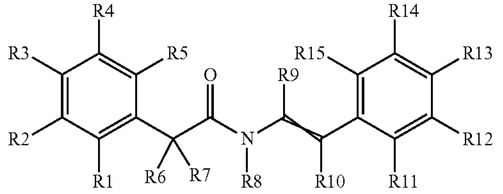

or pharmaceutically acceptable derivative thereof;

wherein R1 is hydrogen;

R2 is hydroxyl, or protected hydroxyl;

R3 is hydroxyl, protected hydroxyl except for alkoxy, amine or protected amine;

R4 is hydrogen;

R5 is hydrogen;

R6 is hydrogen;

R7 is hydrogen;

R8 is hydrogen;

R9 is hydrogen;

R10 is hydrogen;

R11 is hydrogen;

R12 is hydrogen, or haloalkyl;

R13 is hydrogen, or haloalkyl;

R14 is hydrogen, or haloalkyl; and

R15 is hydrogen;

wherein at least one of R12, R13, or R14 is haloalkyl, and wherein the compound activates the TRP receptor and/or blocks the activation of Src protein, thereby treating the disorder.

10. The method of claim 9, wherein the method is for treating a disorder selected from the group consisting of aches and pains of muscles and joints associated with arthritis, post-surgical pain, pain associated with Morton's Neuroma, backache, cancer pain, pain associated with strains and sprains, diabetic pain, pain caused by shingles, pain associated with HIV infection, itching caused by psoriasis, Huntington's disease, neuronal affectations, astrocytomas, mild cognitive impairment, diabetes, obesity, and cancers.

11. The method of claim 9, wherein the compound is the active ingredient of a pharmaceutical composition.

12. The method of claim 9, wherein the compound has the structure:

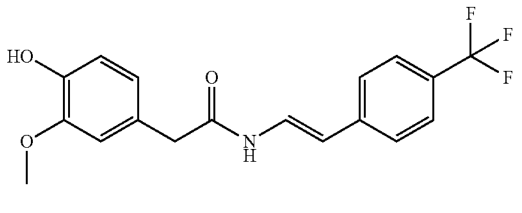 [SMILES: COc1cc(CC(=O)N/C=C/c2ccc(C(F)(F)F)cc2)ccc1O]

or pharmaceutically acceptable derivative thereof.

13. The method of claim 9, wherein the compound has the structure:

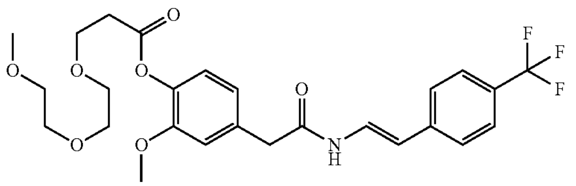 [SMILES: COCCOCCOCCC(=O)Oc1ccc(CC(=O)N/C=C/c2ccc(C(F)(F)F)cc2)cc1OC]

or pharmaceutically acceptable derivative thereof.

14. The method of claim 9, wherein the compound is present in an amount effective to activate TRPV1 and/or reduce pain in vitro or in vivo.

15. The method of claim 9, wherein the compound is present in an amount effective to inhibit cancer growth and/or inhibit cancer metastasis in vitro or in vivo.

16. The method of claim 9, wherein the compound has the structure:

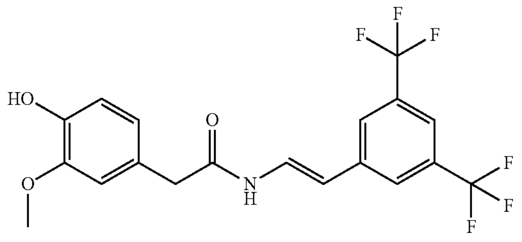 [SMILES: COc1cc(CC(=O)N/C=C/c2cc(C(F)(F)F)cc(C(F)(F)F)c2)ccc1O]

or pharmaceutically acceptable derivative thereof.

17. The method of claim 9, wherein the compound has the structure:

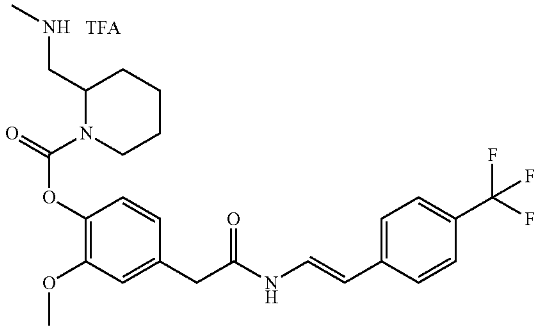 [SMILES: CNCC1CCCCN1C(=O)Oc1ccc(CC(=O)N/C=C/c2ccc(C(F)(F)F)cc2)cc1OC]

or pharmaceutically acceptable derivative thereof.

18. The method of claim 9, wherein the compound has the structure:

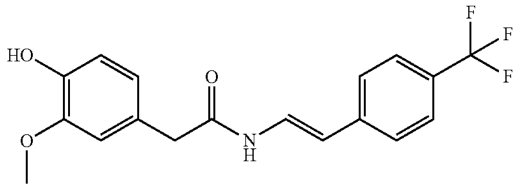 [SMILES: COc1cc(CC(=O)N/C=C/c2ccc(C(F)(F)F)cc2)ccc1O]

or pharmaceutically acceptable derivative thereof.

* * * * *